(12) United States Patent
Aoki et al.

US011518994B2

(10) Patent No.: US 11,518,994 B2
(45) Date of Patent: Dec. 6, 2022

(54) ARTIFICIAL SINGLE GUIDE RNA AND USE THEREOF

(71) Applicant: BONAC CORPORATION, Kurume (JP)

(72) Inventors: Eriko Aoki, Kurume (JP); Tadaaki Ohgi, Kurume (JP); Takashi Kinoshita, Kurume (JP)

(73) Assignee: BONAC CORPORATION, Kurume (JP)

( * ) Notice: Subject to any disclaimer, the term of this patent is extended or adjusted under 35 U.S.C. 154(b) by 858 days.

(21) Appl. No.: 16/073,998

(22) PCT Filed: Jan. 30, 2017

(86) PCT No.: PCT/JP2017/003251
§ 371 (c)(1),
(2) Date: Jul. 30, 2018

(87) PCT Pub. No.: WO2017/131237
PCT Pub. Date: Aug. 3, 2017

(65) Prior Publication Data
US 2019/0382758 A1     Dec. 19, 2019

(30) Foreign Application Priority Data

Jan. 30, 2016   (JP) .............................. JP2016-016743

(51) Int. Cl.
| | |
|---|---|
| *C12N 15/11* | (2006.01) |
| *C12N 9/22* | (2006.01) |
| *C12N 15/90* | (2006.01) |
| *C07C 229/04* | (2006.01) |
| *C07C 229/34* | (2006.01) |
| *C12N 15/113* | (2010.01) |
| *C07F 9/22* | (2006.01) |
| *C40B 50/06* | (2006.01) |

(52) U.S. Cl.
CPC ............ *C12N 15/11* (2013.01); *C07C 229/04* (2013.01); *C07C 229/34* (2013.01); *C07F 9/222* (2013.01); *C12N 9/22* (2013.01); *C12N 15/907* (2013.01); *C40B 50/06* (2013.01); *C12N 15/113* (2013.01); *C12N 2310/20* (2017.05); *C12N 2310/3181* (2013.01); *C12N 2320/51* (2013.01); *C12N 2330/30* (2013.01); *C12N 2800/80* (2013.01)

(58) Field of Classification Search
CPC ..... C07C 229/04; C07C 229/34; C12N 15/11; C12N 15/113; C12N 15/907; C12N 2310/20; C12N 2310/3181; C12N 2330/30; C12N 2800/80

USPC ...... 424/9.1; 435/6.1, 91.1, 91.31, 455, 458; 514/44 A, 44 R; 536/23.1, 24.5
See application file for complete search history.

(56) References Cited

U.S. PATENT DOCUMENTS

| | | | |
|---|---|---|---|
| 2012/0010271 A1 | 1/2012 | Ohgi et al. | |
| 2012/0035246 A1 | 2/2012 | Ohgi et al. | |
| 2014/0329886 A1 | 11/2014 | Ohgi et al. | |
| 2015/0105443 A1 | 4/2015 | Ohgi et al. | |
| 2016/0251640 A1* | 9/2016 | May .......................... | A61P 9/10 435/196 |
| 2016/0319282 A1 | 11/2016 | Kuroda et al. | |

FOREIGN PATENT DOCUMENTS

| | | | |
|---|---|---|---|
| CN | 105755040 A | 7/2016 | |
| WO | 2012/005368 A1 | 1/2012 | |
| WO | 2012/017919 A1 | 2/2012 | |
| WO | 2013/077446 A1 | 5/2013 | |
| WO | 2013/103146 A1 | 7/2013 | |
| WO | 2013/133393 A1 | 9/2013 | |
| WO | WO-2013176772 A1 * | 11/2013 | ........... A01H 6/4684 |
| WO | 2013/180038 A1 | 12/2013 | |
| WO | WO-2014124226 A1 * | 8/2014 | ............ A01N 63/00 |
| WO | 2015/006747 A2 | 1/2015 | |
| WO | 2015/099187 A1 | 7/2015 | |
| WO | WO-2015099187 A1 * | 7/2015 | ........... A61K 31/713 |
| WO | WO-2016080097 A1 * | 5/2016 | ......... A01K 67/0278 |
| WO | 2016/164356 A1 | 10/2016 | |
| WO | WO-2017053762 A1 * | 3/2017 | ............. C07K 16/40 |

OTHER PUBLICATIONS

Briner et al., "Guide RNA Functional Modules Direct Cas9 Activity and Orthogonality," *Mol. Cell*, 56(2): 333-339 and Supplemental Information Figures S1-S3, Tables S1-S2, and Experimental Procedures (2014).

(Continued)

*Primary Examiner* — Jane J Zara
(74) *Attorney, Agent, or Firm* — Leydig, Voit & Mayer, Ltd.

(57) ABSTRACT

The invention provides an artificial sgRNA and a CRISPR/Cas9 system by combining the artificial sgRNA and Cas9. Activity of the sgRNA can be retained even when a nucleotide linker region for forming a single strand by linking the 3'-terminal of crRNA and the 5'-terminal of tracrRNA in sgRNA is substituted with an amino acid derivative linker, when the linker region existing between stem-loop 1 and stem-loop 2 of tracrRNA and/or the loop portion of stem-loop 2 are/is substituted with an amino acid derivative linker, or when an amino acid derivative linker is added/inserted into the vicinity of the 5'-terminal and/or the 3'-terminal of sgRNA. Stability in vivo can be improved by introducing one or more amino acid derivative linkers into the sgRNA.

21 Claims, 16 Drawing Sheets

Specification includes a Sequence Listing.

(56) References Cited

OTHER PUBLICATIONS

Nishimasu et al., "Crystal Structure of Cas9 in Complex with Guide RNA and Target DNA," *Cell*, 156: 935-949 and Supplemental Information S1-S8 (2014).
European Patent Office, Communication Pursuant to Rule 164(1) EPC [Supplementary Partial European Search Report] in European Patent Application No. 17744466.8 (dated Aug. 22, 2019).
ACS, "Benzenepropanamide, N-hydroxy-alpha-[(2-hydroxyacetyl)-amino]-," STN Registry No. 1103513-06-9 (Feb. 9, 2009).
Hendel et al., "Chemically modified guide RNAs enhance CRISPR-Cas genome editing in human primary cells," *Nat. Biotechnol.*, 33(9): 985-989 (2015).
Japanese Patent Office, International Search Report in International Patent Application No. PCT/JP2017/003251 (dated May 9, 2017).

\* cited by examiner (SEQ ID NO: 3)

each n = A, G, C, or U (independently)

(n)20 = a guide region of crRNA

SEQUENCE LISTING

```
<160> NUMBER OF SEQ ID NOS: 87

<210> SEQ ID NO 1
<211> LENGTH: 42
<212> TYPE: RNA
<213> ORGANISM: Artificial Sequence
<220> FEATURE:
<223> OTHER INFORMATION: Synthetic crRNA derived from Streptococcus
      pyogenes
<220> FEATURE:
<221> NAME/KEY: misc_feature
<222> LOCATION: (1)..(20)
<223> OTHER INFORMATION: Guide region of crRNA
<220> FEATURE:
<221> NAME/KEY: misc_feature
<222> LOCATION: (1)..(20)
<223> OTHER INFORMATION: Each gnh is independently a, g, c or u.

<400> SEQUENCE: 1
nnnnnnnnnn nnnnnnnnnn guuuuagagc uaugcuguuu ug                        42

<210> SEQ ID NO 2
<211> LENGTH: 69
<212> TYPE: RNA
<213> ORGANISM: Streptococcus pyogenes
<220> FEATURE:
<221> NAME/KEY: misc_feature
<222> LOCATION: (1)..(69)
<223> OTHER INFORMATION: tracrRNA derived from Streptococcus pyogenes

<400> SEQUENCE: 2
aaacagcaua gcaaguuaaa auaaggcuag uccguuauca acuugaaaaa guggcaccga     60
gucggugcu                                                             69

<210> SEQ ID NO 3
```

```
<211> LENGTH: 98
<212> TYPE: RNA
<213> ORGANISM: Artificial Sequence
<220> FEATURE:
<223> OTHER INFORMATION: Synthetic sgRNA derived from Streptococcus
      pyogenes
<220> FEATURE:
<221> NAME/KEY: misc_feature
<222> LOCATION: (1)..(20)
<223> OTHER INFORMATION: Guide region of sgRNA
<220> FEATURE:
<221> NAME/KEY: misc_feature
<222> LOCATION: (1)..(20)
<223> OTHER INFORMATION: Each gnh is independently a, g, c or u.

<400> SEQUENCE: 3
nnnnnnnnnn nnnnnnnnnn guuuuagagc uagaaauagc aaguuaaaau aaggcuaguc    60
cguuaucaac uugaaaaagu ggcaccgagu cggugcuuu                          98

<210> SEQ ID NO 4
<211> LENGTH: 99
<212> TYPE: RNA
<213> ORGANISM: Artificial Sequence
<220> FEATURE:
<223> OTHER INFORMATION: Synthetic sgRNA SG-0001 specifically binding
      to human KRAS gene

<400> SEQUENCE: 4
guaguuggag cuguuggcgu guuuuagagc uagaaauagc aaguuaaaau aaggcuaguc    60
cguuaucaac uugaaaaagu ggcaccgagu cggugcuuu                          99

<210> SEQ ID NO 5
<211> LENGTH: 95
<212> TYPE: RNA
<213> ORGANISM: Artificial Sequence
<220> FEATURE:
<223> OTHER INFORMATION: Synthetic modified sgRNA SG-0002 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.

<400> SEQUENCE: 5
guaguuggag cuguuggcgu guuuuagagc uauagcaagu uaaaauaagg cuaguccguu    60
aucaacuuga aaaaguggca ccgagucggu gcuuu                              95

<210> SEQ ID NO 6
<211> LENGTH: 95
<212> TYPE: RNA
<213> ORGANISM: Artificial Sequence
<220> FEATURE:
<223> OTHER INFORMATION: Synthetic modified sgRNA SG-0012 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      lysine derivative linker.

<400> SEQUENCE: 6
guaguuggag cuguuggcgu guuuuagagc uauagcaagu uaaaauaagg cuaguccguu    60
aucaacuuga aaaaguggca ccgagucggu gcuuu                              95

<210> SEQ ID NO 7
<211> LENGTH: 95
```

```
<212> TYPE: RNA
<213> ORGANISM: Artificial Sequence
<220> FEATURE:
<223> OTHER INFORMATION: Synthetic modified sgRNA SG-0013 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glycylglycine derivative linker.

<400> SEQUENCE: 7
guaguuggag cuguuggcgu guuuuagagc uauagcaagu uaaaauaagg cuaguccguu    60
aucaacuuga aaaguggca ccgagucggu gcuuu                                95

<210> SEQ ID NO 8
<211> LENGTH: 91
<212> TYPE: RNA
<213> ORGANISM: Artificial Sequence
<220> FEATURE:
<223> OTHER INFORMATION: Synthetic modified sgRNA SG-0014 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (68)..(69)
<223> OTHER INFORMATION: The 68th "u" and the 69th "a" are linked via
      proline derivative linker.

<400> SEQUENCE: 8
guaguuggag cuguuggcgu guuuuagagc uauagcaagu uaaaauaagg cuaguccguu    60
aucaacuuaa guggcaccga gucggugcuu u                                   91

<210> SEQ ID NO 9
<211> LENGTH: 86
<212> TYPE: RNA
<213> ORGANISM: Artificial Sequence
<220> FEATURE:
<223> OTHER INFORMATION: Synthetic modified sgRNA SG-0015 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glycylglycine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 9
guaguuggag cuguuggcgu guuuuagagc uauagcaagu uaaaauaagg cuaguccgaa    60
cuuaaguggc accgagucgg ugcuuu                                         86

<210> SEQ ID NO 10
<211> LENGTH: 94
<212> TYPE: RNA
<213> ORGANISM: Artificial Sequence
<220> FEATURE:
<223> OTHER INFORMATION: Synthetic modified sgRNA SG-0016 specifically
```

-continued binding to human KRAS gene
<220> FEATURE:
<221> NAME/KEY: misc_feature
<222> LOCATION: (1)..(1)
<223> OTHER INFORMATION: The 1st "g" is modified with proline
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      proline derivative linker.

<400> SEQUENCE: 10
guaguuggag cguuggcgu guuuuagagc uauagcaagu aaaauaagg cuaguccguu    60 aucaacuuga aaaaguggca ccgagucggu gcuu                              94

<210> SEQ ID NO 11
<211> LENGTH: 99
<212> TYPE: RNA
<213> ORGANISM: Artificial Sequence
<220> FEATURE:
<223> OTHER INFORMATION: Synthetic sgRNA SG-0017 specifically binding
      to human BCL-2 gene

<400> SEQUENCE: 11
aagcgucccc gcgcggugaa guuuuagagc uagaaauagc aaguuaaaau aaggcuaguc    60
cguuaucaac uugaaaaagu ggcaccgagu cggugcuuu                          99

<210> SEQ ID NO 12
<211> LENGTH: 95
<212> TYPE: RNA
<213> ORGANISM: Artificial Sequence
<220> FEATURE:
<223> OTHER INFORMATION: Synthetic modified sgRNA SG-0018 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.

<400> SEQUENCE: 12
aagcgucccc gcgcggugaa guuuuagagc uauagcaagu aaaauaagg cuaguccguu    60 aucaacuuga aaaaguggca ccgagucggu gcuuu                              95

<210> SEQ ID NO 13
<211> LENGTH: 95
<212> TYPE: RNA
<213> ORGANISM: Artificial Sequence
<220> FEATURE:
<223> OTHER INFORMATION: Synthetic modified sgRNA SG-0019 specifically
      binding to human BCL-2 gene
<220> FEATURE:
<221> NAME/KEY: misc_feature
<223> OTHER INFORMATION: The 32nd "a" and the 33rd "u" are linked via
      lysine derivative linker.

<400> SEQUENCE: 13
aagcgucccc gcgcggugaa guuuuagagc uauagcaagu aaaauaagg cuaguccguu    60 aucaacuuga aaaaguggca ccgagucggu gcuuu                              95

<210> SEQ ID NO 14

```
<211> LENGTH: 95
<212> TYPE: RNA
<213> ORGANISM: Artificial Sequence
<220> FEATURE:
<223> OTHER INFORMATION: Synthetic modified sgRNA SG-0020 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      glycylglycine derivative linker.

<400> SEQUENCE: 14 aagcguccccc gcgcggugaa guuuuagagc uauagcaagu uaaaauaagg cuaguccguu      60
aucaacuuga aaaguggca ccgagucggu gcuuu                                   95

<210> SEQ ID NO 15
<211> LENGTH: 91
<212> TYPE: RNA
<213> ORGANISM: Artificial Sequence
<220> FEATURE:
<223> OTHER INFORMATION: Synthetic modified sgRNA SG-0021 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (68)..(69)
<223> OTHER INFORMATION: The 68th "u" and the 69th "a" are linked via
      proline derivative linker.

<400> SEQUENCE: 15 aagcguccccc gcgcggugaa guuuuagagc uauagcaagu uaaaauaagg cuaguccguu      60
aucaacuuaa guggcaccga gucggugcuu u                                      91

<210> SEQ ID NO 16
<211> LENGTH: 86
<212> TYPE: RNA
<213> ORGANISM: Artificial Sequence
<220> FEATURE:
<223> OTHER INFORMATION: Synthetic modified sgRNA SG-0022 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glycylglycine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 16 aagcguccccc gcgcggugaa guuuuagagc uauagcaagu uaaaauaagg cuaguccgaa      60
cuuaaguggc accgagucgg ugcuuu                                            86

<210> SEQ ID NO 17
<211> LENGTH: 94
<212> TYPE: RNA
<213> ORGANISM: Artificial Sequence
<220> FEATURE:
```

```
<223> OTHER INFORMATION: Synthetic modified sgRNA SG-0023 specifically
      binding to human BCL-2 gene
<220> FEATURE:
<221> NAME/KEY: misc_feature
<222> LOCATION: (1)..(1)
<223> OTHER INFORMATION: The 1st "a" is modified with proline
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      proline derivative linker.

<400> SEQUENCE: 17 aagcguccce gcgcggugaa guuuuagagc uauagcaagu uaaaauaagg cuaguccguu    60
aucaacuuga aaaguggca ccgagucggu gcuu                                 94

<210> SEQ ID NO 18
<211> LENGTH: 95
<212> TYPE: RNA
<213> ORGANISM: Artificial Sequence
<220> FEATURE:
<223> OTHER INFORMATION: Synthetic modified sgRNA SG-0024 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative (P13) linker.

<400> SEQUENCE: 18
guaguuggag cguuggcgu guuuuagagc uauagcaagu uaaaauaagg cuaguccguu    60
aucaacuuga aaaguggca ccgagucggu gcuuu                                95

<210> SEQ ID NO 19
<211> LENGTH: 95
<212> TYPE: RNA
<213> ORGANISM: Artificial Sequence
<220> FEATURE:
<223> OTHER INFORMATION: Synthetic modified sgRNA SG-0025 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative (P14) linker.

<400> SEQUENCE: 19
guaguuggag cguuggcgu guuuuagagc uauagcaagu uaaaauaagg cuaguccguu    60
aucaacuuga aaaguggca ccgagucggu gcuuu                                95

<210> SEQ ID NO 20
<211> LENGTH: 95
<212> TYPE: RNA
<213> ORGANISM: Artificial Sequence
<220> FEATURE:
<223> OTHER INFORMATION: Synthetic modified sgRNA SG-0026 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative (P15) linker.

<400> SEQUENCE: 20
```
guaguuggag cuguuggcgu guuuuagagc uauagcaagu uaaaauaagg cuaguccguu    60
aucaacuuga aaaaguggca ccgagucggu gcuuu                              95

<210> SEQ ID NO 21
<211> LENGTH: 95
<212> TYPE: RNA
<213> ORGANISM: Artificial Sequence
<220> FEATURE:
<223> OTHER INFORMATION: Synthetic modified sgRNA SG-0027 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      phenylalanine derivative linker.

<400> SEQUENCE: 21
guaguuggag cuguuggcgu guuuuagagc uauagcaagu uaaaauaagg cuaguccguu    60
aucaacuuga aaaaguggca ccgagucggu gcuuu                              95

<210> SEQ ID NO 22
<211> LENGTH: 95
<212> TYPE: RNA
<213> ORGANISM: Artificial Sequence
<220> FEATURE:
<223> OTHER INFORMATION: Synthetic modified sgRNA SG-0028 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      leucine derivative linker.

<400> SEQUENCE: 22
guaguuggag cuguuggcgu guuuuagagc uauagcaagu uaaaauaagg cuaguccguu    60
aucaacuuga aaaaguggca ccgagucggu gcuuu                              95

<210> SEQ ID NO 23
<211> LENGTH: 95
<212> TYPE: RNA
<213> ORGANISM: Artificial Sequence
<220> FEATURE:
<223> OTHER INFORMATION: Synthetic modified sgRNA SG-0029 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glutamic acid derivative linker.

<400> SEQUENCE: 23
guaguuggag cuguuggcgu guuuuagagc uauagcaagu uaaaauaagg cuaguccguu    60
aucaacuuga aaaaguggca ccgagucggu gcuuu                              95

<210> SEQ ID NO 24
<211> LENGTH: 86
<212> TYPE: RNA
<213> ORGANISM: Artificial Sequence
<220> FEATURE:
<223> OTHER INFORMATION: Synthetic modified sgRNA SG-0030 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:

```
<221> NAME/KEY: misc_feature
<222> LOCATION: (58)..(59)
<223> OTHER INFORMATION: The 58th "g" and the 59th "a" are linked via
      proline derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 24
guaguuggag cguuggcgu guuuuagagc uauagcaagu uaaaauaagg cuaguccgaa      60
cuuaaguggc accgagucgg ugcuuu                                         86

<210> SEQ ID NO 25
<211> LENGTH: 86
<212> TYPE: RNA
<213> ORGANISM: Artificial Sequence
<220> FEATURE:
<223> OTHER INFORMATION: Synthetic modified sgRNA SG-0031 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P13) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 25
guaguuggag cguuggcgu guuuuagagc uauagcaagu uaaaauaagg cuaguccgaa      60
cuuaaguggc accgagucgg ugcuuu                                         86

<210> SEQ ID NO 26
<211> LENGTH: 86
<212> TYPE: RNA
<213> ORGANISM: Artificial Sequence
<220> FEATURE:
<223> OTHER INFORMATION: Synthetic modified sgRNA SG-0032 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P14) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 26
guaguuggag cguuggcgu guuuuagagc uauagcaagu uaaaauaagg cuaguccgaa      60
cuuaaguggc accgagucgg ugcuuu                                         86

<210> SEQ ID NO 27
<211> LENGTH: 86
```

```
<212> TYPE: RNA
<213> ORGANISM: Artificial Sequence
<220> FEATURE:
<223> OTHER INFORMATION: Synthetic modified sgRNA SG-0033 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P15) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 27
guaguuggag cguuggcgu guuuuagagc uauagcaagu uaaaauaagg cuaguccgaa      60
cuuaaguggc accgagucgg ugcuuu                                          86

<210> SEQ ID NO 28
<211> LENGTH: 86
<212> TYPE: RNA
<213> ORGANISM: Artificial Sequence
<220> FEATURE:
<223> OTHER INFORMATION: Synthetic modified sgRNA SG-0034 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      phenylalanine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 28
guaguuggag cguuggcgu guuuuagagc uauagcaagu uaaaauaagg cuaguccgaa      60
cuuaaguggc accgagucgg ugcuuu                                          86

<210> SEQ ID NO 29
<211> LENGTH: 86
<212> TYPE: RNA
<213> ORGANISM: Artificial Sequence
<220> FEATURE:
<223> OTHER INFORMATION: Synthetic modified sgRNA SG-0035 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      leucine derivative linker.
<220> FEATURE:
<221> NAME/KEY: misc_feature
<222> LOCATION: (63)..(64)
<223> OTHER INFORMATION: The 63rd "u" and the 64th "a" are linked via
```

```
        proline derivative linker.

<400> SEQUENCE: 29
guaguuggag cguuggcgu guuuuagagc uauagcaagu uaaaauaagg cuaguccgaa    60
cuuaaguggc accgagucgg ugcuuu                                       86

<210> SEQ ID NO 30
<211> LENGTH: 86
<212> TYPE: RNA
<213> ORGANISM: Artificial Sequence
<220> FEATURE:
<223> OTHER INFORMATION: Synthetic modified sgRNA SG-0036 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glutamic acid derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 30
guaguuggag cguuggcgu guuuuagagc uauagcaagu uaaaauaagg cuaguccgaa    60
cuuaaguggc accgagucgg ugcuuu                                       86

<210> SEQ ID NO 31
<211> LENGTH: 95
<212> TYPE: RNA
<213> ORGANISM: Artificial Sequence
<220> FEATURE:
<223> OTHER INFORMATION: Synthetic modified sgRNA SG-0050 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glycine derivative linker.

<400> SEQUENCE: 31
guaguuggag cguuggcgu guuuuagagc uauagcaagu uaaaauaagg cuaguccguu    60
aucaacuuga aaaguggca ccgagucggu gcuuu                              95

<210> SEQ ID NO 32
<211> LENGTH: 95
<212> TYPE: RNA
<213> ORGANISM: Artificial Sequence
<220> FEATURE:
<223> OTHER INFORMATION: Synthetic modified sgRNA SG-0051 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      terephthalic acid derivative linker.

<400> SEQUENCE: 32
guaguuggag cguuggcgu guuuuagagc uauagcaagu uaaaauaagg cuaguccguu    60
aucaacuuga aaaguggca ccgagucggu gcuuu                              95
```

```
<210> SEQ ID NO 33
<211> LENGTH: 86
<212> TYPE: RNA
<213> ORGANISM: Artificial Sequence
<220> FEATURE:
<223> OTHER INFORMATION: Synthetic modified sgRNA SG-0052 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glycine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 33
guaguuggag cuguuggcgu guuuuagagc uauagcaagu uaaaauaagg cuaguccgaa      60
cuuaaguggc accgagucgg ugcuuu                                          86

<210> SEQ ID NO 34
<211> LENGTH: 86
<212> TYPE: RNA
<213> ORGANISM: Artificial Sequence
<220> FEATURE:
<223> OTHER INFORMATION: Synthetic modified sgRNA SG-0053 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      terephthalic acid derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 34
guaguuggag cuguuggcgu guuuuagagc uauagcaagu uaaaauaagg cuaguccgaa      60
cuuaaguggc accgagucgg ugcuuu                                          86

<210> SEQ ID NO 35
<211> LENGTH: 91
<212> TYPE: RNA
<213> ORGANISM: Artificial Sequence
<220> FEATURE:
<223> OTHER INFORMATION: Synthetic modified sgRNA SG-0075 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      lysine derivative linker.
<220> FEATURE:
<221> NAME/KEY: misc_feature
<222> LOCATION: (68)..(69)
<223> OTHER INFORMATION: The 68th "u" and the 69th "a" are linked via
      lysine derivative linker.

<400> SEQUENCE: 35
```
guaguuggag cuguuggcgu guuuuagagc uauagcaagu uaaaauaagg cuaguccguu    60
aucaacuuaa guggcaccga gucggugcuu u    91

<210> SEQ ID NO 36
<211> LENGTH: 91
<212> TYPE: RNA
<213> ORGANISM: Artificial Sequence
<220> FEATURE:
<223> OTHER INFORMATION: Synthetic modified sgRNA SG-0076 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glycylglycine derivative linker.
<220> FEATURE:
<221> NAME/KEY: misc_feature
<222> LOCATION: (68)..(69)
<223> OTHER INFORMATION: The 68th "u" and the 69th "a" are linked via
      glycylglycine derivative linker.

<400> SEQUENCE: 36
guaguuggag cuguuggcgu guuuuagagc uauagcaagu uaaaauaagg cuaguccguu    60
aucaacuuaa guggcaccga gucggugcuu u    91

<210> SEQ ID NO 37
<211> LENGTH: 91
<212> TYPE: RNA
<213> ORGANISM: Artificial Sequence
<220> FEATURE:
<223> OTHER INFORMATION: Synthetic modified sgRNA SG-0077 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glycine derivative linker.
<220> FEATURE:
<221> NAME/KEY: misc_feature
<222> LOCATION: (68)..(69)
<223> OTHER INFORMATION: The 68th "u" and the 69th "a" are linked via
      glycine derivative linker.

<400> SEQUENCE: 37
guaguuggag cuguuggcgu guuuuagagc uauagcaagu uaaaauaagg cuaguccguu    60
aucaacuuaa guggcaccga gucggugcuu u    91

<210> SEQ ID NO 38
<211> LENGTH: 91
<212> TYPE: RNA
<213> ORGANISM: Artificial Sequence
<220> FEATURE:
<223> OTHER INFORMATION: Synthetic modified sgRNA SG-0078 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      terephthalic acid derivative linker.
<220> FEATURE:
<221> NAME/KEY: misc_feature
<222> LOCATION: (68)..(69)
<223> OTHER INFORMATION: The 68th "u" and the 69th "a" are linked via
      terephthalic acid derivative linker.

<400> SEQUENCE: 38
guaguuggag cuguuggcgu guuuuagagc uauagcaagu uaaaauaagg cuaguccguu    60
aucaacuuaa guggcaccga gucggugcuu u    91

```
<210> SEQ ID NO 39
<211> LENGTH: 91
<212> TYPE: RNA
<213> ORGANISM: Artificial Sequence
<220> FEATURE:
<223> OTHER INFORMATION: Synthetic modified sgRNA SG-0079 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      phenylalanine derivative linker.
<220> FEATURE:
<221> NAME/KEY: misc_feature
<222> LOCATION: (68)..(69)
<223> OTHER INFORMATION: The 68th "u" and the 69th "a" are linked via
      phenylalanine derivative linker.

<400> SEQUENCE: 39
guaguuggag cguuggcgu guuuuagagc uauagcaagu uaaaauaagg cuaguccguu      60
aucaacuuaa guggcaccga gucggugcuu u                                   91

<210> SEQ ID NO 40
<211> LENGTH: 91
<212> TYPE: RNA
<213> ORGANISM: Artificial Sequence
<220> FEATURE:
<223> OTHER INFORMATION: Synthetic modified sgRNA SG-0080 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      leucine derivative linker.
<220> FEATURE:
<221> NAME/KEY: misc_feature
<222> LOCATION: (68)..(69)
<223> OTHER INFORMATION: The 68th "u" and the 69th "a" are linked via
      leucine derivative linker.

<400> SEQUENCE: 40
guaguuggag cguuggcgu guuuuagagc uauagcaagu uaaaauaagg cuaguccguu      60
aucaacuuaa guggcaccga gucggugcuu u                                   91

<210> SEQ ID NO 41
<211> LENGTH: 91
<212> TYPE: RNA
<213> ORGANISM: Artificial Sequence
<220> FEATURE:
<223> OTHER INFORMATION: Synthetic modified sgRNA SG-0081 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      glutamic acid derivative linker.
<220> FEATURE:
<221> NAME/KEY: misc_feature
<222> LOCATION: (68)..(69)
<223> OTHER INFORMATION: The 68th "u" and the 69th "a" are linked via
      glutamic acid derivative linker.

<400> SEQUENCE: 41
guaguuggag cguuggcgu guuuuagagc uauagcaagu uaaaauaagg cuaguccguu      60
aucaacuuaa guggcaccga gucggugcuu u                                   91

<210> SEQ ID NO 42
<211> LENGTH: 86
```

```
<212> TYPE: RNA
<213> ORGANISM: Artificial Sequence
<220> FEATURE:
<223> OTHER INFORMATION: Synthetic modified sgRNA SG-0082 specifically
      binding to human KRAS gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      lysine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 42
guaguuggag cguuggcgu guuuuagagc uauagcaagu aaaauaagg cuaguccgaa    60 cuuaaguggc accgagucgg ugcuuu                                       86

<210> SEQ ID NO 43
<211> LENGTH: 94
<212> TYPE: RNA
<213> ORGANISM: Artificial Sequence
<220> FEATURE:
<223> OTHER INFORMATION: Synthetic modified sgRNA SG-0083 specifically
      binding to human KRAS gene
<220> FEATURE:
<221> NAME/KEY: misc_feature
<222> LOCATION: (1)..(1)
<223> OTHER INFORMATION: The 1st "g" is modified with lysine derivative
      linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      lysine derivative linker.

<400> SEQUENCE: 43
guaguuggag cguuggcgu guuuuagagc uauagcaagu aaaauaagg cuaguccguu    60 aucaacuuga aaaaguggca ccgagucggu gcuu                              94

<210> SEQ ID NO 44
<211> LENGTH: 94
<212> TYPE: RNA
<213> ORGANISM: Artificial Sequence
<220> FEATURE:
<223> OTHER INFORMATION: Synthetic modified sgRNA SG-0084 specifically
      binding to human KRAS gene
<220> FEATURE:
<221> NAME/KEY: misc_feature
<222> LOCATION: (1)..(1)
<223> OTHER INFORMATION: The 1st "g" is modified with glycylglycine
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
``` glycylglycine derivative linker.

<400> SEQUENCE: 44
guaguuggag cguuggcgu guuuuagagc uauagcaagu uaaaauaagg cuaguccguu    60
aucaacuuga aaaguggca ccgagucggu gcuu    94

<210> SEQ ID NO 45
<211> LENGTH: 94
<212> TYPE: RNA
<213> ORGANISM: Artificial Sequence
<220> FEATURE:
<223> OTHER INFORMATION: Synthetic modified sgRNA SG-0085 specifically
      binding to human KRAS gene
<220> FEATURE:
<221> NAME/KEY: misc_feature
<222> LOCATION: (1)..(1)
<223> OTHER INFORMATION: The 1st "g" is modified with glycine
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      glycine derivative linker.

<400> SEQUENCE: 45
guaguuggag cguuggcgu guuuuagagc uauagcaagu uaaaauaagg cuaguccguu    60
aucaacuuga aaaguggca ccgagucggu gcuu    94

<210> SEQ ID NO 46
<211> LENGTH: 94
<212> TYPE: RNA
<213> ORGANISM: Artificial Sequence
<220> FEATURE:
<223> OTHER INFORMATION: Synthetic modified sgRNA SG-0086 specifically
      binding to human KRAS gene
<220> FEATURE:
<221> NAME/KEY: misc_feature
<222> LOCATION: (1)..(1)
<223> OTHER INFORMATION: The 1st "g" is modified with terephthalic acid
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      terephthalic acid derivative linker.

<400> SEQUENCE: 46
guaguuggag cguuggcgu guuuuagagc uauagcaagu uaaaauaagg cuaguccguu    60
aucaacuuga aaaguggca ccgagucggu gcuu    94

<210> SEQ ID NO 47
<211> LENGTH: 94
<212> TYPE: RNA
<213> ORGANISM: Artificial Sequence
<220> FEATURE:
<223> OTHER INFORMATION: Synthetic modified sgRNA SG-0087 specifically
      binding to human KRAS gene
<220> FEATURE:
<221> NAME/KEY: misc_feature
<222> LOCATION: (1)..(1)

```
<223> OTHER INFORMATION: The 1st "a" is modified with phenylalanine
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      phenylalanine derivative linker.

<400> SEQUENCE: 47
guaguuggag cguuuggcgu guuuuagagc uauagcaagu uaaaauaagg cuaguccguu       60
aucaacuuga aaaaguggca ccgagucggu gcuu                                  94

<210> SEQ ID NO 48
<211> LENGTH: 94
<212> TYPE: RNA
<213> ORGANISM: Artificial Sequence
<220> FEATURE:
<223> OTHER INFORMATION: Synthetic modified sgRNA SG-0088 specifically
      binding to human KRAS gene
<220> FEATURE:
<221> NAME/KEY: misc_feature
<222> LOCATION: (1)..(1)
<223> OTHER INFORMATION: The 1st "g" is modified with leucine
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      leucine derivative linker.

<400> SEQUENCE: 48
guaguuggag cguuuggcgu guuuuagagc uauagcaagu uaaaauaagg cuaguccguu       60
aucaacuuga aaaaguggca ccgagucggu gcuu                                  94

<210> SEQ ID NO 49
<211> LENGTH: 94
<212> TYPE: RNA
<213> ORGANISM: Artificial Sequence
<220> FEATURE:
<223> OTHER INFORMATION: Synthetic modified sgRNA SG-0089 specifically
      binding to human KRAS gene
<220> FEATURE:
<221> NAME/KEY: misc_feature
<222> LOCATION: (1)..(1)
<223> OTHER INFORMATION: The 1st "g" is modified with glutamic acid
      derivative linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (93)..(94)
<223> OTHER INFORMATION: The 93rd "u" and the 94th "u" are linked via
      glutamic acid derivative linker.

<400> SEQUENCE: 49
guaguuggag cguuuggcgu guuuuagagc uauagcaagu uaaaauaagg cuaguccguu       60
aucaacuuga aaaaguggca ccgagucggu gcuu                                  94
```

<210> SEQ ID NO 50
<211> LENGTH: 62
<212> TYPE: RNA
<213> ORGANISM: Artificial Sequence
<220> FEATURE:
<223> OTHER INFORMATION: Synthetic modified sgRNA SG-0004 specifically
      binding to human KRAS gene

<400> SEQUENCE: 50
guaguuggag cguuggcgu guuuuagagc uagaaauagc aaguuaaaau aaggcuaguc    60
cg                                                                  62

<210> SEQ ID NO 51
<211> LENGTH: 80
<212> TYPE: RNA
<213> ORGANISM: Artificial Sequence
<220> FEATURE:
<223> OTHER INFORMATION: Synthetic modified sgRNA SG-0054 specifically
      binding to human KRAS gene

<400> SEQUENCE: 51
guaguuggag cguuggcgu guuuuagagc uagaaauagc aaguuaaaau aaggcuaguc    60
cguuaucaac uugaaaaagu                                               80

<210> SEQ ID NO 52
<211> LENGTH: 55
<212> TYPE: RNA
<213> ORGANISM: Artificial Sequence
<220> FEATURE:
<223> OTHER INFORMATION: Synthetic modified sgRNA SG-0055 specifically
      binding to human KRAS gene

<400> SEQUENCE: 52
guaguuggag cguuggcgu guuuuagagc uagaaauagc aaguuaaaau aaggc         55

<210> SEQ ID NO 53
<211> LENGTH: 50
<212> TYPE: RNA
<213> ORGANISM: Artificial Sequence
<220> FEATURE:
<223> OTHER INFORMATION: Synthetic modified sgRNA SG-0056 specifically
      binding to human KRAS gene

<400> SEQUENCE: 53
guaguuggag cguuggcgu guuuuagagc uagaaauagc aaguuaaaau              50

<210> SEQ ID NO 54
<211> LENGTH: 45
<212> TYPE: RNA
<213> ORGANISM: Artificial Sequence
<220> FEATURE:
<223> OTHER INFORMATION: Synthetic modified sgRNA SG-0057 specifically
      binding to human KRAS gene

<400> SEQUENCE: 54
guaguuggag cguuggcgu guuuuagagc uagaaauagc aaguu                   45

<210> SEQ ID NO 55
<211> LENGTH: 97
<212> TYPE: RNA
<213> ORGANISM: Artificial Sequence
<220> FEATURE:
<223> OTHER INFORMATION: Synthetic modified sgRNA SG-0058 specifically
      binding to human KRAS gene
<220> FEATURE:
<221> NAME/KEY: misc_feature

```
<222> LOCATION: (55)..(56)
<223> OTHER INFORMATION: The 55th "c" and the 56th "g" are linked via
      proline derivative linker.

<400> SEQUENCE: 55
guaguuggag cuguuggcgu guuuuagagc uagaaauagc aaguuaaaau aaggcguccg      60
uuaucaacuu gaaaaagugg caccgagucg gugcuuu                              97

<210> SEQ ID NO 56
<211> LENGTH: 96
<212> TYPE: RNA
<213> ORGANISM: Artificial Sequence
<220> FEATURE:
<223> OTHER INFORMATION: Synthetic modified sgRNA SG-0059 specifically
      binding to human KRAS gene
<220> FEATURE:
<221> NAME/KEY: misc_feature
<222> LOCATION: (87)..(88)
<223> OTHER INFORMATION: The 87th "g" and the 88th "c" are linked via
      proline derivative linker.

<400> SEQUENCE: 56
guaguuggag cuguuggcgu guuuuagagc uagaaauagc aaguuaaaau aaggcuaguc      60
cguuaucaac uugaaaaagu ggcaccgcgg ugcuuu                               96

<210> SEQ ID NO 57
<211> LENGTH: 89
<212> TYPE: RNA
<213> ORGANISM: Artificial Sequence
<220> FEATURE:
<223> OTHER INFORMATION: Synthetic modified sgRNA SG-0060 specifically
      binding to human KRAS gene
<220> FEATURE:
<221> NAME/KEY: misc_feature
<222> LOCATION: (29)..(30)
<223> OTHER INFORMATION: The 29th "g" and the 30th "c" are linked via
      proline derivative linker.

<400> SEQUENCE: 57
guaguuggag cuguuggcgu guuuuagagc aaguuaaaau aaggcuaguc cguuaucaac      60
uugaaaaagu ggcaccgagu cggugcuuu                                       89

<210> SEQ ID NO 58
<211> LENGTH: 87
<212> TYPE: RNA
<213> ORGANISM: Artificial Sequence
<220> FEATURE:
<223> OTHER INFORMATION: Synthetic modified sgRNA SG-0061 specifically
      binding to human KRAS gene
<220> FEATURE:
<221> NAME/KEY: misc_feature
<222> LOCATION: (68)..(69)
<223> OTHER INFORMATION: The 68th "a" and the 69th "g" are linked via
      proline derivative linker.

<400> SEQUENCE: 58
guaguuggag cuguuggcgu guuuuagagc uagaaauagc aaguuaaaau aaggcuaguc      60
cguuaucagg caccgagucg gugcuuu                                         87

<210> SEQ ID NO 59
<211> LENGTH: 72
<212> TYPE: RNA
<213> ORGANISM: Artificial Sequence
<220> FEATURE:
<223> OTHER INFORMATION: Synthetic modified sgRNA SG-0062 specifically
      binding to human KRAS gene
<220> FEATURE:
```

```
<221> NAME/KEY: misc_feature
<222> LOCATION: (29)..(30)
<223> OTHER INFORMATION: The 29th "g" and the 30th "c" are linked via
      proline derivative linker.
<220> FEATURE:
<221> NAME/KEY: misc_feature
<222> LOCATION: (52)..(53)
<223> OTHER INFORMATION: The 52nd "g" and the 53rd "a" are linked via
      proline derivative linker.
<220> FEATURE:
<221> NAME/KEY: misc_feature
<222> LOCATION: (53)..(54)
<223> OTHER INFORMATION: The 53rd "a" and the 54th "g" are linked via
      proline derivative linker.

<400> SEQUENCE: 59
guaguuggag cguuggcgu guuuuagagc aaguuaaaau aaggcuaguc cgaggcaccg    60
agucggugcu uu                                                      72

<210> SEQ ID NO 60
<211> LENGTH: 95
<212> TYPE: RNA
<213> ORGANISM: Artificial Sequence
<220> FEATURE:
<223> OTHER INFORMATION: Synthetic modified sgRNA SG-0037 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative (P13) linker.

<400> SEQUENCE: 60
aagcgucccc gcgcggugaa guuuuagagc uauagcaagu uaaaauaagg cuaguccguu    60
aucaacuuga aaaguggca ccgagucggu gcuuu                               95

<210> SEQ ID NO 61
<211> LENGTH: 95
<212> TYPE: RNA
<213> ORGANISM: Artificial Sequence
<220> FEATURE:
<223> OTHER INFORMATION: Synthetic modified sgRNA SG-0038 specifically
      binding to human BCL-2 gene
<220> FEATURE:
<221> NAME/KEY: misc_feature
<222> LOCATION: (352)..(33)
<223> OTHER INFORMATION: The 32nd "a" and the 33rd "u" are linked via
      proline derivative (P14) linker.

<400> SEQUENCE: 61
aagcgucccc gcgcggugaa guuuuagagc uauagcaagu uaaaauaagg cuaguccguu    60
aucaacuuga aaaguggca ccgagucggu gcuuu                               95

<210> SEQ ID NO 62
<211> LENGTH: 95
<212> TYPE: RNA
<213> ORGANISM: Artificial Sequence
<220> FEATURE:
<223> OTHER INFORMATION: Synthetic modified sgRNA SG-0039 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative (P15) linker.

<400> SEQUENCE: 62
aagcgucccc gcgcggugaa guuuuagagc uauagcaagu uaaaauaagg cuaguccguu    60
```
aucaacuuga aaaaguggca ccgagucggu gcuuu          95

<210> SEQ ID NO 63
<211> LENGTH: 95
<212> TYPE: RNA
<213> ORGANISM: Artificial Sequence
<220> FEATURE:
<223> OTHER INFORMATION: Synthetic modified sgRNA SG-0040 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      phenylalanine derivative linker.

<400> SEQUENCE: 63 aagcguccccc gcgcggugaa guuuuagagc uauagcaagu uaaaauaagg cuaguccguu          60
aucaacuuga aaaaguggca ccgagucggu gcuuu          95

<210> SEQ ID NO 64
<211> LENGTH: 95
<212> TYPE: RNA
<213> ORGANISM: Artificial Sequence
<220> FEATURE:
<223> OTHER INFORMATION: Synthetic modified sgRNA SG-0041 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      leucine derivative linker.

<400> SEQUENCE: 64 aagcguccccc gcgcggugaa guuuuagagc uauagcaagu uaaaauaagg cuaguccguu          60
aucaacuuga aaaaguggca ccgagucggu gcuuu          95

<210> SEQ ID NO 65
<211> LENGTH: 95
<212> TYPE: RNA
<213> ORGANISM: Artificial Sequence
<220> FEATURE:
<223> OTHER INFORMATION: Synthetic modified sgRNA SG-0042 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      glutamic acid derivative linker.

<400> SEQUENCE: 65 aagcguccccc gcgcggugaa guuuuagagc uauagcaagu uaaaauaagg cuaguccguu          60
aucaacuuga aaaaguggca ccgagucggu gcuuu          95

<210> SEQ ID NO 66
<211> LENGTH: 86
<212> TYPE: RNA
<213> ORGANISM: Artificial Sequence
<220> FEATURE:
<223> OTHER INFORMATION: Synthetic modified sgRNA SG-0043 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via -continued

```
      proline derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 66 aagcguccccc gcgcggugaa guuuuagagc uauagcaagu uaaaauaagg cuaguccgaa      60
cuuaaguggc accgagucgg ugcuuu                                            86

<210> SEQ ID NO 67
<211> LENGTH: 86
<212> TYPE: RNA
<213> ORGANISM: Artificial Sequence
<220> FEATURE:
<223> OTHER INFORMATION: Synthetic modified sgRNA SG-0044 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P13) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 67 aagcguccccc gcgcggugaa guuuuagagc uauagcaagu uaaaauaagg cuaguccgaa      60
cuuaaguggc accgagucgg ugcuuu                                            86

<210> SEQ ID NO 68
<211> LENGTH: 86
<212> TYPE: RNA
<213> ORGANISM: Artificial Sequence
<220> FEATURE:
<223> OTHER INFORMATION: Synthetic modified sgRNA SG-0045 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P14) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 68 aagcguccccc gcgcggugaa guuuuagagc uauagcaagu uaaaauaagg cuaguccgaa      60
cuuaaguggc accgagucgg ugcuuu                                            86

<210> SEQ ID NO 69
<211> LENGTH: 86
<212> TYPE: RNA
<213> ORGANISM: Artificial Sequence
<220> FEATURE:
```

<223> OTHER INFORMATION: Synthetic modified sgRNA SG-0046 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative (P15) linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 69 aagcguccccc gcgcggugaa guuuuagagc uauagcaagu uaaaauaagg cuaguccgaa       60
cuuaaguggc accgagucgg ugcuuu                                            86

<210> SEQ ID NO 70
<211> LENGTH: 86
<212> TYPE: RNA
<213> ORGANISM: Artificial Sequence
<220> FEATURE:
<223> OTHER INFORMATION: Synthetic modified sgRNA SG-0047 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      phenylalanine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 70 aagcguccccc gcgcggugaa guuuuagagc uauagcaagu uaaaauaagg cuaguccgaa       60
cuuaaguggc accgagucgg ugcuuu                                            86

<210> SEQ ID NO 71
<211> LENGTH: 86
<212> TYPE: RNA
<213> ORGANISM: Artificial Sequence
<220> FEATURE:
<223> OTHER INFORMATION: Synthetic modified sgRNA SG-0048 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      leucine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 71

```
aagcguccc  gcgcggugaa  guuuuagagc  uauagcaagu  uaaaauaagg  cuaguccgaa    60
cuuaagugcc  accgagucgg  ugcuuu                                            86

<210> SEQ ID NO 72
<211> LENGTH: 86
<212> TYPE: RNA
<213> ORGANISM: Artificial Sequence
<220> FEATURE:
<223> OTHER INFORMATION: Synthetic modified sgRNA SG-0049 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glutamic acid derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 72 aagcguccc  gcgcggugaa  guuuuagagc  uauagcaagu  uaaaauaagg  cuaguccgaa    60
cuuaagugcc  accgagucgg  ugcuuu                                            86

<210> SEQ ID NO 73
<211> LENGTH: 91
<212> TYPE: RNA
<213> ORGANISM: Artificial Sequence
<220> FEATURE:
<223> OTHER INFORMATION: Synthetic modified sgRNA SG-0063 specifically
      binding to human BCL-2 gene
<220> FEATURE:
<221> NAME/KEY: misc_feature
<222> LOCATION: (32)..(33)
<223> OTHER INFORMATION: The 32nd "a" and the 33rd "u" are linked via
      lysine derivative linker.
<220> FEATURE:
<221> NAME/KEY: misc_feature
<222> LOCATION: (68)..(69)
<223> OTHER INFORMATION: The 68th "u" and the 69th "a" are linked via
      lysine derivative linker.

<400> SEQUENCE: 73 aagcguccc  gcgcggugaa  guuuuagagc  uauagcaagu  uaaaauaagg  cuaguccguu    60
aucaacuuaa  guggcaccga  gucggugcuu  u                                    91

<210> SEQ ID NO 74
<211> LENGTH: 94
<212> TYPE: RNA
<213> ORGANISM: Artificial Sequence
<220> FEATURE:
<223> OTHER INFORMATION: Synthetic modified sgRNA SG-0064 specifically
      binding to human BCL-2 gene
<220> FEATURE:
<221> NAME/KEY: misc_feature
<222> LOCATION: (1)..(1)
<223> OTHER INFORMATION: The 1st "a" is modified with lysine derivative
      linker.
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
```

```
<221> NAME/KEY: misc_feature
<222> LOCATION: (93)..(94)
<223> OTHER INFORMATION: The 93rd "u" and the 94th "u" are linked via
      lysine derivative linker.

<400> SEQUENCE: 74 aagcguccccc gcgcggugaa guuuuagagc uauagcaagu uaaaauaagg cuaguccguu        60
aucaacuuga aaaguggca ccgagucggu gcuu                                     94

<210> SEQ ID NO 75
<211> LENGTH: 99
<212> TYPE: RNA
<213> ORGANISM: Artificial Sequence
<220> FEATURE:
<223> OTHER INFORMATION: Synthetic sgRNA SG-0090 specifically binding
      to human BRAF gene

<400> SEQUENCE: 75
uagcuacaga gaaaucucga guuuuagagc uagaaauagc aaguuaaaau aaggcuaguc        60
cguuaucaac uugaaaaagu ggcaccgagu cggugcuuu                               99

<210> SEQ ID NO 76
<211> LENGTH: 91
<212> TYPE: RNA
<213> ORGANISM: Artificial Sequence
<220> FEATURE:
<223> OTHER INFORMATION: Synthetic modified sgRNA SG-0093 specifically
      binding to human BRAF gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (68)..(69)
<223> OTHER INFORMATION: The 68th "u" and the 69th "a" are linked via
      proline derivative linker.

<400> SEQUENCE: 76
uagcuacaga gaaaucucga guuuuagagc uauagcaagu uaaaauaagg cuaguccguu        60
aucaacuuaa guggcaccga gucggugcuu u                                       91

<210> SEQ ID NO 77
<211> LENGTH: 95
<212> TYPE: RNA
<213> ORGANISM: Artificial Sequence
<220> FEATURE:
<223> OTHER INFORMATION: Synthetic modified sgRNA SG-0096 specifically
      binding to human BRAF gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.

<400> SEQUENCE: 77
uagcuacaga gaaaucucga guuuuagagc uauagcaagu uaaaauaagg cuaguccguu        60
aucaacuuga aaaguggca ccgagucggu gcuuu                                    95

<210> SEQ ID NO 78
<211> LENGTH: 95
<212> TYPE: RNA
<213> ORGANISM: Artificial Sequence
<220> FEATURE:
<223> OTHER INFORMATION: Synthetic modified sgRNA SG-0097 specifically
      binding to human BRAF gene
```

```
<220> FEATURE:
<221> NAME/KEY: misc_feature
<222> LOCATION: (32)..(33)
<223> OTHER INFORMATION: The 32nd "a" and the 33rd "u" are linked via
      lysine derivative linker.

<400> SEQUENCE: 78
uagcuacaga gaaaucucga guuuuagagc uauagcaagu uaaaauaagg cuaguccguu      60
aucaacuuga aaaguggca ccgagucggu gcuuu                                 95

<210> SEQ ID NO 79
<211> LENGTH: 86
<212> TYPE: RNA
<213> ORGANISM: Artificial Sequence
<220> FEATURE:
<223> OTHER INFORMATION: Synthetic modified sgRNA SG-0098 specifically
      binding to human BRAF gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      proline derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 79
uagcuacaga gaaaucucga guuuuagagc uauagcaagu uaaaauaagg cuaguccgaa      60
cuuaaguggc accgagucgg ugcuuu                                          86

<210> SEQ ID NO 80
<211> LENGTH: 86
<212> TYPE: RNA
<213> ORGANISM: Artificial Sequence
<220> FEATURE:
<223> OTHER INFORMATION: Synthetic modified sgRNA SG-0099 specifically
      binding to human BRAF gene
<220> FEATURE:
<221> NAME/KEY: misc_feature
<222> LOCATION: (32)..(33)
<223> OTHER INFORMATION: The 32nd "a" and the 33rd "u" are linked via
      proline derivative linker.
<220> FEATURE:
<221> NAME/KEY: misc_feature
<222> LOCATION: (58)..(59)
<223> OTHER INFORMATION: The 58th "g" and the 59th "a" are linked via
      glycylglycine derivative linker.
<220> FEATURE:
<221> NAME/KEY: misc_feature
<222> LOCATION: (63)..(64)
<223> OTHER INFORMATION: The 63rd "u" and the 64th "a" are linked via
      proline derivative linker.

<400> SEQUENCE: 80
uagcuacaga gaaaucucga guuuuagagc uauagcaagu uaaaauaagg cuaguccgaa      60
cuuaaguggc accgagucgg ugcuuu                                          86

<210> SEQ ID NO 81
<211> LENGTH: 92
<212> TYPE: RNA
<213> ORGANISM: Artificial Sequence
<220> FEATURE:
<223> OTHER INFORMATION: Synthetic modified sgRNA SG-0100 specifically
``` binding to human BRAF gene
<220> FEATURE:
<221> NAME/KEY: misc_feature
<222> LOCATION: (32)..(33)
<223> OTHER INFORMATION: The 32nd "a" and the 33rd "u" are linked via
    lysine derivative linker.
<220> FEATURE:
<221> NAME/KEY: misc_feature
<222> LOCATION: (68)..(69)
<223> OTHER INFORMATION: The 68th "u" and the 69th "a" are linked via
    lysine derivative linker.

<400> SEQUENCE: 81
uagcuacaga gaaaucucga guuuuagagc uauagcaagu uaaaauaagg cuagaccguu      60
aucaacuuka aguggcaccg agucggugcu uu                                    92

<210> SEQ ID NO 82
<211> LENGTH: 94
<212> TYPE: RNA
<213> ORGANISM: Artificial Sequence
<220> FEATURE:
<223> OTHER INFORMATION: Synthetic modified sgRNA SG-0101 specifically
    binding to human BRAF gene
<220> FEATURE:
<221> NAME/KEY: misc_feature
<222> LOCATION: (1)..(1)
<223> OTHER INFORMATION: The 1st "u" is modified with proline
    derivative linker.
<220> FEATURE:
<221> NAME/KEY: misc_feature
<222> LOCATION: (32)..(33)
<223> OTHER INFORMATION: The 32nd "a" and the 33rd "u" are linked via
    proline derivative linker.
<220> FEATURE:
<221> NAME/KEY: misc_feature
<222> LOCATION: (93)..(94)
<223> OTHER INFORMATION: The 93rd "u" and the 94th "u" are linked via
    proline derivative linker.

<400> SEQUENCE: 82
uagcuacaga gaaaucucga guuuuagagc uauagcaagu uaaaauaagg cuagaccguu      60
aucaacuuga aaaguggca ccgagucggu gcuu                                   94

<210> SEQ ID NO 83
<211> LENGTH: 94
<212> TYPE: RNA
<213> ORGANISM: Artificial Sequence
<220> FEATURE:
<223> OTHER INFORMATION: Synthetic modified sgRNA SG-0102 specifically
    binding to human BRAF gene
<220> FEATURE:
<221> NAME/KEY: misc_feature
<222> LOCATION: (1)..(1)
<223> OTHER INFORMATION: The 1st "u" is modified with lysine derivative
    linker.
<220> FEATURE:
<221> NAME/KEY: misc_feature
<222> LOCATION: (32)..(33)
<223> OTHER INFORMATION: The 32nd "a" and the 33rd "u" are linked via
    proline derivative linker.
<220> FEATURE:
<221> NAME/KEY: misc_feature
<222> LOCATION: (93)..(94)
<223> OTHER INFORMATION: The 93rd "u" and the 94th "u" are linked via
    lysine derivative linker.

```
<400> SEQUENCE: 83
uagcuacaga gaaaucucga guuuuagagc uauagcaagu uaaaauaagg cuaguccguu    60
aucaacuuga aaaaguggca ccgagucggu gcuu                                94

<210> SEQ ID NO 84
<211> LENGTH: 25
<212> TYPE: DNA
<213> ORGANISM: Artificial Sequence
<220> FEATURE:
<223> OTHER INFORMATION: Primer

<400> SEQUENCE: 84
atcaagtgtt ccgcgtgatt gaaga                                          25

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
ctcacatcac caagtgcacc taccc                                          25

<210> SEQ ID NO 86
<211> LENGTH: 25
<212> TYPE: DNA
<213> ORGANISM: Artificial Sequence
<220> FEATURE:
<223> OTHER INFORMATION: Primer

<400> SEQUENCE: 86
cgcccaggag tgccaagaga atatc                                          25

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
cagcagcatc tcagggccaa aaat                                           24
```

ARTIFICIAL SINGLE GUIDE RNA AND USE THEREOF

CROSS-REFERENCE TO RELATED APPLICATIONS

This patent application is the U.S. national phase of International Patent Application No. PCT/JP2017/003251, filed Jan. 30, 2017, which claims the benefit of Japanese Patent Application No. 2016-016743, filed on Jan. 30, 2016, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 49,572 bytes ASCII (Text) file named "740058Replacement-SequenceListing-2nd.txt," created Dec. 30, 2018.

TECHNICAL FIELD

The present invention relates to an artificial single guide RNA (hereinafter to be also referred to as "sgRNA") having an activity equal to or more than that of a natural form and improved in vivo stability, CRISPR/Cas9 system consisting of a combination of the artificial sgRNA and CRISPR-associated protein 9 (Cas9), and use thereof.

Background Art

CRISPR (clustered regularly interspaced short palindromic repeats) is a short repetitive sequence of several tens of base pairs present in bacteria and is involved in the acquired immune mechanism against foreign DNA such as bacteriophage, plasmid and the like. One of the Cas gene cluster upstream of CRISPR recognizes a specific short sequence called PAM (proto-spacer adjacent motif) in foreign DNA, cuts several tens of base pairs upstream thereof and inserts them into the CRISPR region. The inserted target sequence is transcribed together with a repetitive sequence as a series of CRISPR RNA (crRNA) precursors, the repetitive sequence is cleaved by the action of trans-activating crRNA (tracrRNA) partially complementary to crRNA to give mature crRNA, and the mature crRNA forms a complex with tracrRNA and Cas9 which is one of the Cas gene cluster and is a double strand break-inducing endonuclease. The complex recognizes PAM sequence in foreign DNA, binds to a target sequence adjacent thereto, and Cas9 cleaves and removes foreign DNA. This series of mechanism is called CRISPR/Cas9 system.

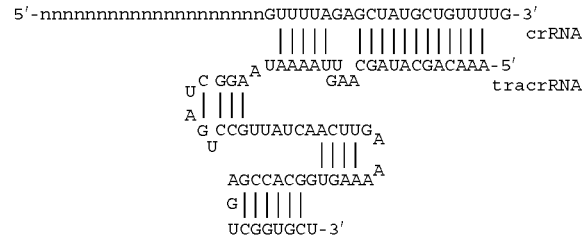

(crRNA: SEQ ID NO:1; tracrRNA: SEQ ID NO:2)
(each n is independently A, G, C or U, and (n)$_{20}$ is a guide region of crRNA).

tracrRNA is necessary for maturation of crRNA and formation of a complex with Cas9 via a hairpin structure which is formed with crRNA. Once a single guide RNA (sgRNA) is made by shortening the 3'-terminal of crRNA and the 5'-terminal of tracrRNA and forming a single strand via a nucleotide linker, then genome editing becomes possible with only Cas9 and sgRNA. Streptococcus pyogenes-derived Cas9 (SpCas9) recognizes NGG as PAM. Therefore, when GG is present on the 3'-side, any double-stranded DNA can be cleaved at the target site (double-stranded DNA break; DSB) simply by replacing about 20 bases on the 5'-terminal side of sgRNA with a desired target sequence. sgRNA in the form of natural form RNA produced using in vitro transcription system or recombinant cells or DNA encoding sgRNA is introduced into a cell together with Cas9 mRNA or protein, or DNA encoding Cas9. The sgRNA introduced (and expressed) in the cell forms a complex with the Cas9 protein and binds to the target sequence to induce DSB in the target gene. The DSB is repaired by non-homologous end joining (NHEJ), but the target gene is destroyed by a frameshift mutation due to accidental insertion or deletion (indel) of base(s) occurring at that time. In addition, co-transfection of a donor DNA having a sequence homologous the target at both ends results in homologous recombination repair, thus enabling base modification and gene insertion.

However, since DSB involves an unexpected genome modification by offtarget cleavage, side effects occur such as strong cytotoxicity, chromosomal translocation and the like. Thus, there are problems that the number of viable cells is extremely small and genetic modification itself is difficult in unicellular microorganisms. The use of DNA expression vectors encoding sgRNA and Cas9 involves sustained expression of sgRNA and Cas9, which in turn renders the problem of offtarget cleavage larger and causes the risk of genetic disturbance due to the incorporation of the expression vector into the chromosome. The above-mentioned problems can be avoided or reduced by introducing sgRNA in the form of RNA and Cas9 in the form of mRNA or protein. However, since natural form (non-modified) RNA is unstable in vivo, there is a problem of degradation of genome editing efficiency in vivo.

For improving nuclease resistance to improve in vivo stability or enhancing intracellular delivery, chemical synthesis of siRNA or antisense RNA molecules by using modified nucleotides is well known; however, reports on genome editing using chemically modified sgRNA are extremely limited. Hendel et al. (non-patent document 1) reports that chemically modified sgRNA modified at the 2'-position of the ribose and the phosphoric acid diester bond at each of the 5'- and 3'-terminal nucleotides markedly improved genomic editing efficiency in human primary cultured cells. However, there is no report on chemical modification of internal nucleotides of sgRNA.

Incidentally, for the purpose of improving the stability in vivo and reducing side effects caused by promoted innate immune response, a single-stranded nucleic acid molecule capable of taking one or two hairpin-type partial secondary structures in which the terminals of a double-stranded nucleic acid such as siRNA, microRNA and the like are linked by various linkers has been developed (see, for example, patent documents 1-6). However, there is no report that the linker was applied to sgRNA having a relatively complicated secondary structure, and an influence on the complex formation with Cas9 and eventually genome editing efficiency is not foreseeable at all.

DOCUMENT LIST

Patent Documents patent document 1: WO 2012/017919
patent document 2: WO 2013/103146
patent document 3: WO 2012/005368
patent document 4: WO 2013/077446
patent document 5: WO 2013/133393
patent document 6: WO 2013/180038

Non-Patent Document non-patent document 1: Hendel et al., Nat. Biotechnol., 33(9): 985-989 (2015)

SUMMARY OF THE INVENTION

Problems to be Solved by the Invention

As mentioned above, in genome editing utilizing the CRISPR/Cas9 system, introduction of sgRNA in the form of RNA has certain advantages, whereas natural form RNA is unstable in vivo, and it is necessary to prepare a vector or a template DNA in production by recombination or in vitro transcription, and it takes time and labor for culturing, enzyme reaction and RNA purification. On the other hand, when chemically-modified RNA is used, genome editing efficiency, in particular, efficiency of introducing gene insertion mutations by homologous recombination is not sufficient.

Therefore, an object of the present invention is to provide a novel artificial sgRNA having an activity equal to or higher than that of a natural form RNA and improved in stability in vivo, and provide a more efficient CRISPR/Cas9 system by combining the artificial sgRNA and Cas9.

Means of Solving the Problems

The present inventors have found that even when a nucleotide linker region (tetraloop of 5'-GAAA-3' in sgRNA corresponding to SpCas9 (following formula) (see Nishimasu et al., Cell, 156: 935-949 (2014))) for forming a single strand by linking the 3'-terminal of crRNA and the 5'-terminal of tracrRNA in sgRNA is substituted with an amino acid derivative linker, an activity equal to or higher than that of the original sgRNA is retained in an in vitro (cell-free or intracellular) DNA cleavage assay. Furthermore, they have also found that even when the linker region existing between stem-loop 1 and stem-loop 2 of tracrRNA and/or the loop portion of stem-loop 2 are/is substituted with an amino acid derivative linker, or even when an amino acid derivative linker is added/inserted into the vicinity of the 5'-terminal and/or the 3'-terminal of sgRNA (arrow in the following formula), an activity equal to or higher than that of the original sgRNA is retained at least in a cell-free system. In addition, a truncated sgRNA obtained by substituting the loop portion of stem-loop 1 or stem-loop 3 with an amino acid derivative linker, or substituting a tetraloop followed by stem portion and/or stem-loop 2 portion with an amino acid derivative linker retained sufficient activity, though lower than that of the original sgRNA, at least in a cell-free system.

In particular, it is interesting that an intracellular cleavage activity equivalent to or higher than that of the original sgRNA was also found in sgRNA introduced with a linker at two positions in which not only the tetraloop portion but also the loop portion of stem-loop 2 were substituted with an amino acid derivative linker. Such artificial sgRNA is considered to have a greater stability improving effect in vivo. See FIG. 16.

As described above, the present inventors have successfully improved the in vivo stability of sgRNA while maintaining the activity of sgRNA (target double-stranded DNA cleavage activity by combination with Cas9) by introducing one or more amino acid derivative linkers into sgRNA, which resulted in the completion of the present invention.

Accordingly, the present invention is as follows.

[1] (1) A single guide RNA represented by the following formula (A):

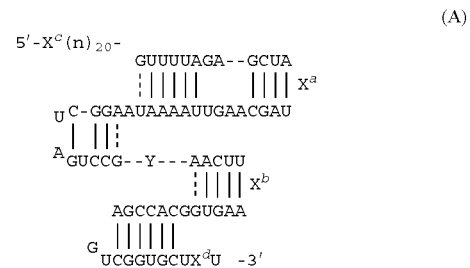

[in the formula (A), $X^a$ is an amino acid derivative linker represented by the following formula (I):

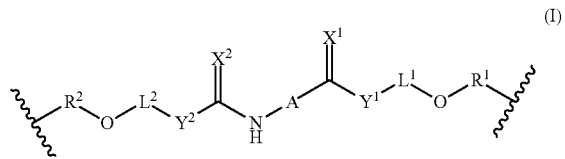

in the formula (I), $X^1$ and $X^2$ are each independently $H_2$, O, S, or NH;

$Y^1$ and $Y^2$ are each independently a single bond, $CH_2$, NH, O, or S;

$L^1$ is an alkylene chain having n carbon atoms, and a hydrogen atom(s) on an alkylene carbon atom(s) may or may not be substituted with OH, $OR^a$, $NH_2$, $NHR^a$, $NR^aR^b$, SH, or $SR^a$, or $L^1$ is a polyether chain obtained by substituting at least one carbon atom on the alkylene chain with an oxygen atom, provided that when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain having m carbon atoms, and a hydrogen atom(s) on an alkylene carbon atom(s) may or may not be substituted with OH, $OR^c$, $NH_2$, $NHR^c$, $NR^cR^d$, SH, or $SR^c$, or $L^2$ is a polyether chain obtained by substituting at least one carbon atom on the alkylene chain with an oxygen atom, provided that when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

m is an integer in the range from 0 to 30;

n is an integer in the range from 0 to 30;

R¹ and R² may or may not be present, and when they are present,

R¹ and R² are each independently a nucleotide residue or the above-mentioned structure (I), A is any atomic group, provided that the following formula (Ia) is an amino acid or a peptide,

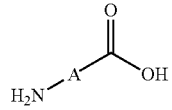
(Ia)

the aforementioned $X^a$ is bonded to the adjacent nucleotide residue via the aforementioned —OR¹— or —OR²—, in the formula (A), $X^b$ and Y each independently show 1 to 5 optional nucleotide linkers, or an amino acid derivative linker represented by the above-mentioned formula (I), the aforementioned $X^b$ and Y are each independently bonded to the adjacent nucleotide residue via the aforementioned —OR¹— or —OR²—, in the formula (A), $X^c$ and $X^d$ may or may not be present, and when they are present, they are each independently an amino acid derivative linker represented by the aforementioned formula (I), the aforementioned $X^c$ and $X^d$ are each independently bonded to the adjacent nucleotide residue via the aforementioned —OR¹— or —OR²—, and in the formula (A), $(n)_{20}$ is a nucleotide sequence consisting of 20±5 nucleotide residues each of which is independently A, G, C or U], or (2) a single guide RNA of the aforementioned formula (A), is wherein 1 to several nucleotide residues are substituted, deleted, inserted or added in a region excluding $(n)_{20}$, which RNA forming a complex with Cas9 protein and having an activity of recognizing a double-stranded DNA containing a target nucleotide sequence complementary to the aforementioned $(n)_{20}$.

[2] The single guide RNA of [1], wherein the amino acid constituting the amino acid or peptide of the aforementioned formula (Ia) is at least one kind selected from the group consisting of glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid, and amino acid represented by the following chemical formula (Ia2):

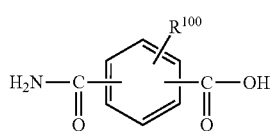
(Ia2)

(in the formula (Ia2), $R^{100}$ is any substituent, may or may not be present, and when it is present, it may be one or in plurality, and when it is in plurality, each may be the same or different), each of which optionally has a substituent or a protecting group.

[3] The single guide RNA of [1] or [2], wherein the aforementioned $X^a$ is represented by the following formula (I-1)-(I-7):

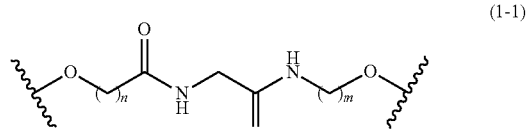
(I-1)

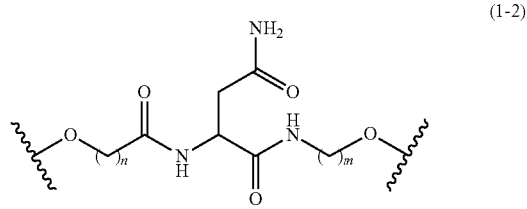
(I-2)

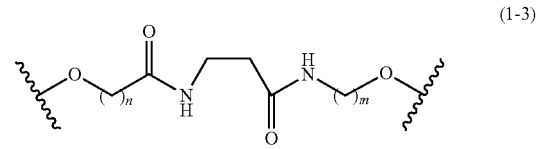
(I-3)

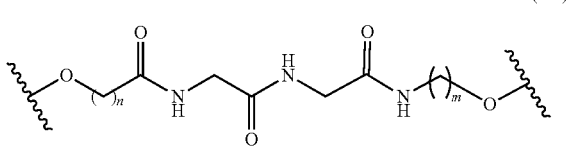
(I-4)

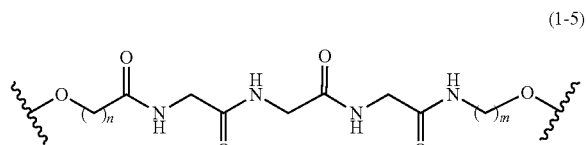
(I-5)

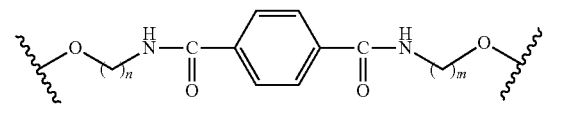
(I-6)

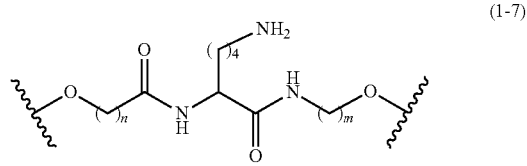
(I-7)

wherein n and m are each independently an integer of 0-30.

[4] The single guide RNA of [3], wherein the aforementioned $X^a$ is represented by the aforementioned formula (I-4) or (I-7) wherein n=5 and m=4.

[5] The single guide RNA of [3], wherein the aforementioned $X^a$ is represented by the aforementioned formula (I-1) wherein n=5 and m=4, or represented by the aforementioned formula (I-6) wherein n=4 and m=4.

[6] The single guide RNA of [1] or [2], wherein the aforementioned $X^a$ is represented by the following formula (II):

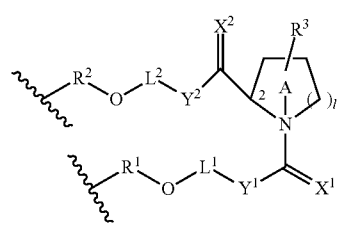
(II)

(in the formula (II), $X^1$ and $X^2$ are each independently $H_2$, O, S, or NH;

$Y^1$ and $Y^2$ are each independently a single bond, $CH_2$, NH, O, or S;

$R^3$ is a hydrogen atom or substituent that is bound to C-3, C-4, C-5, or C-6 on a ring A;

$L^1$ is an alkylene chain composed of n atoms, and a hydrogen atom(s) on an alkylene carbon atom(s) may or may not be substituted with OH, $OR^a$, $NH_2$, $NHR^a$, $NR^aR^b$, SH, or $SR^a$, or $L^1$ is a polyether chain obtained by substituting at least one carbon atom on the alkylene chain with an oxygen atom, provided that when $Y^1$ is NH, O, or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom(s) on an alkylene carbon atom(s) may or may not be substituted with OH, $OR^c$, $NH_2$, $NHR^c$, $NR^cR^d$, SH, or $SR^c$, or $L^2$ is a polyether chain obtained by substituting at least one carbon atom on the alkylene chain with an oxygen atom, provided that when $Y^2$ is NH, O, or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer in the range from 0 to 30;

n is an integer in the range from 0 to 30;

on the ring A, one carbon atom other than C-2 may be substituted with nitrogen, oxygen, or sulfur;

the ring A may contain a carbon-carbon double bond or a carbon-nitrogen double bond, $R^1$ and $R^2$ may or may not be present, and when they are present, $R^1$ and $R^2$ are each independently a nucleotide residue or the aforementioned structure (II), and the aforementioned $X^a$ is bonded to the adjacent nucleotide residue via $-OR^1-$ or $-OR^2-$).

[7] The single guide RNA of [6], wherein the aforementioned $X^a$ is represented by the following formula (II-1)-(II-9):

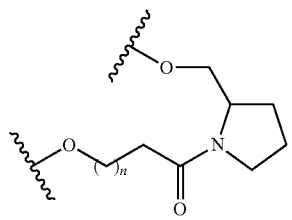
(II-1)

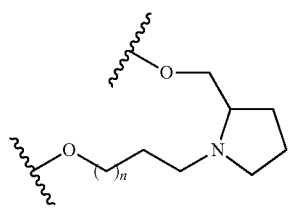
(II-2)

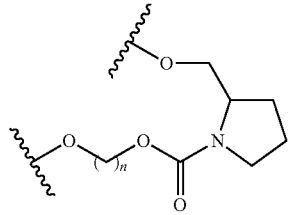
(II-3)

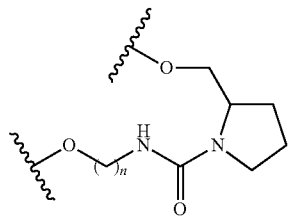
(II-4)

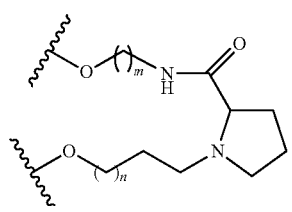
(II-5)

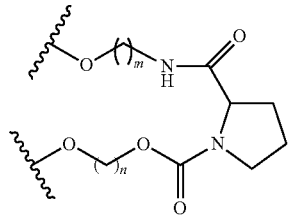
(II-6)

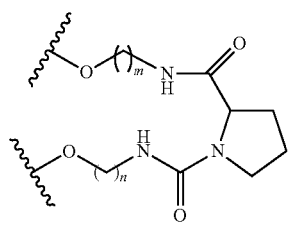
(II-7)

-continued

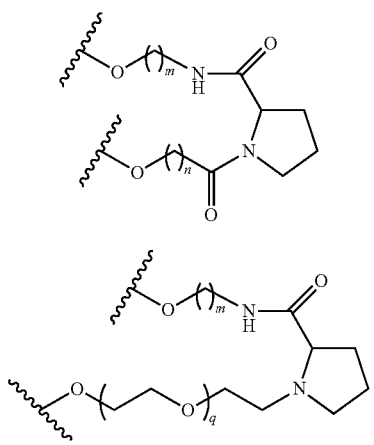

(II-8)

(II-9)

wherein n and m are each independently an integer of 0-30 and q is an integer of 0-10.

[8] The single guide RNA of [7], wherein the aforementioned $X^a$ is represented by the aforementioned formula (II-8) wherein n=5 and m=4, n=7 and m=6, n=9 and m=8, or n=11 and m=10.

[9] The single guide RNA of [1] or [2], wherein the aforementioned $X^a$ is represented by the following formula (III-1)-(III-3):

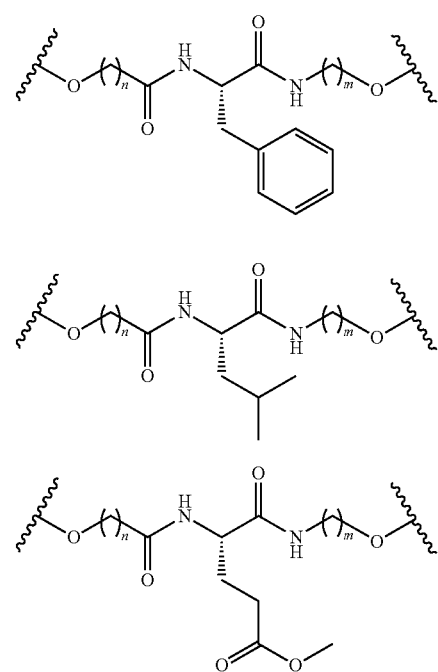

(III-1)

(III-2)

(III-3)

wherein n and m are each independently an integer of 0-30.

[10] The single guide RNA of [9], wherein in the aforementioned each formula, n=5 and m=4.

[11] The single guide RNA of any one of [1] to [10], wherein the aforementioned $X^b$ and Y each independently show 1 to 5 optional nucleotide linkers.

[12] The single guide RNA of [11], wherein the aforementioned $X^c$ and $X^d$ are absent.

[13] The single guide RNA of [11], wherein the aforementioned $X^c$ and $X^d$ are each independently an amino acid derivative linker represented by the aforementioned formula (I).

[14] The single guide RNA of [13], wherein the aforementioned $X^c$ and $X^d$ are amino acid derivative linkers represented by the aforementioned formula (II).

[15] The single guide RNA of [14], wherein the aforementioned $X^c$ and $X^d$ are represented by the aforementioned formula (II-8) wherein n=5 and m=4.

[16] The single guide RNA of [13], wherein the aforementioned $X^c$ and $X^d$ are represented by any of the aforementioned formulas (I-1), (I-4), (I-7) and (III-1)-(III-3), wherein n=5 and m=4, or the aforementioned formula (I-6) wherein n=4 and m=4.

[17] The single guide RNA of any one of [1] to [10], wherein the aforementioned $X^b$ is an amino acid derivative linker represented by the aforementioned formula (I).

[18] The single guide RNA of [17], wherein the aforementioned $X^b$ is an amino acid derivative linker represented by the aforementioned formula (II).

[19] The single guide RNA of [18], wherein the aforementioned $X^b$ is represented by the aforementioned formula (II-8) wherein n=5 and m=4.

[20] The single guide RNA of [17], wherein the aforementioned $X^b$ is represented by any of the aforementioned formulas (I-1), (I-4), (I-7) and (III-1)-(III-3) wherein n=5 and m=4, or represented by the aforementioned formula (I-6) wherein n=4 and m=4.

[21] The single guide RNA of any one of [17] to [20], wherein the aforementioned Y shows 1 to 5 optional nucleotide linkers.

[22] The single guide RNA of any one of [17] to [20], wherein the aforementioned Y is an amino acid derivative linker represented by the aforementioned formula (I).

[23] The single guide RNA of [22], wherein the aforementioned Y is represented by the aforementioned formula (I-4) wherein n=5 and m=4.

[24] The single guide RNA of [22], wherein the aforementioned Y is an amino acid derivative linker represented by the aforementioned formula (II).

[25] The single guide RNA of [24], wherein the aforementioned Y is represented by the aforementioned formula (II-8) wherein n=5 and m=4, n=7 and m=6, n=9 and m=8, or n=11 and m=10.

[26] The single guide RNA of [22], wherein the aforementioned Y is represented by any of the aforementioned formulas (I-1), (I-7) and (III-1)-(III-3) wherein n=5 and m=4 or represented by the aforementioned formula (I-6) wherein n=4 and m=4.

[27] The single guide RNA of [7], wherein the aforementioned $X^a$ is represented by the aforementioned formula (II-8) wherein n=5 and m=4, and 1 to 3 base pairs of the stem adjacent to the aforementioned $X^a$ are deleted.

[28] The single guide RNA of [19], wherein 1 to 4 base pairs of the stem adjacent to the aforementioned $X^b$ are deleted.

[29] The single guide RNA of [28], wherein the aforementioned $X^a$ is represented by the aforementioned formula (II-8) wherein n=5 and m=4, and 1 to 3 base pairs of the stem adjacent to the aforementioned $X^a$ are deleted.

[30] A single guide RNA represented by the aforementioned formula (A), wherein $X^a$, $X^b$ and Y are 1 to 5 optional nucleotide linkers, $X^c$ and $X^d$ are absent, and loop portion (UA) of stem-loop 1 or loop portion (AGU) of stem-loop 3 is substituted with an amino acid derivative linker represented by the aforementioned formula (II-8) wherein n=5 and m=4.

[31] A CRISPR/Cas9 system comprising the single guide RNA of any one of [1] to [30] and Cas9 in combination.

[32] The CRISPR/Cas9 system of [31], wherein said Cas9 is derived from *Streptococcus pyogenes*.

[33] The CRISPR/Cas9 system of [31] or [32], wherein said Cas9 is in the form of a protein, an mRNA encoding same or an expression vector comprising a DNA encoding same.

[34] A method for recognizing a double-stranded DNA, comprising contacting the CRISPR/Cas9 system of any one of [31] to [33] with a target double-stranded DNA.

[35] The method of [34], wherein the Cas9 protein has a double-stranded DNA cleavage activity.

[36] The method of [35], wherein the aforementioned double-stranded DNA is cleaved in a cell.

[37] The method of [36], for knocking out a target gene.

[38] The method of [36], for modifying a base in the target gene, or inserting an exogenous gene in the gene.

[39] A monomer for nucleic acid molecule synthesis represented by any of the following formulas (IV-1)-(IV-3):

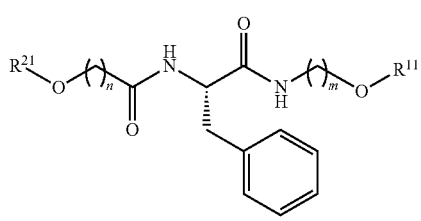

(IV-1)

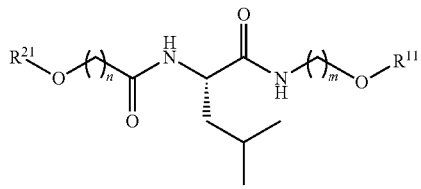

(IV-2)

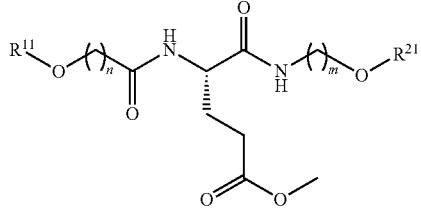

(IV-3)

(in each formula, $R^{11}$ and $R^{21}$ are each independently a hydrogen atom, a protecting group or a phosphoric acid protecting group, and n and m are each independently an integer of 0-30).

[40] The monomer of [39], wherein n=5 and m=4 in each of the aforementioned formulas.

[41] A method for producing a nucleic acid molecule comprising using the monomer of [39] or [40].

[42] The method of [41], wherein the aforementioned nucleic acid molecule is the single guide RNA of any one of [1] to [26].

[43] Use of the monomer of [39] or [40] in the production of a nucleic acid molecule.

[44] The use of [43], wherein the aforementioned nucleic acid molecule is the single guide RNA of any one of [1] to [26].

Effect of the Invention

The artificial sgRNA of the present invention can be synthesized easily at a low cost and can improve the in vivo stability of sgRNA without impairing the cleavage activity of the target double-stranded DNA. Therefore, it can improve genome editing efficiency, particularly genome editing efficiency in vivo.

DESCRIPTION OF EMBODIMENTS

1. Artificial sgRNA

Figure 16:
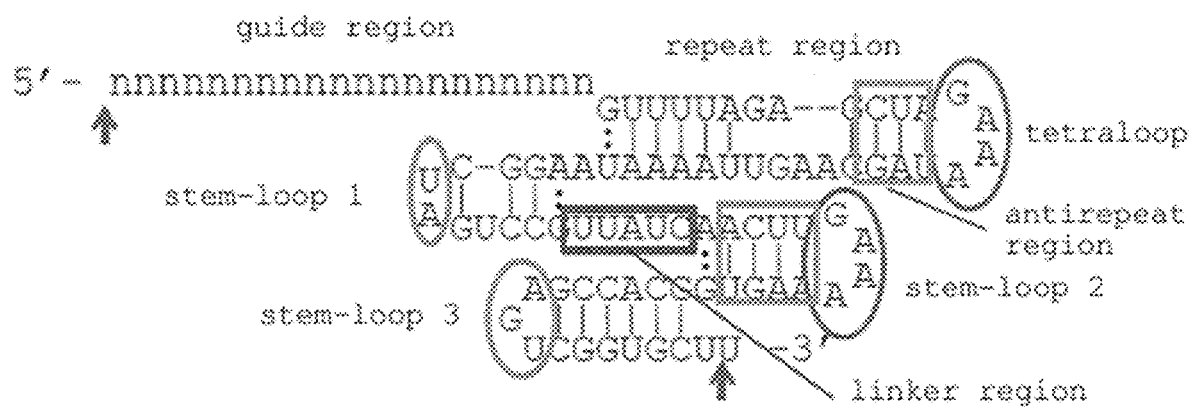
FIG. 16 shows a chemically-modified sgRNA which is a single guide RNA (natural form sgRNA).

The present invention provides a chemically-modified sgRNA which is the single guide RNA (natural form sgRNA) shown in FIG. 16 comprising one or more amino acid derivative linkers at least in the internal sequence thereof (to be also referred to as "the artificial sgRNA of the present invention" in the present specification), which natural form sgRNA being obtained by chimerization (truncation and forming single strand) of crRNA and tracrRNA derived from *Streptococcus pyogenes* and shown by the following formula:

crRNA

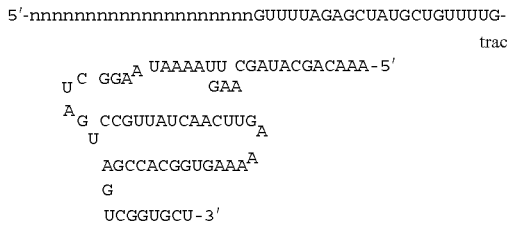

tracrRNA (crRNA: SEQ ID NO: 1; tracrRNA: SEQ ID NO:2)
(each n is independently A, G, C or U and (n)$_{20}$ is a guide region of crRNA).

The natural form sgRNA from which the artificial sgRNA of the present invention is derived (while sgRNA itself is inherently an artificial RNA, it is referred to as natural form sgRNA in the sense of sgRNA consisting only of "natural form (i.e., non-modified) nucleotides" in the present specification) contains, as mentioned above, a guide region ((n)$_{20}$) complementary to the target nucleotide sequence on the 5'-terminal, crRNA-derived repeat region and tracrRNA-derived antirepeat region are linked at the downstream thereof via a tetraloop consisting of 4 nucleotides (GAAA), and forms a stem-loop structure. Furthermore, it contains three tracrRNA-derived stem-loop structures at the downstream of the antirepeat region, and has a linker region consisting of 5 nucleotides (UUAUC) between stem-loop 1 and stem-loop 2.

The length of the nucleotide sequence ((n)$_{20}$) in the guide region only needs to be sufficient for sgRNA to specifically bind to the target nucleotide sequence. For example, when a mutation is introduced into a particular site in the genomic DNA of a mammal, it is not less than 12 nucleotides, preferably not less than 15 nucleotides, more preferably not less than 17 nucleotides, according to the genome size thereof. While the upper limit of the length is not particularly limited, it is preferably not more than 25 nucleotides, more preferably not more than 22 nucleotides. More specifically, the nucleotide length of the guide region is 20±5 nucleotides, preferably 17-22 nucleotides, particularly preferably 20 nucleotides.

Specifically, the artificial sgRNA of the present invention is characterized in that at least the tetraloop portion of the natural form sgRNA is substituted by an amino acid derivative linker ($X^a$). That is, the artificial sgRNA of the present invention is a single guide RNA represented by the following formula (A):

(A)

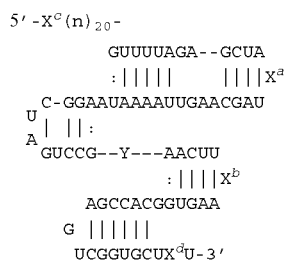

[in the formula (A), $X^a$ is an amino acid derivative linker represented by the following formula (I):

(I)

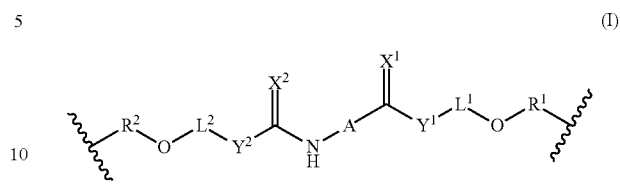

in the formula (I),
$X^1$ and $X^2$ are each independently $H_2$, O, S or NH;
$Y^1$ and $Y^2$ are each independently a single bond, $CH_2$, NH, O or S;
$L^1$ is an alkylene chain having n carbon atoms, and a hydrogen atom(s) on an alkylene carbon atom(s) may or may not be substituted with OH, $OR^a$, $NH_2$, $NHR^a$, $NR^aR^b$, SH, or $SR^a$, or
$L^1$ is a polyether chain obtained by substituting at least one carbon atom on the alkylene chain with an oxygen atom, provided that when $Y^1$ is NH, O or S, an atom bound to $Y^1$ in
$L^1$ is carbon, an atom bound to $OR^1$ in $L^1$ is carbon, and oxygen atoms are not adjacent to each other;
$L^2$ is an alkylene chain having m carbon atoms, and a hydrogen atom(s) on an alkylene carbon atom(s) may or may not be substituted with OH, $OR^c$, $NH_2$, $NHR^c$, $NR^cR^d$, SH, or $SR^c$, or
$L^2$ is a polyether chain obtained by substituting at least one carbon atom on the alkylene chain with an oxygen atom, provided that when $Y^2$ is NH, O or S, an atom bound to $Y^2$ in
$L^2$ is carbon, an atom bound to $OR^2$ in $L^2$ is carbon, and oxygen atoms are not adjacent to each other; $R^a$, $R^b$, $R^c$, and $R^d$ are each independently a substituent or a protecting group;
l is 1 or 2;
m is an integer in the range from 0 to 30;
n is an integer in the range from 0 to 30;
$R^1$ and $R^2$ may or may not be present, and when they are present,
$R^1$ and $R^2$ are each independently a nucleotide residue or the above-mentioned structure (I),
A is any atomic group, provided that the following formula (Ia) is an amino acid or a peptide, (Ia)

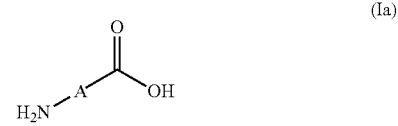

the aforementioned $X^a$ is bonded to the adjacent nucleotide residue via the aforementioned —$OR^1$— or —$OR^2$—,
in the formula (A), $X^b$ and Y each independently show 1 to 5 optional nucleotide linkers, or an amino acid derivative linker represented by the above-mentioned formula (I),
the aforementioned $X^b$ and Y are each independently bonded to the adjacent nucleotide residue via the aforementioned —$OR^1$— or —$OR^2$—,
in the formula (A), $X^c$ and $X^d$ may or may not be present, and when they are present, they are each independently an amino acid derivative linker represented by the aforementioned formula (I), the aforementioned $X^c$ and $X^d$ are each independently bonded to the adjacent nucleotide residue via the aforementioned —$OR^1$— or —$OR^2$—, and in the formula (A), $(n)_{20}$ is a nucleotide sequence consisting of 20±5 nucleotide residues each of which is independently A, G, C or U], or (2) a single guide RNA of the aforementioned formula (A), wherein 1 to several nucleotide residues are substituted, deleted, inserted or added in a region excluding $(n)_{20}$, which RNA forming a complex with Cas9 protein and having an activity of recognizing a double-stranded DNA containing a target nucleotide sequence complementary to the aforementioned $(n)_{20}$.

In the formula (I), $X^1$ and $X^2$ are, for example, each independently $H_2$, O, S or NH. In the formula (I), "$X^1$ is $H_2$" means that $X^1$ forms $CH_2$ (a methylene group) together with a carbon atom to which $X^1$ binds. The same applies to $X^2$.

In the formula (I), $Y^1$ and $Y^2$ are each independently a single bond, $CH_2$, NH, O or S.

In the formula (I), $L^1$ is an alkylene chain having n carbon atoms. A hydrogen atom(s) on an alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the alkylene chain with an oxygen atom. The polyether chain is, for example, polyethylene glycol. When $Y^1$ is NH, O or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the formula (I), $L^2$ is an alkylene chain having m carbon atoms. A hydrogen atom(s) on an alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the alkylene chain with an oxygen atom. When $Y^2$ is NH, O or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. n and m can be set as appropriate depending on, for example, a desired length of the linker region (Lx). For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

$R^a$, $R^b$, $R^c$, and $R^d$ is, for example, each independently a substituent or a protecting group. Examples of the substituent include hydroxy, carboxy, sulfo, halogens, alkyl halides (haloalkyl e.g., $CF_3$, $CH_2CF_3$, $CH_2CCl_3$), nitro, nitroso, cyano, alkyls (e.g., methyl, ethyl, isopropyl, tert-butyl), alkenyls (e.g., vinyl), alkynyls (e.g., ethynyl), cycloalkyls (e.g., cyclopropyl, adamantyl), cycloalkylalkyls (e.g., cyclohexylmethyl, adamantylmethyl), cycloalkenyls (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryls (e.g., phenyl, naphthyl), arylalkyls (e.g., benzyl, phenethyl), alkylaryl (e.g., p-methylphenyl), heteroaryls (e.g., pyridyl, furyl), heteroarylalkyls (e.g., pyridylmethyl), heterocyclyls (e.g., piperidyl), heterocyclylalkenyl, heterocyclylalkyls (e.g., morpholylmethyl), alkoxys (e.g., methoxy, ethoxy, propoxy, butoxy), halogenated alkoxys (e.g., $OCF_3$), alkenyloxys (e.g., vinyloxy, allyloxy), aryloxys (e.g., phenyloxy), alkyloxycarbonyls (e.g., methoxycarbonyl, ethoxycarbonyl, tert-butoxycarbonyl), arylalkyloxys (e.g., benzyloxy), aminos [alkylaminos (e.g., methylamino, ethylamino, dimethylamino), acylaminos (e.g., acetylamino, benzoylamino), arylalkylaminos (e.g., benzylamino, tritylamino), hydroxyamino], aminoalkyl (e.g., aminomethyl), alkylaminoalkyls (e.g., diethylaminomethyl), carbamoyl, sulfamoyl, oxo, silyl, silyloxyalkyl and the like. These substituents are optionally substituted by one or more further substituents or further protecting groups. While the aforementioned further substituent is not particularly limited, for example, it may be a substituent exemplified above. The aforementioned further protecting group is not particularly limited and, for example, it may be a protecting group exemplified below. The same applies hereafter.

The aforementioned protecting group (or the aforementioned further protecting group) is, for example, a functional group that inactivates a highly-reactive functional group. Examples of the protecting group include known protecting groups. Regarding the protecting group, for example, the description in the literature (J. F. W. McOmie, "Protecting Groups in Organic Chemistry", Plenum Press, London and New York, 1973) is incorporated herein by reference. The protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When $R^3$ is $OR^4$, the protecting group is not particularly limited, and examples thereof include a TBDMS group, an ACE group, a TOM group, a CEE group, a CEM group, and a TEM group. Besides these, silyl-containing groups of the following formulas (P1) and (P2) can be mentioned. Of these, any of DMtr group and the aforementioned silyl-containing group is preferable.

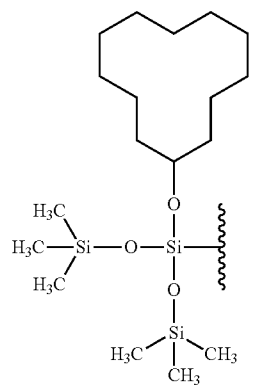

(P1)

-continued

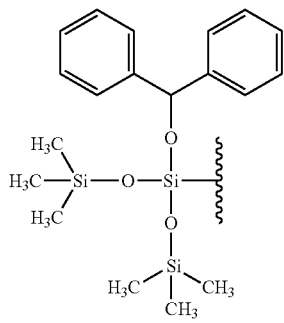

(P2)

In the formula (I), each hydrogen atom may be, for example, independently substituted with a halogen such as Cl, Br, F, or I.

The aforementioned $X^a$ is bonded to the adjacent nucleotide residue via $-OR^1-$ or $-OR^2-$. Here, $R^1$ and $R^2$ may or may not be present. When $R^1$ and $R^2$ are present, $R^1$ and $R^2$ are each independently a nucleotide residue or the abovementioned structure (I). When $R^1$ and/or $R^2$ have/has a structure of the aforementioned formula (I), $X^a$ is a structure in which not less than two amino acid derivative residues having the structure of the aforementioned formula (I) are linked. The structure of the aforementioned formula (I) may be contained in the number of, for example, 1, 2, 3 or 4. Thus, when a plurality of the aforementioned structures are contained, the structure of the aforementioned (I) may be, for example, directly linked or bonded via the aforementioned nucleotide residue.

The combination of the adjacent nucleotide residue and $-OR^1-$ and $-OR^2-$ is not particularly limited, and may be, for example, either of the following conditions.

Condition (1)

The 3'-terminal of the adjacent nucleotide residue is linked to the structure of the aforementioned formula (I) via $-OR^2-$ and the 5'-terminal of the adjacent nucleotide residue is linked to the structure of the aforementioned formula (I) via $-OR^1-$.

Condition (2)

The 3'-terminal of the adjacent nucleotide residue is linked to the structure of the aforementioned formula (I) via $-OR^1-$ and the 5'-terminal of the adjacent nucleotide residue is linked to the structure of the aforementioned formula (I) via $-OR^2-$.

In the aforementioned formula (I), atomic group A is not particularly limited as long as the following formula (Ia):

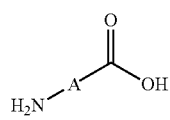

(Ia)

is an amino acid or a peptide.

For example, the atomic group A in the aforementioned (I) or (Ia) may or may not contain, for example, at least one selected from the group consisting of chain atomic group, alicyclic atomic group and aromatic atomic group. While the aforementioned chain atomic group is not particularly limited, for example, alkyl, alkenyl, alkynyl, haloalkyl, hydroxyalkyl, alkoxyalkyl, aminoalkyl, silyl, silyloxyalkyl and the like can be mentioned. While the aforementioned alicyclic atomic group is not particularly limited, for example, cycloalkyl, cycloalkenyl, cycloalkylalkyl, cyclylalkyl and the like can be mentioned. While the aforementioned aromatic atomic group is not particularly limited, for example, aryl, arylalkyl, alkylaryl, condensed-ring aryl, condensed-ring arylalkyl, condensed-ring alkylaryl and the like can be mentioned. In the atomic group A in the aforementioned formula (I) or (Ia), each of the aforementioned atomic groups may or may not further have a substituent or a protecting group. When the aforementioned substituent or protecting group is in plurality, they may be the same or different. The aforementioned substituents are, for example, those exemplified for the aforementioned $R^a$, $R^b$, $R^c$ and $R^d$, more specifically, for example, halogen, hydroxy, alkoxy, amino, carboxy, sulfo, nitro, carbamoyl, sulfamoyl, alkyl, is alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. The aforementioned protecting groups are, for example, the same as those exemplified for the aforementioned $R^a$, $R^b$, $R^c$ and $R^d$.

In the present invention, the "amino acid" refers to any organic compound containing at least one amino group and at least one carboxy group in a molecule. The "peptide" refers to an organic compound having a structure wherein not less than 2 molecules of amino acid are bonded via a peptide bond. The aforementioned peptide bond may be an acid amide structure or an acid imide structure. When plural amino groups are present in the amino acid molecule represented by the aforementioned formula (Ia), the amino group clearly shown in the aforementioned formula (Ia) may be any amino group. In addition, when plural carboxy groups are present in the amino acid molecule represented by the aforementioned formula (Ia), the carboxy group clearly shown in the aforementioned formula (Ia) may be any carboxy group.

In the aforementioned linker region ($X^a$) of the artificial sgRNA of the present invention, the aforementioned amino acid may be natural amino acid or artificial amino acid. In the present invention, the "natural amino acid" refers to an amino acid having a naturally-occurring structure or an optical isomer thereof. The production method of the aforementioned natural amino acid is not particularly limited and, for example, it may be extracted from the nature, or may be synthesized. In the present invention, moreover, the "artificial amino acid" refers to an amino acid having a structure not occurring naturally. That is, the aforementioned artificial amino acid is an amino acid, i.e., a carboxylic acid derivative containing an amino group (organic compound containing at least one amino group and at least one carboxy group in a molecule) and having a structure not occurring naturally. The aforementioned artificial amino acid preferably does not contain, for example, a hetero ring. The aforementioned amino acid may be an amino acid constituting, for example, a protein. The aforementioned amino acid may be, for example, at least one kind selected from the group consisting of glycine, α-alanine, arginine, asparagine, aspartic acid, cysteine, cystine, glutamine, glutamic acid, histidine, isoleucine, leucine, lysine, hydroxylysine, methionine, phenylalanine, serine, threonine, tyrosine, valine, proline, 4-hydroxyproline, tryptophan, β-alanine, 1-amino-2-carboxycyclopentane, aminobenzoic acid, aminopyridinecarboxylic acid and amino acid represented by the following chemical formula (Ia2), and may or may not further have a substituent or a protecting group. Examples of the aforementioned substituent include the substituents exemplified for the aforementioned $R^a$, $R^b$, $R^c$ and $R^d$. More specifically, for example, halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like can be mentioned. The aforementioned protecting group is the same as, for example, the protecting groups exemplified for the aforementioned $R^a$, $R^b$, $R^c$ and $R^d$. When the amino acid or peptide of the aforementioned formula (Ia) contains isomers such as optical isomer, geometric isomer, stereoisomer and the like, any isomer can be used.

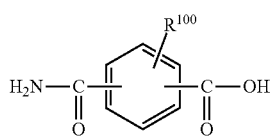
(Ia2)

In the aforementioned chemical formula (Ia2), $R^{100}$ is any substituent, and may or may not be present. When it is present, it may be present singly or in plurality. When it is present in plurality, they may be the same or different from each other. Examples of the aforementioned any substituent for $R^{100}$ include those exemplified as the aforementioned $R^a$, $R^b$, $R^c$ or $R^d$. More specific examples thereof include halogen, hydroxy, alkoxy, amino, carboxy, sulfo, nitro, carbamoyl, sulfamoyl, alkyl, alkenyl, alkynyl, haloalkyl, aryl, arylalkyl, alkylaryl, cycloalkyl, cycloalkenyl, cycloalkylalkyl, cyclylalkyl, hydroxyalkyl, alkoxyalkyl, aminoalkyl, silyl, silyloxyalkyl, pyrrolyl, imidazolyl, and the like. In addition, the structure of the aforementioned chemical formula (Ia2) may be, for example, the following chemical formula (Ia3):

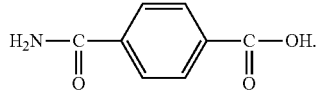
(Ia3)

When the structure of the aforementioned chemical formula (Ia) is the aforementioned chemical formula (Ia2), the structure of atomic group A in the aforementioned chemical formula (I) is represented by the following chemical formula (A2). $R^{100}$ in the following chemical formula (A2) is the same as $R^{100}$ in the aforementioned chemical formula (Ia2). In addition, when the structure of the aforementioned chemical formula (Ia) is the aforementioned chemical formula (Ia3), the structure of atomic group A in the aforementioned chemical formula (I) is represented by the following chemical formula (A2a):

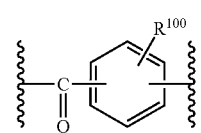
(A2)

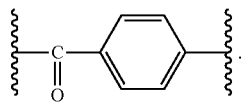
(A2a)

Examples of the structure of the aforementioned chemical formula (I) include the following chemical formulas (I-1)-(I-7). In the following chemical formulas (I-1)-(I-7), n and m are the same as in the aforementioned chemical formula (I).

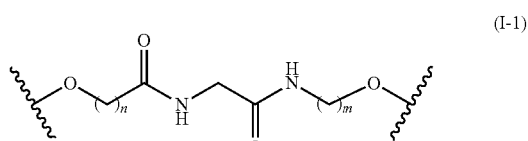
(I-1)

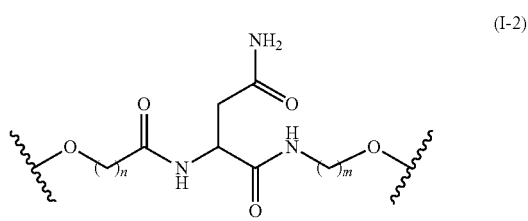
(I-2)

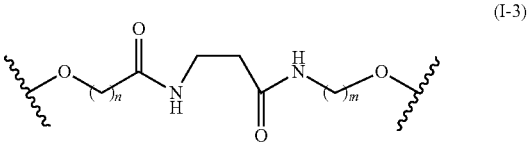
(I-3)

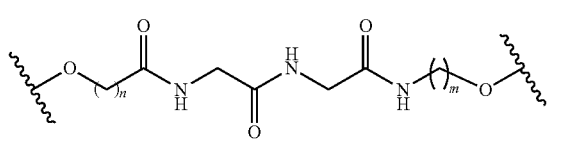
(I-4)

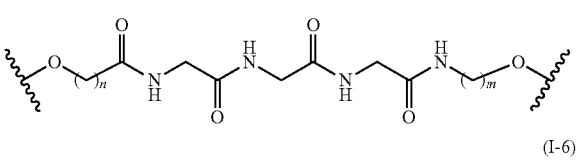
(I-5)

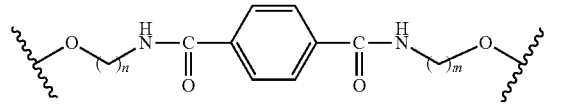
(I-6)

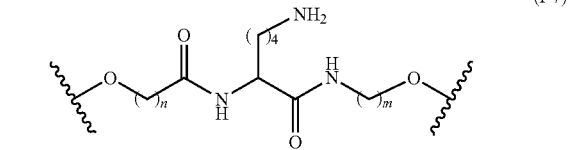
(I-7)

In the aforementioned chemical formulae (I-1) to (I-7), n and m are not particularly limited, and are as described above. Specific examples thereof include n=11 and m=12 or n=5 and m=4 (Gly in Example mentioned later) in the aforementioned chemical formula (I-1), n=5 and m=4 (GlyGly in Example mentioned later) in the aforementioned chemical formula (I-4), n=4 and m=4 (TP in Example mentioned later) in the aforementioned chemical formula (I-6), and n=5 and m=4 (K in Example mentioned later) in the aforementioned chemical formula (1-7). The structures are shown by the following chemical formulas (I-1a), (I-1b), (I-4a), (I-6a) and (I-7a). Of these, the formulas (I-1b), (I-6a) and (I-7a) are preferable.

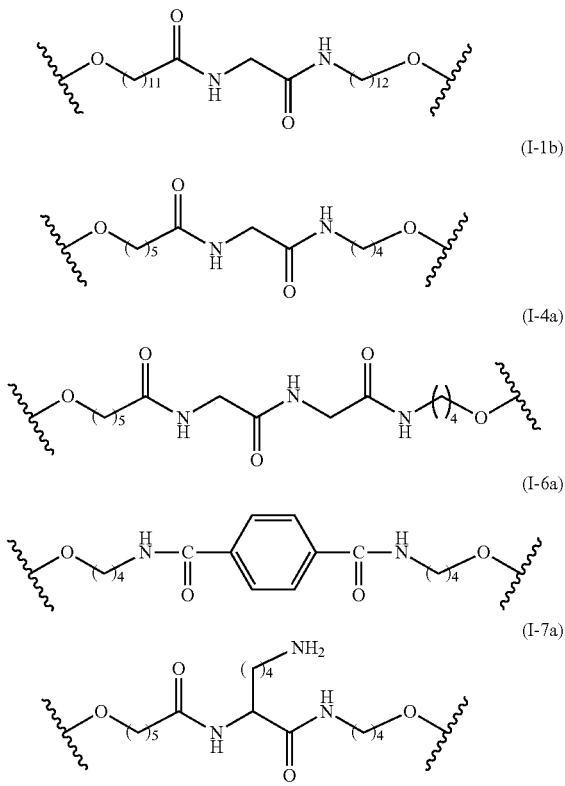

Alternatively, in the artificial sgRNA of the present invention, the aforementioned linker region ($X^a$) is shown by the following formula (II):

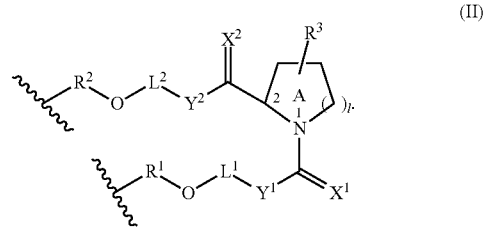

(II)

In the aforementioned formula (II), for example, $X^1$ and $X^2$ are each independently $H_2$, O, S or NH;

$Y^1$ and $Y^2$ are each independently a single bond, $CH_2$, NH, O or S;

$R^3$ is a hydrogen atom or substituent that is bound to C-3, C-4, C-5, or C-6 on a ring A;

$L^1$ is an alkylene chain composed of n atoms, and a hydrogen atom(s) on an alkylene carbon atom(s) may or may not be substituted with OH, $OR^a$, $NH_2$, $NHR^a$, $NR^aR^b$, SH, or $SR^a$, or, $L^1$ is a polyether chain obtained by substituting at least one carbon atom on the alkylene chain with an oxygen atom, provided that: when $Y^1$ is NH, O or S, an atom bound to $Y^1$ in $L^1$ is carbon, an atom bound to $OR^1$ in $L^1$ is carbon, and oxygen atoms are not adjacent to each other;

$L^2$ is an alkylene chain composed of m atoms, and a hydrogen atom(s) on an alkylene carbon atom(s) may or may not be substituted with OH, $OR^c$, $NH_2$, $NHR^c$, $NR^cR^d$, SH, or $SR^c$, or $L^2$ is a polyether chain obtained by substituting at least one carbon atom on the alkylene chain with an oxygen atom, provided that: when $Y^2$ is NH, O or S, an atom bound to $Y^2$ in $L^2$ is carbon, an atom bound to $OR^2$ in $L^2$ is carbon, and oxygen atoms are not adjacent to each other;

$R^a$, $R^b$, $R^c$, and $R^d$ are each independently a substituent or a protecting group;

l is 1 or 2;

m is an integer of 0 to 30;

n is an integer of 0 to 30;

on the ring A, one carbon atom other than C-2 may be substituted with nitrogen, oxygen, or sulfur;

the ring A may contain a carbon-carbon double bond or a carbon-nitrogen double bond;

$R^1$ and $R^2$ may or may not be present, and when they are present, $R^1$ and $R^2$ are each independently a nucleotide residue or the structure of the formula (II), and the aforementioned $X^a$ is bonded to the adjacent nucleotide residue via the aforementioned —$OR^1$— or —$OR^2$—.

In the formula (II), $X^1$ and $X^2$ are each independently, for example, $H_2$, O, S or NH. In the formula (I), "$X^1$ is $H_2$" means that $X^1$ forms $CH_2$ (a methylene group) together with a carbon atom to which $X^1$ binds. The same applies to $X^2$.

In the formula (II), $Y^1$ and $Y^2$ are each independently a single bond, $CH_2$, NH, O or S.

In the aforementioned formula (II), $L^1$ is an alkylene chain composed of n atoms. A hydrogen atom(s) on an alkylene carbon atom(s) may or may not be substituted with, for example, OH, $OR^a$, $NH_2$, $NHR^a$, $NR^aR^b$, SH, or $SR^a$. Alternatively, $L^1$ may be a polyether chain obtained by substituting at least one carbon atom on the alkylene chain with an oxygen atom. The polyether chain is, for example, polyethylene glycol. When $Y^1$ is NH, O or S, an atom bound to $Y^1$ in $L^1$ is carbon, an atom bound to $OR^1$ in $L^1$ is carbon, and oxygen atoms are not adjacent to each other. That is, for example, when $Y^1$ is O, this oxygen atom and the oxygen atom in $L^1$ are not adjacent to each other, and the oxygen atom in $OR^1$ and the oxygen atom in $L^1$ are not adjacent to each other.

In the formula (II), $L^2$ is an alkylene chain composed of m atoms. A hydrogen atom(s) on an alkylene carbon atom(s) may or may not be substituted with, for example, OH, $OR^c$, $NH_2$, $NHR^c$, $NR^cR^d$, SH, or $SR^c$. Alternatively, $L^2$ may be a polyether chain obtained by substituting at least one carbon atom on the alkylene chain with an oxygen atom. When $Y^2$ is NH, O or S, an atom bound to $Y^2$ in $L^2$ is carbon, an atom bound to $OR^2$ in $L^2$ is carbon, and oxygen atoms are not adjacent to each other. That is, for example, when $Y^2$ is O, this oxygen atom and the oxygen atom in $L^2$ are not adjacent to each other, and the oxygen atom in $OR^2$ and the oxygen atom in $L^2$ are not adjacent to each other.

n of $L^1$ and m of $L^2$ are not particularly limited, and the lower limit of each of them may be 0, for example, and the upper limit of the same is not particularly limited. n and m can be set as appropriate depending on, for example, a desired length of the aforementioned non-nucleotide structure. For example, from the view point of manufacturing cost, yield, and the like, n and m are each preferably 0 to 30, more preferably 0 to 20, and still more preferably 0 to 15. n and m may be the same (n=m) or different. n+m is, for example, 0 to 30, preferably 0 to 20, and more preferably 0 to 15.

$R^a$, $R^b$, $R^c$, and $R^d$ is, for example, each independently a substituent or a protecting group. The substituent and the protecting group are, for example, the same as described above.

In the aforementioned formula (II), a hydrogen atoms each independently may be substituted with, for example, a halogen such as Cl, Br, F, or I.

The aforementioned $X^a$ is bonded to the adjacent nucleotide residue via —$OR^1$— or —$OR^2$—. $R^1$ and $R^2$ may or may not be present. When $R^1$ and $R^2$ are present, $R^1$ and $R^2$ are each independently a nucleotide residue or the structure represented by the formula (II). When $R^1$ and/or $R^2$ is the structure represented by the formula (II), the structure of the linker region ($X^a$) is such that, for example, two or more of the amino acid derivative residues having the above-mentioned structure of the formula (II) are linked to each other. The number of the structures of the formula (II) may be, for example, 1, 2, 3, or 4. When the linker region (Lx) includes a plurality of the structures, the structures of the formula (II) may be linked, for example, either directly or via the nucleotide residue (s).

The combination of the adjacent nucleotide residue and —$OR^1$— and —$OR^2$— is not particularly limited, and may be, for example, either of the following conditions.

Condition (1)

The 3'-terminal of the adjacent nucleotide residue is linked to the structure of the aforementioned formula (II) via —$OR^2$— and the 5'-terminal of the adjacent nucleotide residue is linked to the structure of the aforementioned formula (II) via —$OR^1$—.

Condition (2)

The 3'-terminal of the adjacent nucleotide residue is linked to the structure of the aforementioned formula (II) via —$OR^1$— and the 5'-terminal of the adjacent nucleotide residue is linked to the structure of the aforementioned formula (II) via —$OR^2$—.

In the aforementioned formula (II), 1 in the ring A is 1 or 2. When $l=1$, the ring A is a 5-membered ring, which is, for example, the pyrrolidine skeleton. The pyrrolidine skeleton is, for example, a proline skeleton, a prolinol skeleton, or the like, and specific examples include divalent structures of the proline skeleton and the prolinol skeleton. When $l=2$, the ring A is a 6-membered ring, which is, for example, the piperidine skeleton. On the ring A, one carbon atom other than C-2 may be substituted with nitrogen, oxygen, or sulfur. Furthermore, the ring A may contain a carbon-carbon double bond or a carbon-nitrogen double bond. The ring A may be, for example, in either L-form or D-form.

In the formula (II), $R^3$ is a hydrogen atom or substituent that is bound to C-3, C-4, C-5, or C-6 on the ring A. When $R^3$ is the substituent, there may be one substituent $R^3$, two or more substituents $R^3$, or no substituent $R^3$, and when there are a plurality of substituents $R^3$, they may be the same or different.

The substituent $R^3$ is, for example, a halogen, OH, $OR^4$, $NH_2$, $NHR^4$, $NR^4R^5$, SH, $SR^4$, an oxo group (=O), or the like.

$R^4$ and $R^5$ are each a substituent or a protecting group, and they may be the same or different. Examples of the substituent include halogens, alkyls, alkenyls, alkynyls, haloalkyls, aryls, heteroaryls, arylalkyls, cycloalkyls, cycloalkenyls, cycloalkylalkyls, cyclylalkyls, hydroxyalkyls, alkoxyalkyls, aminoalkyls, heterocyclylalkenyls, heterocyclylalkyls, heteroarylalkyls, silyls, and silyloxyalkyls. The same applies hereinafter. The substituent $R^3$ may be any of the above-listed substituents.

The protecting group is, for example, a functional group that inactivates a highly-reactive functional group. Examples of the protecting group include known protecting groups. Regarding the protecting group, for example, the description in the literature (J. F. W. McOmie, "Protecting Groups in Organic Chemistry", Plenum Press, London and New York, 1973) is incorporated herein by reference. The protecting group is not particularly limited, and examples thereof include a tert-butyldimethylsilyl group (TBDMS), a bis(2-acetoxyethyloxy)methyl group (ACE), a triisopropylsilyloxymethyl group (TOM), a 1-(2-cyanoethoxy)ethyl group (CEE), a 2-cyanoethoxymethyl group (CEM), a tolylsulfonylethoxymethyl group (TEM), and a dimethoxytrityl group (DMTr). When $R^3$ is $OR^4$, the protecting group is not particularly limited, and examples thereof include a TBDMS group, an ACE group, a TOM group, a CEE group, a CEM group, and a TEM group. Other examples of the protecting group include silyl-containing groups. The same applies hereinafter.

Examples of the structure of the formula (II) include the structures of the following formulae (II-1) to (II-9). In the following formulae, n and m are the same as in the formula (II). In the following formulae, q is an integer from 0 to 10.

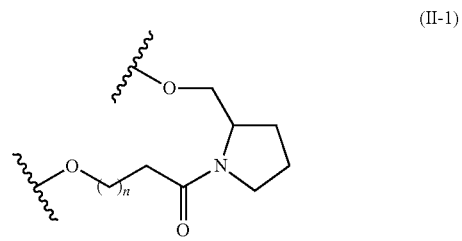

(II-1)

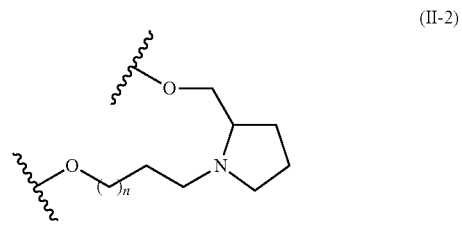

(II-2)

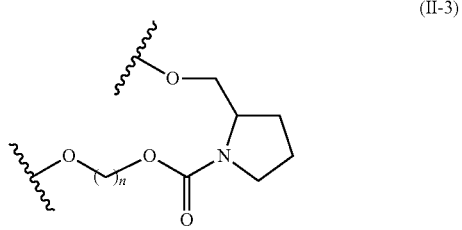

(II-3)

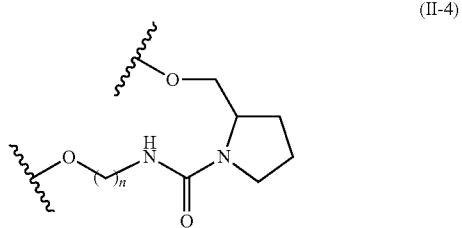

(II-4)

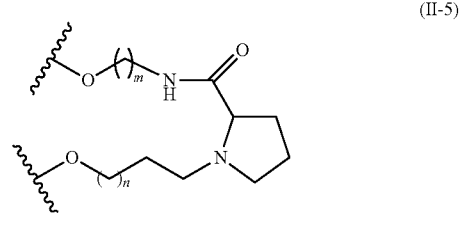

(II-5)

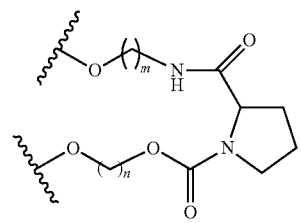
(II-6)

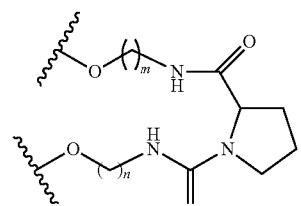
(II-7)

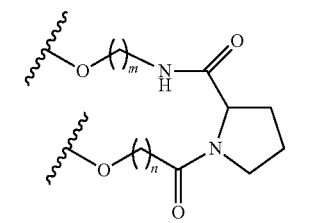
(II-8)

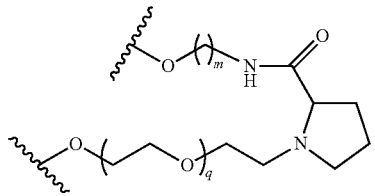
(II-9)

In the formulae (II-1) to (II-9), n, m, and q are not particularly limited, and are as described above. Specific examples are as follows: in the formula (II-1), n=8; in the formula (II-2), n=3; in the formula (II-3), n=4 or 8; in the formula (II-4), n=7 or 8; in the formula (II-5), n=3 and m=4; in the formula (II-6), n=8 and m=4; in the formula (II-7) n=8 and m=4; in the formula (II-8), n=5 and m=4 (P in Example described later), n=7 and m=6 (P13 in Example described later), n=9 and m=8 (P14 in Example described later), or n=11 and m=10 (P15 in Example described later); and in the formula (II-9), q=1 and m=4. The following formula (II-4a) shows an example of the formula (II-4) (n=8), and the following formula (II-8a) shows an example of the formula (II-8) (n=5, m=4).

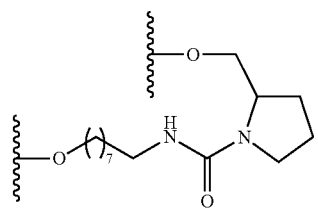
(II-4a)

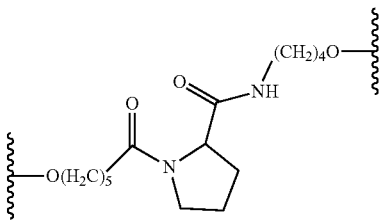
(II-8a)

In the present invention, the term "alkyl" encompasses, for example, straight-chain and branched alkyl groups. The number of carbon atoms in the alkyl is not particularly limited, and is, for example, 1 to 30, preferably 1 to 6 or 1 to 4. Examples of the alkyl group include: methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, and n-decyl. Among them, for example, methyl, ethyl, n-propyl, isopropyl, n-butyl, isobutyl, sec-butyl, tert-butyl, n-pentyl, isopentyl, neopentyl, n-hexyl, isohexyl, and the like are preferable.

In the present invention, the term "alkenyl" encompasses, for example, straight-chain and branched alkenyls. Examples of the alkenyl include the above-described alkyls having one or more double bonds. The number of carbon atoms in the alkenyl is not particularly limited, and is, for example, the same as that in the alkyl, preferably 2 to 8. Examples of the alkenyl include vinyl, 1-propenyl, 2-propenyl, 1-butenyl, 2-butenyl, 3-butenyl, 1,3-butadienyl, and 3-methyl-2-butenyl.

In the present invention, the term "alkynyl" encompasses, for example, straight-chain and branched alkynyls. Examples of the alkynyl include the above-described alkyls having having one or more triple bonds. The number of carbon atoms in the alkynyl is not particularly limited, and is, for example, the same as that in the alkyl, preferably 2 to 8. Examples of the alkynyl include ethynyl, propynyl, and butynyl. The alkynyl may further include, for example, one or more double bonds.

In the present invention, the term "aryl" encompasses, for example, monocyclic aromatic hydrocarbon groups and polycyclic aromatic hydrocarbon groups. Examples of the monocyclic aromatic hydrocarbon group include phenyl. Examples of the polycyclic aromatic hydrocarbon group include 1-naphthyl, 2-naphthyl, 1-anthryl, 2-anthryl, 9-anthryl, 1-phenanthryl, 2-phenanthryl, 3-phenanthryl, 4-phenanthryl, and 9-phenanthryl. Among them, for example, phenyl, naphthyls such as 1-naphthyl and 2-naphthyl, and the like are preferable.

In the present invention, the term "heteroaryl" encompasses, for example, monocyclic aromatic heterocyclic groups and condensed aromatic heterocyclic groups. Examples of the heteroaryl include furyls (e.g., 2-furyl, 3-furyl), thienyls (e.g., 2-thienyl, 3-thienyl), pyrrolyls (e.g., 1-pyrrolyl, 2-pyrrolyl, 3-pyrrolyl), imidazolyls (e.g., 1-imidazolyl, 2-imidazolyl, 4-imidazolyl), pyrazolyls (e.g., 1-pyrazolyl, 3-pyrazolyl, 4-pyrazolyl), triazolyls (e.g., 1,2, 4-triazol-1-yl, 1,2,4-triazol-3-yl, 1,2,4-triazol-4-yl), tetrazolyls (e.g., 1-tetrazolyl, 2-tetrazolyl, 5-tetrazolyl), oxazolyls (e.g., 2-oxazolyl, 4-oxazolyl, 5-oxazolyl), isoxazolyls (e.g., 3-isoxazolyl, 4-isoxazolyl, 5-isoxazolyl), thiazolyls (e.g., 2-thiazolyl, 4-thiazolyl, 5-thiazolyl), thiadiazolyls, isothiazolyls (e.g., 3-isothiazolyl, 4-isothiazolyl, 5-isothiazolyl), pyridyls (e.g., 2-pyridyl, 3-pyridyl, 4-pyridyl), pyridazinyls (e.g., 3-pyridazinyl, 4-pyridazinyl), pyrimidinyls (e.g., 2-pyrimidinyl, 4-pyrimidinyl, 5-pyrimidinyl), furazanyls (e.g., 3-furazanyl), pyrazinyls (e.g., 2-pyrazinyl), oxadiazolyls (e.g., 1,3,4-oxadiazol-2-yl), benzofuryls (e.g., 2-benzo[b]furyl, 3-benzo[b]furyl, 4-benzo[b]furyl, 5-benzo[b]furyl, 6-benzo[b]furyl, 7-benzo[b]furyl), benzothienyls (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzimidazolyls (e.g., 1-benzimidazolyl, 2-benzimidazolyl, 4-benzimidazolyl, 5-benzimidazolyl), dibenzofuryls, benzoxazolyls, benzothiazolyls, quinoxalyls (e.g., 2-quinoxalinyl, 5-quinoxalinyl, 6-quinoxalinyl), cinnolinyls (e.g., 3-cinnolinyl, 4-cinnolinyl, 5-cinnolinyl, 6-cinnolinyl, 7-cinnolinyl, 8-cinnolinyl), quinazolyls (e.g., 2-quinazolinyl, 4-quinazolinyl, 5-quinazolinyl, 6-quinazolinyl, 7-quinazolinyl, 8-quinazolinyl), quinolyls (e.g., 2-quinolyl, 3-quinolyl, 4-quinolyl, 5-quinolyl, 6-quinolyl, 7-quinolyl, 8-quinolyl), phthalazinyls (e.g., 1-phthalazinyl, 5-phthalazinyl, 6-phthalazinyl), isoquinolyls (e.g., 1-isoquinolyl, 3-isoquinolyl, 4-isoquinolyl, 5-isoquinolyl, 6-isoquinolyl, 7-isoquinolyl, 8-isoquinolyl), puryls, pteridinyls (e.g., 2-pteridinyl, 4-pteridinyl, 6-pteridinyl, 7-pteridinyl), carbazolyls, phenanthridinyls, acridinyls (e.g., 1-acridinyl, 2-acridinyl, 3-acridinyl, 4-acridinyl, 9-acridinyl), indolyls (e.g., 1-indolyl, 2-indolyl, 3-indolyl, 4-indolyl, 5-indolyl, 6-indolyl, 7-indolyl), isoindolyls, phenazinyls (e.g., 1-phenazinyl, 2-phenazinyl), and phenothiazinyls (e.g., 1-phenothiazinyl, 2-phenothiazinyl, 3-phenothiazinyl, 4-phenothiazinyl).

In the present invention, the term "cycloalkyl" refers to cyclic saturated hydrocarbon groups, for example, and the number of carbon atoms in the cycloalkyl is, for example, 3 to 15. Examples of the cycloalkyl include cyclopropyl, cyclobutyl, cyclopentyl, cyclohexyl, cycloheptyl, cyclooctyl, bridged cyclic hydrocarbon groups, and spiro hydrocarbon groups. Among them, cyclopropyl, cyclobutyl, cyclopentyl, cyclohexyl, bridged cyclic hydrocarbons, and the like are preferable.

In the present invention, examples of the "bridged cyclic hydrocarbon groups" include bicyclo[2.1.0]pentyl, bicyclo[2.2.1]heptyl, bicyclo[2.2.2]octyl, and bicyclo[3.2.1]octyl, tricyclo[2.2.1.0]heptyl, bicyclo[3.3.1]nonane, 1-adamantyl, and 2-adamantyl.

In the present invention, examples of the "spiro hydrocarbon groups" include spiro[3.4]octyl.

In the present invention, the term "cycloalkenyl" encompasses unsaturated cyclic aliphatic hydrocarbon groups, for example, and the number of carbon atoms in the cycloalkenyl is, for example, 3 to 7. Examples of the cycloalkenyl group include cyclopropenyl, cyclobutenyl, cyclopentenyl, cyclohexenyl, and cycloheptenyl. Among them, cyclopropenyl, cyclobutenyl, cyclopentenyl, cyclohexenyl, and the like are preferable. The term "cycloalkenyl" also encompasses, for example, bridged cyclic hydrocarbon groups and spiro hydrocarbon groups having an unsaturated bond in their rings.

In the present invention, examples of the "arylalkyl" include benzyl, 2-phenethyl, and naphthalenylmethyl. Examples of the "cycloalkylalkyl" and "cyclylalkyl" include cyclohexylmethyl and adamantylmethyl. Examples of the "hydroxyalkyl" include hydroxymethyl and 2-hydroxyethyl.

In the present invention, the "alkoxy" encompasses groups composed of any of the above-described alkyls and oxygen (alkyl-O— groups), for example, and examples thereof include methoxy, ethoxy, n-propoxy, isopropoxy, and n-butoxy. Examples of the "alkoxyalkyl" include methoxymethyl. Examples of the "aminoalkyl" include 2-aminoethyl.

In the present invention, examples of the "heterocyclyl" include 1-pyrrolinyl, 2-pyrrolinyl, 3-pyrrolinyl, 1-pyrrolidinyl, 2-pyrrolidinyl, 3-pyrrolidinyl, pyrrolidinone, 1-imidazolinyl, 2-imidazoliny, 4-imidazoliny, 1-imidazolidinyl, 2-imidazolidinyl, 4-imidazolidinyl, imidazolidinone, 1-pyrazolinyl, 3-pyrazolinyl, 4-pyrazolinyl, 1-pyrazolidinyl, 3-pyrazolidinyl, 4-pyrazolidinyl, piperidinone, piperidino, 2-piperidinyl, 3-piperidinyl, 4-piperidinyl, 1-piperazinyl, 2-piperazinyl, piperazinone, 2-morpholinyl, 3-morpholinyl, morpholino, tetrahydropyranyl, and tetrahydrofuranyl.

In the present invention, examples of the "heterocyclylalkyl" include piperidinylmethyl and piperazinylmethyl. Examples of the "heterocyclylalkenyl" include 2-piperidinyl ethenyl. Examples of the "heteroarylalkyl" include pyridylmethyl and quinolin-3-ylmethyl.

In the present invention, the term "silyl" encompasses groups represented by the formula $R_3Si—$, where R independently can be selected from the above-described alkyls, aryls, and cycloalkyls. Examples of the silyl include a trimethylsilyl group and a tert-butyldimethylsilyl group. Examples of the "silyloxy" include a trimethylsilyloxy group. Examples of the "silyloxyalkyl" include trimethylsilyloxymethyl.

In the present invention, examples of the "alkylene" include methylene, ethylene, and propylene.

In the present invention, the above-described various groups may be substituted. Examples of the substituent include is hydroxy, carboxy, sulfo, halogens, alkyl halides (haloalkyl e.g., $CF_3$, $CH_2CF_3$, $CH_2CCl_3$), nitro, nitroso, cyano, alkyls (e.g., methyl, ethyl, isopropyl, tert-butyl), alkenyls (e.g., vinyl), alkynyls (e.g., ethynyl), cycloalkyls (e.g., cyclopropyl, adamantyl), cycloalkylalkyls (e.g., cyclohexylmethyl, adamantylmethyl), cycloalkenyls (e.g., cyclopropenyl), cyclylalkyl, hydroxyalkyl (e.g., hydroxymethyl, hydroxyethyl), alkoxyalkyl (e.g., methoxymethyl, ethoxymethyl, ethoxyethyl), aryls (e.g., phenyl, naphthyl), arylalkyls (e.g., benzyl, phenethyl), alkylaryl (e.g., p-methylphenyl), heteroaryls (e.g., pyridyl, furyl), heteroarylalkyls (e.g., pyridylmethyl), heterocyclyls (e.g., piperidyl), heterocyclylalkenyl, heterocyclylalkyls (e.g., morpholylmethyl), alkoxys (e.g., methoxy, ethoxy, propoxy, butoxy), halogenated alkoxys (e.g., $OCF_3$), alkenyloxys (e.g., vinyloxy, allyloxy), aryloxys (e.g., phenyloxy), alkyloxycarbonyls (e.g., methoxycarbonyl, ethoxycarbonyl, tert-butoxycarbonyl), arylalkyloxys (e.g., benzyloxy), aminos [alkylaminos (e.g., methylamino, ethylamino, dimethylamino), acylaminos (e.g., acetylamino, benzoylamino), arylalkylaminos (e.g., benzylamino, tritylamino), hydroxyamino], aminoalkyl (e.g., aminomethyl), alkylaminoalkyls (e.g., diethylaminomethyl) carbamoyl, sulfamoyl, oxo, silyl, silyloxyalkyl and the like.

Alternatively, in the artificial sgRNA of the present invention, the aforementioned linker region ($X^a$) is shown by any of the following formulas (III-1)-(III-3). In each formula, n and m are the same as in the aforementioned chemical formula (I):

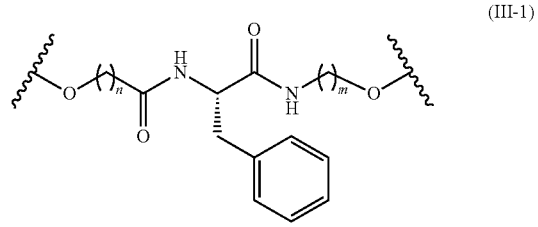

(III-1)

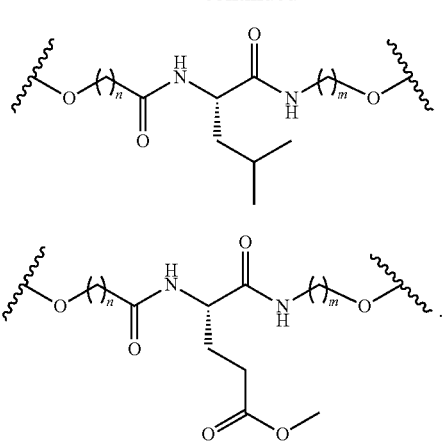

(III-2)

(III-3)

In the aforementioned chemical formulas (III-1) to (III-3), n and m are not particularly limited, and are as described above. Specific examples thereof include n=5 and m=4 (F in Example described later) in the aforementioned chemical formula (III-1), n=5 and m=4 (L in Example described later) in the aforementioned chemical the formula (III-2), and n=5 and m=4 (E in Example described later) in the aforementioned chemical the formula (III-3).

The structures thereof are shown by the following chemical formulas (III-1a), (III-2a) and (III-3a).

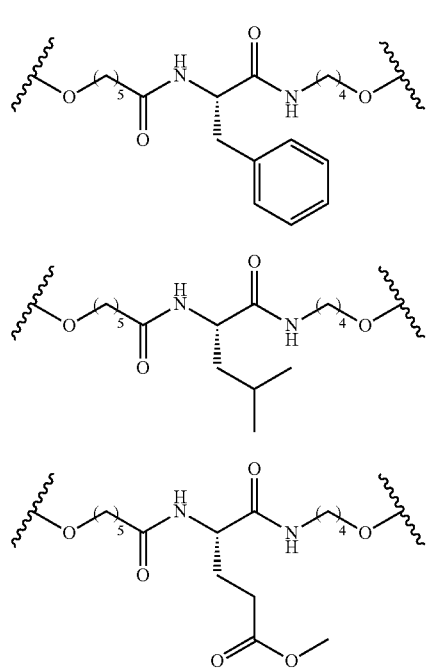

(III-1a)

(III-2a)

(III-3a)

In the artificial sgRNA of the present invention, (1) loop portion (GAAA) of stem-loop 2 and/or (2) linker region (UUAUC) of the natural form sgRNA can be substituted with the amino acid derivative linker (Xb, Y) of the aforementioned formula (I) in addition to the aforementioned amino acid derivative linker (Xa). Alternatively/in addition thereto, the amino acid derivative linker (Xc, Xd) of the aforementioned formula (I) can be added to and/or inserted into the vicinity of (3) 5'-terminal and/or (4) 3'-terminal of the natural form sgRNA. See FIG. 16.

The amino acid derivative linkers $X^b$, Y, $X^c$ and $X^d$ may be each independently, any amino acid derivative represented by the aforementioned formula (I). For example, as the aforementioned $X^b$, a proline derivative linker represented by the aforementioned formula (II) is preferable, and a proline derivative linker (P) represented by the aforementioned formula (II-8) wherein n=5 and m=4 is more preferable.

Alternatively, as the aforementioned $X^b$, a glycine derivative linker (Gly) represented by the aforementioned formula (I-1) wherein n=5 and m=4, a glycylglycine derivative linker (GlyGly) represented by the aforementioned formula (I-4) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 are also preferable.

As the aforementioned Y, a glycylglycine derivative linker represented by the aforementioned formula (I-4) and a proline derivative linker represented by the aforementioned formula (II) are preferable, and a glycylglycine derivative linker (GlyGly) represented by the aforementioned formula (I-4) wherein n=5 and m=4 and a proline derivative linker represented by the aforementioned formula (II-8) wherein n=5 and m=4 (P), n=7 and m=6 (P13), n=9 and m=8 (P14), or n=11 and m=10 (P15) are more preferable.

Alternatively, as the aforementioned Y, a glycine derivative linker (Gly) represented by the aforementioned formula (I-1) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 are also preferable.

As the aforementioned $X^c$ and $X^d$, for example, a proline derivative linker represented by the aforementioned formula (II) is preferable, and a proline derivative linker (P) represented by the aforementioned formula (II-8) wherein n=5 and m=4 is more preferable.

Alternatively, as the aforementioned $X^c$ and $X^d$, a glycine derivative linker (Gly) represented by the aforementioned formula (I-1) wherein n=5 and m=4, a glycylglycine derivative linker (GlyGly) represented by the aforementioned formula (I-4) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 are also preferable.

In one preferable embodiment, the artificial sgRNA of the present invention may be obtained by substituting only the tetraloop portion of the natural form sgRNA with the aforementioned amino acid derivative linker ($X^a$). That is, in the following formula (A), $X^b$ and Y show a nucleotide linker consisting of 1 to 5 optional nucleotide residues and $X^c$ and $X^d$ are absent:

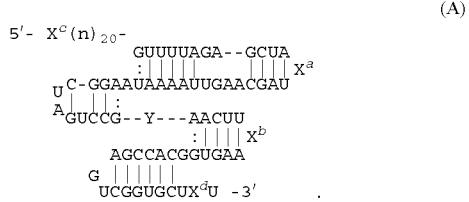

(A)

$X^b$ and Y may respectively remain as the loop portion (GAAA) and the linker region (UUAUC) of the stem-loop 2 of the natural form sgRNA, or may also be replaced with other nucleotide linker as long as the structures of the stem-loop 2 and the linker region in the natural form sgRNA are retained. For example, it has been reported that an equivalent or higher DSB activity can be obtained even when the aforementioned Y is substituted from UUAUC to U alone.

In another preferable embodiment of the artificial sgRNA of the present invention, the loop portion (GAAA) of stem-loop 2 in addition to the tetraloop portion in the natural form sgRNA are substituted with the aforementioned amino acid derivative linker, preferably, a proline derivative linker represented by the aforementioned formula (II), more preferably, proline derivative linker (P) represented by the aforementioned formula (II-8) wherein n=5 and m=4.

Alternatively, an artificial sgRNA wherein the loop portion (GAAA) of stem-loop 2 is substituted with a glycine derivative linker (Gly) represented by the aforementioned formula (I-1) wherein n=5 and m=4, a glycylglycine derivative linker (GlyGly) represented by the aforementioned formula (I-4) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 is also preferable.

The artificial sgRNA of the present invention in which the loop portion (GAAA) of the stem-loop 2 in addition to the tetraloop portion of the natural form sgRNA are substituted with the aforementioned amino acid derivative linker is considered to be more superior due to the in vivo stability improving effect. It is also particularly useful as a tool for in vivo genome editing since it retains a DNA cleavage activity equal to or higher than that of the natural form sgRNA in cells.

In still another preferable embodiment of the artificial sgRNA of the present invention, the linker region (UUAUC) as well as the tetraloop portion and the loop portion (GAAA) of stem-loop 2 in the natural form sgRNA are substituted with the aforementioned amino acid derivative linker, preferably, a glycylglycine derivative linker represented by the aforementioned formula (I-4) and a proline derivative linker represented by the aforementioned formula (II), more preferably, a glycylglycine derivative linker (GlyGly) represented by the aforementioned formula (I-4) wherein n=5 and m=4 and a proline derivative linker represented by the aforementioned formula (II-8) wherein n=5 and m=4 (P), n=7 and m=6 (P13), n=9 and m=8 (P14), or n=11 and m=10 (P15).

Alternatively, an artificial sgRNA in which the linker region (UUAUC) is substituted with a glycine derivative linker (Gly) represented by the aforementioned formula (I-1) wherein n=5 and m=4, a glycylglycine derivative linker (GlyGly) represented by the aforementioned formula (I-4) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 is also preferable.

However, in consideration of the intracellular DNA cleavage activity when combined with Cas9, the artificial sgRNA of the present invention may be preferably free of simultaneous substitution of $X^a$, $X^b$ and Y in the aforementioned formula (A) with an amino acid derivative linker in some cases.

In still another preferable embodiment of the artificial sgRNA of the present invention, the aforementioned amino acid derivative linker, preferably, a proline derivative linker represented by the aforementioned formula (II), more preferably, proline derivative linker (P) represented by the aforementioned formula (II-8) wherein n=5 and m=4 is added to and inserted into the vicinity of the 5'-terminal and 3'-terminal in addition to the tetraloop portion in the natural form sgRNA.

Alternatively, an artificial sgRNA wherein a glycine derivative linker (Gly) represented by the aforementioned formula (I-1) wherein n=5 and m=4, a glycylglycine derivative linker (GlyGly) represented by the aforementioned formula (I-4) wherein n=5 and m=4, a terephthalic acid derivative linker (TP) represented by the aforementioned formula (I-6) wherein n=4 and m=4, a lysine derivative linker (K) represented by the aforementioned formula (I-7) wherein n=5 and m=4, a phenylalanine derivative linker (F) represented by (III-1) wherein n=5 and m=4, a leucine derivative linker (L) represented by the aforementioned formula (III-2) wherein n=5 and m=4, and a glutamic acid derivative linker (E) represented by the aforementioned formula (III-3) wherein n=5 and m=4 are respectively added to and inserted into the vicinity of the 5'-terminal and 3'-terminal is also preferable.

The artificial sgRNA of the present invention in which the aforementioned amino acid derivative linker, preferably, a proline derivative linker represented by the aforementioned formula (II), more preferably, proline derivative linker (P) represented by the aforementioned formula (II-8) wherein n=5 and m=4, is added to and inserted into each of the vicinity of the 5'-terminal and 3'-terminal in addition to the tetraloop portion in the natural form sgRNA is considered to be more superior due to the improvement of stability in vivo and the effect reducing side effect due to the enhanced innate immune response. It is also particularly useful as a tool for in vivo genome editing since it retains a DNA cleavage activity equal to or higher than that of the natural form sgRNA in cells.

As mentioned above, any of the above-mentioned artificial sgRNA into which two or more amino acid derivative linkers are introduced can have, when combined with Cas9 and similar to artificial sgRNA into which an amino acid derivative linker is introduced into $X^a$ alone, a target double-stranded DNA cleavage activity within the cell which is equal to or higher than that of the natural form sgRNA. Introduction of two or more amino acid derivative linkers further improves nuclease resistance of sgRNA and can improve stability in vivo. The effect of improving the stability in vivo can be confirmed, for example, by conducting a resistance test to serum and/or nuclease in vitro.

The artificial sgRNA of the present invention also includes not only the nucleotide sequence shown by the aforementioned formula (A) but also said nucleotide sequence is wherein 1 to several (e.g., 1, 2, 3, 4, 5, 6, 7, 8, 9 or 10) nucleotide residues are substituted, deleted, inserted or added, and showing, when combined with Cas9, a target double-stranded DNA recognizing ability (binding activity) equivalent to or higher than that of the natural form sgRNA. For example, a report has documented that replacement of Watson-Crick base pairs (UUUU/AAAA) between the repeat region and the antirepeat region with CCCC/GGGG, or substitution of Watson-Crick base pairs (ACUU/UGAA) in stem-loop 2 with CGCC/GCGG or insertion of 2 base pairs (ACUUGA/UGAACU) did not result in a significant decrease in the DSB activity when combined with Cas9, and truncation of the linker region (UUAUC) to U alone significantly increased DSB activity. Therefore, the action effect of the artificial sgRNA of the present invention can be exerted even when a mutation maintaining the characteristic hairpin structure of sgRNA is introduced into the nucleotide sequence of the aforementioned formula (A).

According to the study of the present inventors, a truncated sgRNA lacking the 3'-terminal and further the stem-loop 2 and linker region of tracrRNA, without introducing the amino acid derivative linker of the present invention into the natural form sgRNA, showed a significantly decreased DSB activity when combined with Cas9. On the other hand, as shown in the below-mentioned Experimental Example 3, not only the tetraloop of the natural form sgRNA but also 1-3 base pairs of the stem adjacent thereto and/or not only the loop portion of the stem-loop 2 but also 1-4 base pairs of the stem adjacent thereto are substituted with the aforementioned amino acid derivative linker, preferably, a proline derivative linker represented by the aforementioned formula (II), more preferably, proline derivative linker (P) represented by the aforementioned formula (II-8) wherein n=5 and m=4, whereby even a truncated sgRNA can maintain sufficient DSB activity even though inferior to the natural form sgRNA.

In addition, good DSB activity can be maintained when combined with Cas9 by substituting the loop portion of stem-loop 1 or stem-loop 3 in tracrRNA with the aforementioned amino acid derivative linker, preferably, a proline derivative linker represented by the aforementioned formula (II), more preferably, proline derivative linker (P) represented by the aforementioned formula (II-8) wherein n=5 and m=4, without modifying the tetraloop, stem-loop 2 or linker region in tracrRNA or both terminals of sgRNA.

Therefore, the present invention also provides the following artificial sgRNA.
(a) sgRNA represented by the aforementioned formula (A),
(i) wherein $X^a$ is represented by the aforementioned formula (II-8) wherein n=5 and m=4, and 1 to 3 base pairs of the stem adjacent to $X^a$ are deleted, and/or
(ii) wherein $X^b$ is represented by the aforementioned formula (II-8) wherein n=5 and m=4, and 1 to 4 base pairs of the stem adjacent to $X^b$ are deleted;
(b) sgRNA represented by the aforementioned formula (A), wherein $X^a$, $X^b$ and Y are 1 to 5 optional nucleotide linkers, $X^c$ and $X^d$ are absent, and loop portion (UA) of stem-loop 1 or loop portion (AGU) of stem-loop 3 is substituted with an amino acid derivative linker represented by the aforementioned formula (II-8) wherein n=5 and m=4.

The nucleotide residue constituting the artificial sgRNA of the present invention includes, as its components, a sugar, a base, and a phosphate. The nucleotide residue may be, for example, a ribonucleotide residue or a deoxyribonucleotide residue, as described above. The ribonucleotide residue has, for example, a ribose residue as the sugar; and adenine (A), guanine (G), cytosine (C), or uracil (U) as the base. The deoxyribose residue has, for example, a deoxyribose residue as the sugar; and adenine (A), guanine (G), cytosine (C), or thymine (T) as the base.

The aforementioned nucleotide residue may be, for example, an unmodified nucleotide residue or a modified nucleotide residue. The components of the unmodified nucleotide residue are, for example, the same or substantially the same as the components of a naturally-occurring nucleotide residue. Preferably, the components are the same or substantially the same as the components of a nucleotide residue occurring naturally in a human body.

The modified nucleotide residue is, for example, a nucleotide residue obtained by modifying the unmodified nucleotide residue. The modified nucleotide residue may be such that, for example, any of the components of the unmodified nucleotide residue is modified. In the present invention, "modification" means, for example, substitution, addition, and/or deletion of any of the components; and substitution, addition, and/or deletion of an atom(s) and/or a functional group(s) in the component(s). It also can be referred to as "modification". Examples of the modified nucleotide residue include naturally-occurring nucleotide residues and artificially-modified nucleotide residues. Regarding the naturally-derived modified nucleotide residues, for example, Limbach et al. (1994, Summary: the modified nucleosides of RNA, Nucleic Acids Res. 22: pp. 2183 to 2196) can be referred to. The modified nucleotide residue may be, for example, a residue of an alternative of the nucleotide residue.

Examples of the modification of the nucleotide residue include modification of a ribose-phosphate backbone (hereinafter referred to as a "ribophosphate backbone").

In the ribophosphate backbone, for example, a ribose residue may be modified. In the ribose residue, for example, the 2'-position carbon can be modified. Specifically, a hydroxyl group bound to the 2'-position carbon can be, for example, substituted with hydrogen, fluoro, or the like. By substituting the hydroxyl group bound to the 2'-position carbon with hydrogen, it is possible to substitute the ribose residue with deoxyribose residue. The ribose residue can be substituted with its stereoisomer, for example, and may be, for example, substituted with an arabinose residue.

The ribophosphate backbone may be substituted with, for example, a non-ribophosphate backbone having a non-ribose residue and/or a non-phosphate. The non-ribophosphate backbone may be, for example, the ribophosphate backbone modified so as to be uncharged, or the like. Examples of an alternative obtained by substituting the ribophosphate backbone with the non-ribophosphate backbone in the nucleotide residue include morpholino, cyclobutyl, and pyrrolidine. Other examples of the alternative include artificial nucleic acid monomer residues. Specific examples thereof include PNA (Peptide Nucleic Acid), LNA (Locked Nucleic Acid), and ENAs (2'-O,4'-C-Ethylenebridged Nucleic Acids). Among them, PNA is preferable.

In the ribophosphate backbone, for example, a phosphate group can be modified. In the ribophosphate backbone, a phosphate group in the closest proximity to the sugar residue is called an "α-phosphate group". The α-phosphate group is charged negatively, and the electric charges are distributed evenly over two oxygen atoms that are not linked to the sugar residue. Among the four oxygen atoms in the α-phosphate group, the two oxygen atoms not linked to the sugar residue in the phosphodiester linkage between the nucleotide residues hereinafter are referred to as "non-linking oxygens". On the other hand, two oxygen atoms that are linked to the sugar residue in the phosphodiester linkage between the nucleotide residues hereinafter are referred to as "linking oxygens". The α-phosphate group preferably is modified so as to be uncharged, or, for example, so as to render the charge distribution between the non-linking atoms asymmetric.

In the phosphate group, for example, the non-linking oxygen(s) may be substituted. The oxygen(s) can be substituted with any atom selected from S (sulfur), Se (selenium), B (boron) C (carbon), H (hydrogen), N (nitrogen), and OR (R is an alkyl group or an aryl group, for example,), for example, and substitution with S is preferable. It is preferable that both the non-linking oxygens are substituted, for example, and it is more preferable that both the non-linking oxygens are substituted with S. Examples of the thus-modified phosphate group include phosphorothioates, phosphorodithioates, phosphoroselenates, borano phosphates, borano phosphates, hydrogen phosphonates, phosphoroamidates, alkyl or aryl phosphonates, and phosphotriesters. In particular, phosphorodithioate in which both of the two non-linking oxygens are substituted with S is preferable.

In the phosphate group, for example, the linking oxygen(s) may be substituted. The oxygen(s) may be substituted with, for example, any atom selected from S (sulfur), C (carbon), and N (nitrogen). Examples of the thus-modified phosphate group include: bridged phosphoroamidates resulting from the substitution with N; bridged phosphorothioates resulting from the substitution S; and bridged methylene-phosphonates resulting from the substitution C. Preferably, substitution of the linking oxygen(s) is performed, for example, in at least one of the 5' end nucleotide residue and the 3' end nucleotide residue of the artificial sgRNA of the present invention. When the substitution is performed on the 5' side, substitution with C is preferable. When the substitution is performed on the 3' side, substitution with N is preferable.

The phosphate group may be, for example, substituted with the phosphate-free linker. The linker may contain siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo, methyleneoxymethylimino, or the like. Preferably, the linker may contain a methylene carbonyl amino group and a methylenemethylimino group.

In the artificial sgRNA of the present invention, for example, at least one of a nucleotide residue at the 3' end and a nucleotide residue at the 5' end may be modified. The nucleotide residue at either one of the 3' end and the 5' end may be modified or, for example, the nucleotide residues at both the 3' end and the 5' end may be modified. The modification may be as described above, for example, and it is preferable to modify a phosphate group(s) at the end(s). The entire phosphate group may be, for example, modified, or one or more atoms in the phosphate group may be modified. In the former case, for example, the entire phosphate group may be substituted or deleted.

Modification of the nucleotide residue(s) at the end(s) may be, for example, addition of any other molecule, or the like. Examples of the other molecule include functional molecules such as labeling substances as described above and protecting groups. Examples of the protecting groups include S (sulfur), Si (silicon), B (boron), and ester-containing groups.

The other molecule may be, for example, added to the is phosphate group of the nucleotide residue, or may be added to the phosphate group or the sugar residue via a spacer. The terminal atom of the spacer can be, for example, added to or substituted for either one of the linking oxygens of the phosphate group, or O, N, S or C of the sugar residue. The binding site in the sugar residue preferably is, for example, C at the 3'-position, C at the 5'-position, or any atom bound thereto. The spacer also can be added to, for example, or substituted for a terminal atom of the nucleotide alternative such as PNA.

The spacer is not particularly limited, and examples thereof include —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH, abasic sugars, amide, carboxy, amine, oxyamine, oxyimine, thioether, disulfide, thiourea, sulfonamide, and morpholino, and also biotin reagents and fluorescein reagents. In the above formulae, n is a positive integer, and n=3 or 6 is preferable.

Other examples of the molecule to be added to the end include dyes, intercalating agents (e.g., acridines), crosslinking agents (e.g., psoralen, mitomycin C), porphyrins (TPPC4, texaphyrin, Sapphyrin), polycyclic aromatic hydrocarbons (e.g., phenazine, dihydrophenazine), artificial endonucleases (e.g., EDTA), lipophilic carriers (e.g., cholesterol, cholic acid, adamantane acetic acid, 1-pyrene butyric acid, dihydrotestosterone, 1,3-Bis-O (hexadecyl) glycerol, a geranyloxyhexyl group, hexadecylglycerol, borneol, menthol, 1,3-propanediol, a heptadecyl group, palmitic acid, myristic acid, O3-(oleoyl)lithocholic acid, O3-(oleoyl) cholic acid, dimethoxytrityl, or phenoxazine), peptide complexes (e.g., Antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens is (e.g., biotin), transport/absorption facilitators (e.g., aspirin, vitamin E, folic acid), and synthetic ribonucleases (e.g., imidazole, bisimidazole, histamine, imidazole clusters, acridine-imidazole complexes, Eu$^{3+}$ complexes of tetraazamacrocycles).

In the artificial sgRNA of the present invention, for example, the 5' end may be modified with a phosphate group or a phosphate group analog. Examples of the phosphate group include:

5'-monophosphate((HO)$_2$(O)P—O-5'); 5'-diphosphate((HO)$_2$(O)P—O—P(HO) (O)—O-5'); 5'-triphosphate (HO)$_2$(O)P—O—(HO) (O)P—O—P(HO) (O)—O-5');

5'-guanosine cap (7-methylated or non-methylated, 7m-G-O-5'-(HO) (O)P—O—(HO) (O)P—O—P(HO) (O)—O-5');

5'-adenosine cap (Appp);

any modified or unmodified nucleotide cap structure (N—O-5'-(HO) (O)P—O—(HO) (O)P—O—P(HO) (O)—O-5');

5'-monothiophosphate (phosphorothioate: (HO)$_2$(S)P—O-5');

5'-monodithiophosphate (phosphorodithioate: (HO) (HS) (S)P—O-5');

5'-phosphorothiolate ((HO)$_2$(O)P—S-5');

sulfur substituted monophosphate, diphosphate, and triphosphates (e.g., 5'-α-thiotriphosphate, 5'-γ-thiotriphosphate, and the like);

5'-phosphoramidates ((HO)$_2$(O)P—NH-5', (HO)(NH$_2$)(O)P—O-5'); 5'-alkylphosphonates (e.g., RP(OH) (O)—O-5', (OH)$_2$(O)P-5'-CH$_2$, where R is alkyl (e.g., methyl, ethyl, isopropyl, propyl, or the like)); and 5'-alkyletherphosphonates (e.g., RP(OH) (O)—O-5', where R is alkylether (e.g., methoxymethyl, ethoxymethyl, or the like)).

In the nucleotide residue, the base is not particularly limited. The base may be, for example, a natural base or a non-natural base. The base may be, for example, a naturally-derived base or a synthetic base. As the base, for example, a common (universal) base, a modified analog thereof, and the like can be used.

Examples of the base include: purine bases such as adenine and guanine; and pyrimidine bases such as cytosine, uracil, and thymine. Other examples of the base include inosine, thymine, xanthine, hypoxanthine, nubularine, isoguanisine, and tubercidine. Examples of the base also include: alkyl derivatives such as 2-aminoadenine, 6-methylated purine, and 2-propylated purine; 5-halouracil and 5-halocytosine; 5-propynyl uracil and 5-propynyl cytosine; 6-azo uracil, 6-azo cytosine, and 6-azo thymine; 5-uracil (pseudouracil), 4-thiouracil, 5-halouracil, 5-(2-aminopropyl)uracil, 5-amino allyl uracil; 8-halogenated, aminated, thiolated, thioalkylated, hydroxylated, and other 8-substituted purines; 5-trifluoromethylated and other 5-substituted pyrimidines; 7-methylguanine; 5-substituted pyrimidines; 6-azapyrimidines; N-2, N-6, and O-6 substituted purines (including 2-aminopropyladenine); 5-propynyluracil and 5-propynylcytosine; dihydrouracil; 3-deaza-5-azacytosine; 2-aminopurine; 5-alkyluracil; 7-alkylguanine; 5-alkylcytosine; 7-deazaadenine; N6,N6-dimethyladenine; 2,6-diaminopurine; 5-amino-allyl-uracil; N3-methyluracil; substituted 1,2,4-triazoles; 2-pyridinone; 5-nitroindole; 3-nitropyrrole; 5-methoxyuracil; uracil-5-oxyacetic acid; 5-methoxycarbonylmethyluracil; 5-methyl-2-thiouracil; 5-methoxycarbonylmethyl-2-thiouracil; 5-methylaminomethyl-2-thiouracil; 3-(3-amino-3-carboxypropyl)uracil; 3-methylcytosine; 5-methylcytosine; N4-acetylcytosine; 2-thiocytosine; N6-methyladenine; N6-isopentyladenine; 2-methylthio-N6-isopentenyladenine; N-methylguanine; and O-alkylated bases. Examples of the purines and pyrimidines include those disclosed in U.S. Pat. No. 3,687,808, "Concise Encyclopedia of Polymer Science and Engineering", pp. 858 to 859, edited by Kroschwitz J. I, John Wiley & Sons, 1990, and Englisch et al, Angewandte Chemie, International Edition, 1991, vol. 30, p. 613.

Other examples of the modified nucleotide residue include those having no base, i.e., those having an abasic ribophosphate backbone. Furthermore, as the modified nucleotide residue, those described in U.S. Provisional Application 60/465,665 (filing date: Apr. 25, 2003) and International Application No. PCT/US04/07070 (filing date: Mar. 8, 2004) can be used, for example, and these documents are incorporated herein by reference.

The artificial sgRNA of the present invention can be, for example, a modified form in which any functional molecule is added via a non-nucleotide residue such as an amino acid derivative linker by the method described in WO 2013/180038.

2. Synthesis Method of Artificial sgRNA of the Present Invention

The method for synthesizing the artificial sgRNA of the present invention is not particularly limited, and a conventionally known method can be employed. Examples thereof include a phosphoramidite method and an H-phosphonate method. The chemical synthesis methods can be carried out, for example, using a commercially available automated nucleic acid synthesizer. In the chemical synthesis methods, an amidite generally is used. The amidite is not particularly limited. Examples of commercially available amidites include RNA Phosphoramidites (2'-O-TBDMSi, trade name, Samchully Pharm. Co., Ltd.), ACE amidite, TOM amidite, CEE amidite, CEM amidite, and TEM amidite. In the synthesis of the artificial sgRNA of the present invention, for example, it is preferable to use the monomer of the present invention to be described below for the synthesis of the linker region(s) represented by the formula (I).

3. Monomer of the Present Invention

The monomer according to the present invention is a monomer for nucleic acid synthesis, having the structure of the following formula (IV):

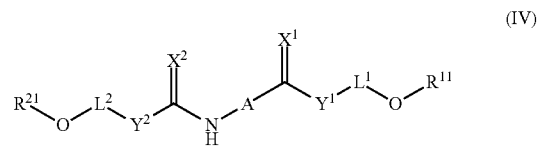

wherein $X^1$, $X^2$, $Y^1$, $Y^2$, $L^1$, $L^2$ and A are as defined for the aforementioned formula (I), and $R^{11}$ and $R^{21}$ are each independently a hydrogen atom, a protecting group or a phosphoric acid protecting group.

In $R^{11}$ and $R^{21}$, for example, the protecting group is as described above regarding the formula (I). Specifically, for example, the protecting group can be selected from Group I. Group I includes, for example, a dimethoxytrityl (DMTr) group, a TBDMS group, an ACE group, a TOM group, a CEE group, a CEM group, a TEM group, and silyl-containing groups (group I) represented by the following formula (P1) or (P2). In particular, it is preferable that the protecting group is the DMtr group or any of the silyl-containing groups.

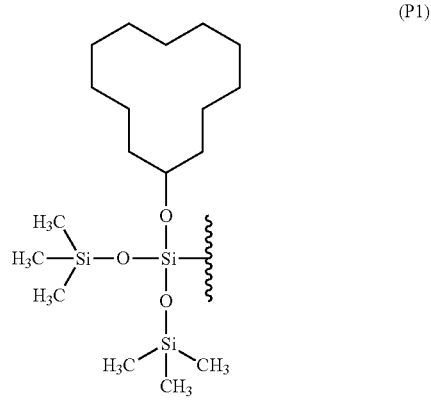

(P2)

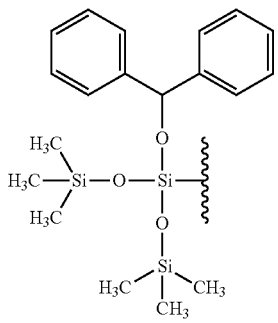

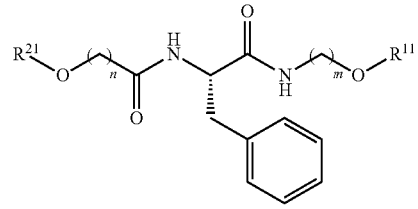
(IV-1)

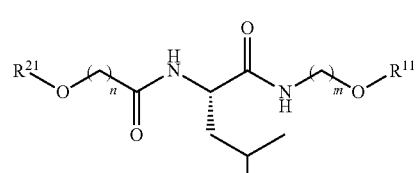
(IV-2)

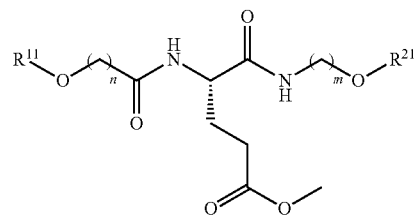
(IV-3)

The phosphate-protecting group can be represented, for example, by the following formula:

—P(OR$^6$)(NR$^7$R$^8$).

In the formula, R$^6$ is a hydrogen atom or any substituent. The substituent R$^6$ preferably is a hydrocarbon group and, for example, the hydrocarbon group may or may not be substituted with an electron-withdrawing group. Examples of the substituent R$^6$ include halogens, haloalkyls, heteroaryls, hydroxyalkyls, alkoxyalkyls, aminoalkyls, silyls, silyloxyalkyls, heterocyclylalkenyls, heterocyclylalkyls, heteroarylalkyls, and hydrocarbons such as alkyls, alkenyls, alkynyls, aryls, arylalkyls, cycloalkyls, cycloalkenyls, cycloalkylalkyls, and cyclylalkyls. Furthermore, the substituent R$^6$ may or may not be substituted with an electron-withdrawing group. Specific examples of the substituent R$^6$ include a β-cyanoethyl group, a nitrophenylethyl group, and a methyl group.

R$^7$ and R$^8$ are each a hydrogen atom or any substituent, and they may be the same or different. The substituents R$^7$ and R$^8$ preferably are each a hydrocarbon group, and the hydrocarbon group may or may not be substituted with any substituent. Examples of the hydrocarbon group are the same as those listed in the above description regarding R$^6$, and the hydrocarbon group preferably is a methyl group, an ethyl group, or an isopropyl group. In this case, specific examples of —NR$^7$R$^8$ include a diisopropylamino group, a diethylamino group, and an ethylmethylamino group. Alternatively, the substituents R$^7$ and R$^8$ together (i.e., —NR$^7$R$^8$ as a whole) may form a nitrogen-containing ring (e.g., a piperidyl group, a morpholino group, or the like) with a nitrogen atom(s) to which they bind.

As specific example of the above-mentioned phosphate-protecting group, for example, —P(OCH$_2$CH$_2$CN)(N(i-Pr)$_2$), —P(OCH$_3$)(N(i-Pr)$_2$) and the like (group II) can be mentioned. In the above formulae, i-Pr indicates isopropyl.

In the formula (IV), for example, one of R$^{11}$ and R$^{21}$ is a hydrogen atom or a protecting group, and the other is a hydrogen atom or a phosphate-protecting group. For example, it is preferable that, when R$^{11}$ is a protecting group, R$^{21}$ is a hydrogen atom or a phosphate-protecting group. Specifically, it is preferable that, when R$^{11}$ is selected from Group I, R$^{21}$ is a hydrogen atom or is selected from Group II. Also, it is preferable that, for example, when R$^{11}$ is a phosphate-protecting group, R$^{21}$ is a hydrogen atom or a protecting group. Specifically, it is preferable that, when R$^{11}$ is selected from Group II, R$^{21}$ is a hydrogen atom or is selected from Group I.

As the monomer of the present invention, specifically, for example, the monomer described in WO 2013/103146 and the like, and the monomers represented by the following formulas (IV-1)-(IV-3) can be mentioned.

(in each formula, R$^{11}$ and R$^{21}$ are as defined for the aforementioned formula (IV), and n and m are each independently an integer of 0-30.)

The monomer of the present invention can be synthesized, for example, the method described in WO 2013/103146 and the like, or the method described in the below-mentioned Examples.

4. CRISPR/Cas9 System

The present invention also provides a CRISPR/Cas9 system combining the above-mentioned artificial sgRNA of the present invention and Cas9.

Cas9 used in the present invention is not particularly limited as long as it forms a complex with the artificial sgRNA of the present invention and can recognize and bind to the target nucleotide sequence in the target double-stranded DNA and the proto-spacer adjacent motif (PAM) adjacent thereto. *Streptococcus pyogenes*-derived Cas9 (SpCas9; PAM sequence NGG (N is A, G, T or C, hereinafter the same)), as long as a complex with the artificial sgRNA of the present invention can be formed, *Streptococcus thermophiles*-derived Cas9 (StCas9; PAM sequence NNAGAAW), *Neisseria meningitidis*-derived Cas9 (MmCas9; PAM sequence NNNNGATT) and the like can be preferably used. SpCas9 which is less restricted by PAM is particularly preferable (it is substantially 2 bases and can theoretically be targeted almost anywhere on the genome). As Cas9 used in the present invention, in addition to wild-type Cas9 capable of cleaving both strands of double-stranded DNA, one having nickase activity resulted from inactivation of the cleavage ability of one chain (nCas9) can also be used. For example, in the case of SpCas9, a D10A mutant in which the 10th Asp residue is converted to Ala residue and lacking the cleavage ability of a strand opposite to the strand forming a complementary strand with sgRNA, and a H840A mutant in which the 840th His residue is converted to Ala residue and lacking the cleavage ability of the strand forming a complementary strand with sgRNA can be mentioned, though not limited thereto. Furthermore, depending on the use object, a double mutant lacking cleavage ability of both strands (dCas9) can also be used. Specific examples of the embodiments using dCas9 and nCas9 include, but are not limited to, fusing a transcriptional regulatory factor or a chromatin modulator with dCas9/nCas9 to control the transcription of a target gene and visualizing the target locus by fusing a fluorescent protein (live imaging) and the like.

In addition, Cpf1 can also be used instead of Cas9. Examples of the Cpf1 include, but are not limited to, *Francisella novicida*-derived Cpf1 (FnCpf1; PAM sequence NTT), *Acidaminococcus* sp.-derived Cpf1 (AsCpf1; PAM sequence NTTT), *Lachnospiraceae bacterium*-derived Cpf1 (LbCpf1; PAM sequence NTTT) and the like. In the case of Cpf1, it is also possible to use mutants lacking cleavage activity of one or both strands. For example, in the case of FnCpf1, a mutant (dCpf1) in which the 917th Asp residue is converted to Ala residue (D917A) or the 1006th Glu residue is converted to Ala residue (E1006A), and lacking the cleavage ability of the both strands can be used.

Cas9 to be used in the CRISPR/Cas9 system of the present invention may be in the form of a protein or mRNA encoding the protein. Alternatively, it may be in the form of an expression vector containing a DNA encoding Cas9. When the CRISPR/Cas9 system is performed as an enzyme reaction of a cell-free system, Cas 9 is provided in the form of a protein. On the other hand, when modification of a target gene in a cell is aimed, Cas9 can be introduced into a cell in any form of a protein, an mRNA encoding the protein, and an expression vector containing a DNA encoding the same.

DNA encoding Cas9 can be cloned, for example, by amplifying same by RT-PCR method using total RNA or mRNA fraction prepared from the cell producing the protein as a template. A mutant Cas9 can be obtained by introducing a mutation into a DNA encoding the cloned Cas9 by using a site-specific mutagenesis method known per se, so as to convert the amino acid residue at the site important for the DNA cleavage activity (e.g., in the case of Cas9, the 10th Asp residue and the 840th His residue can be mentioned, though not limited thereto) with other amino acid. Alternatively, the DNA encoding Cas9 can also be constructed as DNA having codon usage suitable for expression in a host cell to be used, in combination with chemical synthesis or PCR method or Gibson Assembly method. For example, CDS sequences optimized for expression of SpCas9 in eukaryotic cells are well known.

DNA encoding the obtained Cas9 can be inserted into the downstream of the promoter of a suitable expression vector according to the host. An expression vector can be introduced by a known method (e.g., lysozyme method, competent method, PEG method, CaCl$_2$ coprecipitation method, electroporation method, microinjection method, particle gun method, lipofection method, *Agrobacterium* method and the like) according to the kind of the host.

The artificial sgRNA of the present invention and Cas9 can be introduced into a host cell preferably by a nucleofection method.

The sgRNA introduced (and expressed) in the cell forms a complex with the Cas9 protein and binds to the target sequence to induce DSB in the target gene. The DSB is repaired by non-homologous end joining (NHEJ), but the target gene is destroyed (knockout) by a frameshift mutation due to accidental insertion or deletion (indel) of base(s) occurring at that time. In addition, co-transfection of a donor DNA having a sequence homologous to the target at both ends results in homologous recombination repair, thus enabling base modification and gene insertion (knockin).

The present invention is explained in detail in the following by referring to Examples and the like, which are not to be construed as limitative.

EXAMPLE (Example 1) Synthesis of sgRNAs sgRNAs shown in Table 1 were synthesized based on a phosphoramidite method and using a nucleic acid synthesizer (The ABI Expedite® 8909 Nucleic Acid Synthesis System, Applied Biosystems). As RNA amidite, EMM amidite (WO 2013/027843) was used in the aforementioned synthesis (hereinafter the same). Deprotection of the aforementioned amidite was performed according to a conventional method, and sgRNA was purified by HPLC. In the following sequences, the underlined part is a guide region complementary to the target nucleotide sequence, proline diamide amidite was introduced into P, lysine diamide amidite was introduced into K, and glycylglycine diamide amidite was introduced into X.

TABLE 1

| ID | Sequence (5'-3') | SEQ ID NO: |
|---|---|---|
| SG-0001 | GUAGUUGGAGCUGUUGGCGUGUUUUAGAGCUAGAAAUAGCAAGUUAAAAUAAGGCUAGUCCGUUAUCAACUUGAAAAAGUGGCACCGAGUCGGUGCUUU | 4 |
| SG-0002 | GUAGUUGGAGCUGUUGGCGUGUUUUAGAGCUA-P-UAGCAAGUUAAAAUAAGGCUAGUCCGUUAUCAACUUGAAAAAGUGGCACCGAGUCGGUGCUUU | 5 |
| SG-0012 | GUAGUUGGAGCUGUUGGCGUGUUUUAGAGCUA-K-UAGCAAGUUAAAAUAAGGCUAGUCCGUUAUCAACUUGAAAAAGUGGCACCGAGUCGGUGCUUU | 6 |
| SG-0013 | GUAGUUGGAGCUGUUGGCGUGUUUUAGAGCUA-X-UAGCAAGUUAAAAUAAGGCUAGUCCGUUAUCAACUUGAAAAAGUGGCACCGAGUCGGUGCUUU | 7 |
| SG-0014 | GUAGUUGGAGCUGUUGGCGUGUUUUAGAGCUA-P-UAGCAAGUUAAAAUAAGGCUAGUCCGUUAUCAACUU-P-AAGUGGCACCGAGUCGGUGCUUU | 8 |
| SG-0015 | GUAGUUGGAGCUGUUGGCGUGUUUUAGAGCUA-P-UAGCAAGUUAAAAUAAGGCUAGUCCG-X-AACUU-P-AAGUGGCACCGAGUCGGUGGUUU | 9 |
| SG-0016 | P-GUAGUUGGAGCUGUUGGCGUGUUUUAGAGCUA-P-UAGCAAGUUAAAAUAAGGCUAGUCCGUUAUCAACUUGAAAAAGUGGCACCGAGUCGGUGCU-P-U | 10 |
| SG-0017 | AAGCGUCCCCGCGCGGUGAAGUUUUAGAGCUAGAAAUAGCAAGUUAAAAUAAGGCUAGUCCGUUAUCAACUUGAAAAAGUGGCACCGAGUCGGUGCUUU | 11 |
| SG-0018 | AAGCGUCCCCGCGCGGUGAAGUUUUAGAGCUA-P-UAGCAAGUUAAAAUAAGGCUAGUCCGUUAUCAACUUGAAAAAGUGGCACCGAGUCGGUGCUUU | 12 |
| SG-0019 | AAGCGUCCCCGCGCGGUGAAGUUUUAGAGCUA-K-UAGCAAGUUAAAAUAAGGCUAGUCCGUUAUCAACUUGAAAAAGUGGCACCGAGUCGGUGCUUU | 13 |
| SG-0020 | AAGCGUCCCCGCGCGGUGAAGUUUUAGAGCUA-X-UAGCAAGUUAAAAUAAGGCUAGUCCGUUAUCAACUUGAAAAAGUGGCACCGAGUCGGUGCUUU | 14 |
| SG-0021 | AAGCGUCCCCGCGCGGUGAAGUUUUAGAGCUA-P-UAGCAAGUUAAAAUAAGGCUAGUCCGUUAUCAACUU-P-AAGUGGCACCGAGUCGGUGCUUU | 15 |

TABLE 1-continued

| ID | Sequence (5'-3') | SEQ ID NO: |
|---|---|---|
| SG-0022 | AAGCGUCCCCGCGCGGUGAAGUUUUAGAGCUA-P-UAGCAAGUUAAAAUAAGGCUAGUCCG-X-AACUU-P-AAGUGGCACCGAGUCGGUGCUUU | 16 |

(Experimental Example 1) Evaluation of In Vitro Cleavage Activity of sgRNA Targeting KRAS Gene Plasmid DNA (pCMV6-Entry-KRAS (G12V), OriGene Technologies) incorporating a sequence (NCBI Refference Sequence NP_0049762) having a G12V mutation in human KRAS gene (GenBank accession No. NM_004985.3) was reacted with restriction enzyme Tth111I (TaKaRa) according to the attached protocol. After completion of the reaction, the DNA of interest was purified according to a conventional method and dissolved in TE buffer (10 mM Tris-HCl, pH 8, 1 mM EDTA) to a final concentration of 100 ng/μL to give a substrate DNA.

The above-mentioned substrate DNA was mixed with sgRNA and Cas9 as follows using the reagent attached to Cas9 Nuclease, *S. pyogenes* (New England Biolabs);

100 ng substrate DNA+10 ng sgRNA+0.3 pmol Cas9 (total amount 10 μL)

This was incubated at 37° C. for 30 min, and further incubated at 70° C. for 10 min to inactivate Cas9. Thereafter, electrophoresis was performed and, after ethidium bromide staining, the band intensity was measured using gel imaging system PXi4 (SYNGENE).

Based on the measurement results, the cleavage efficiency was calculated by the following equation.

Cleavage Efficiency=sum of cleaved band intensities/
(sum of the cleaved and uncleaved band intensities)

Figure 1:
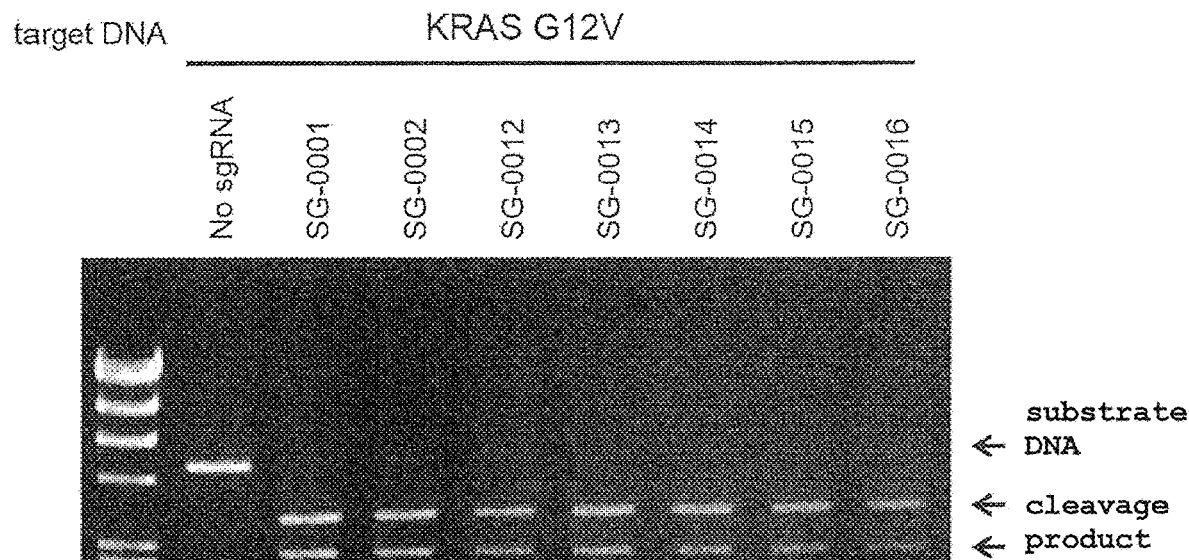
FIG. 1 shows the in vitro cleavage activity of sgRNA targeting KRAS gene.
Figure 1:
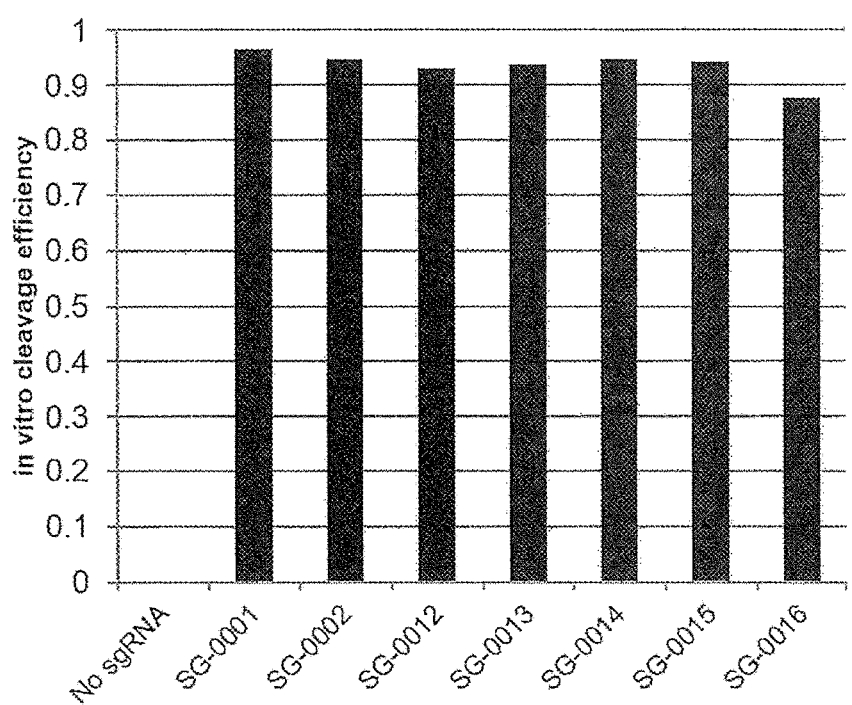

The results are shown in FIG. 1. All artificial sgRNAs showed a cleavage efficiency equivalent to that of the natural form sgRNA (SG-0001).

(Experimental Example 2) Evaluation of In Vitro Cleavage Activity of sgRNA Targeting BCL-2 Gene Plasmid DNA (pCAGGS-hbcl-2, Iwahashi et. al., Nature, vol 390, pp 414-417, 1997) incorporating human BCL-2 gene (GenBank accession No. NM_000633) was reacted with restriction enzyme HindIII (TaKaRa) according to the attached protocol. After completion of the reaction, the DNA of interest was purified according to a conventional method and dissolved in TE buffer (10 mM Tris-HCl, pH 8, 1 mM EDTA) to a final concentration of 100 ng/μL to give a substrate DNA.

The above-mentioned substrate DNA was mixed with sgRNA and Cas9 as follows using the reagent attached to Cas9 Nuclease, *S. pyogenes* (New England Biolabs);

100 ng substrate DNA+10 ng sgRNA+0.3 pmol Cas9 (total amount 10 μL)

This was incubated at 37° C. for 30 min, and further incubated at 70° C. for 10 min to inactivate Cas9. Thereafter, electrophoresis was performed and, after ethidium bromide staining, the band intensity was measured using gel imaging system PXi4 (SYNGENE).

Based on the measurement results, the cleavage efficiency was calculated by the following equation.

Cleavage Efficiency=sum of cleaved band intensities/
(sum of the cleaved and uncleaved band intensities)

Figure 2:
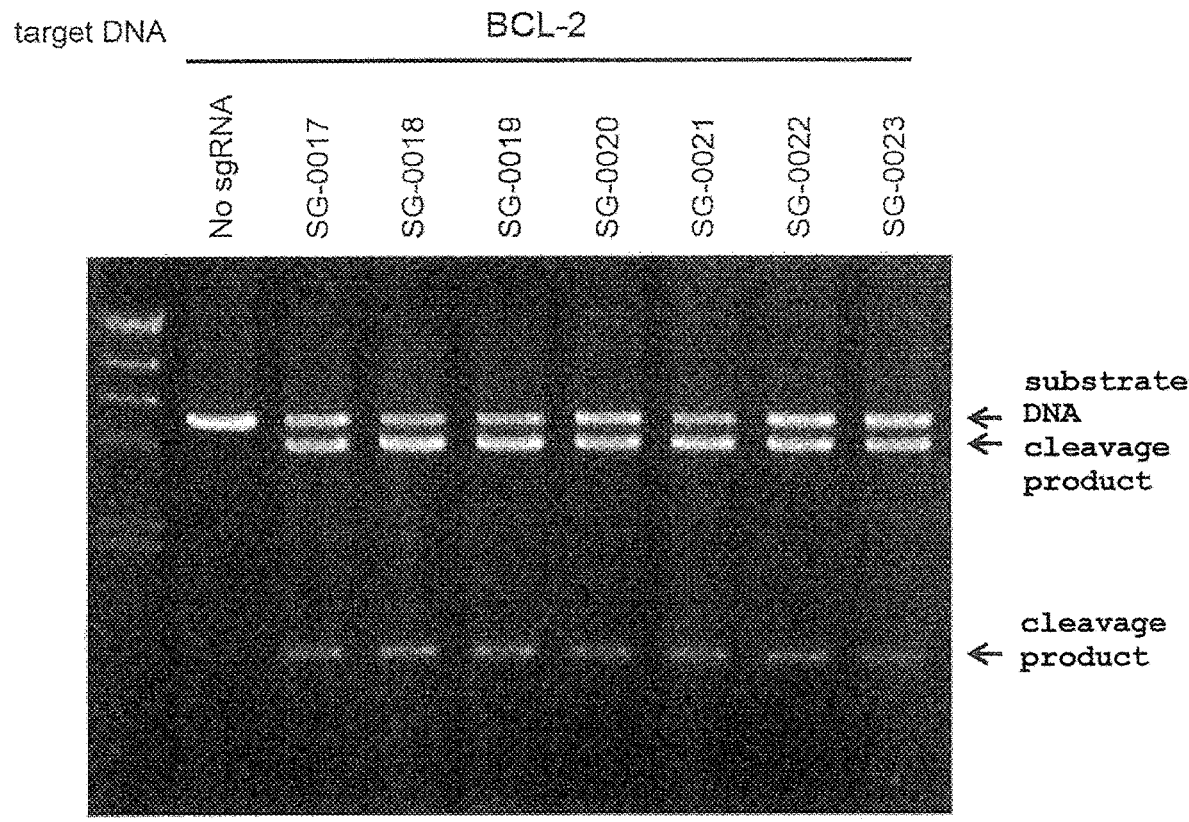
FIG. 2 shows the in vitro cleavage activity of sgRNA targeting BCL-2 gene.
Figure 2:
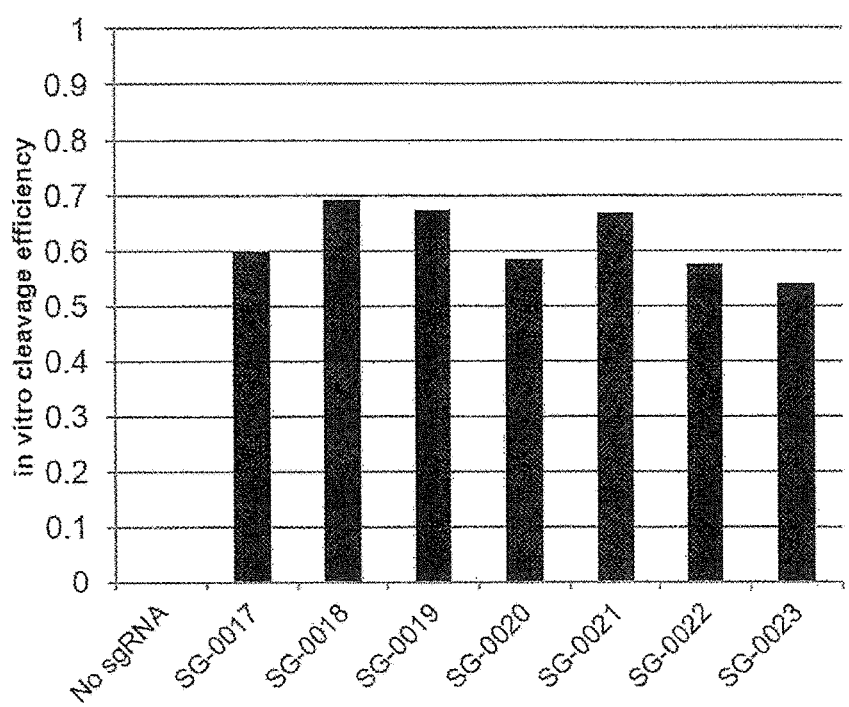
Figure 3:
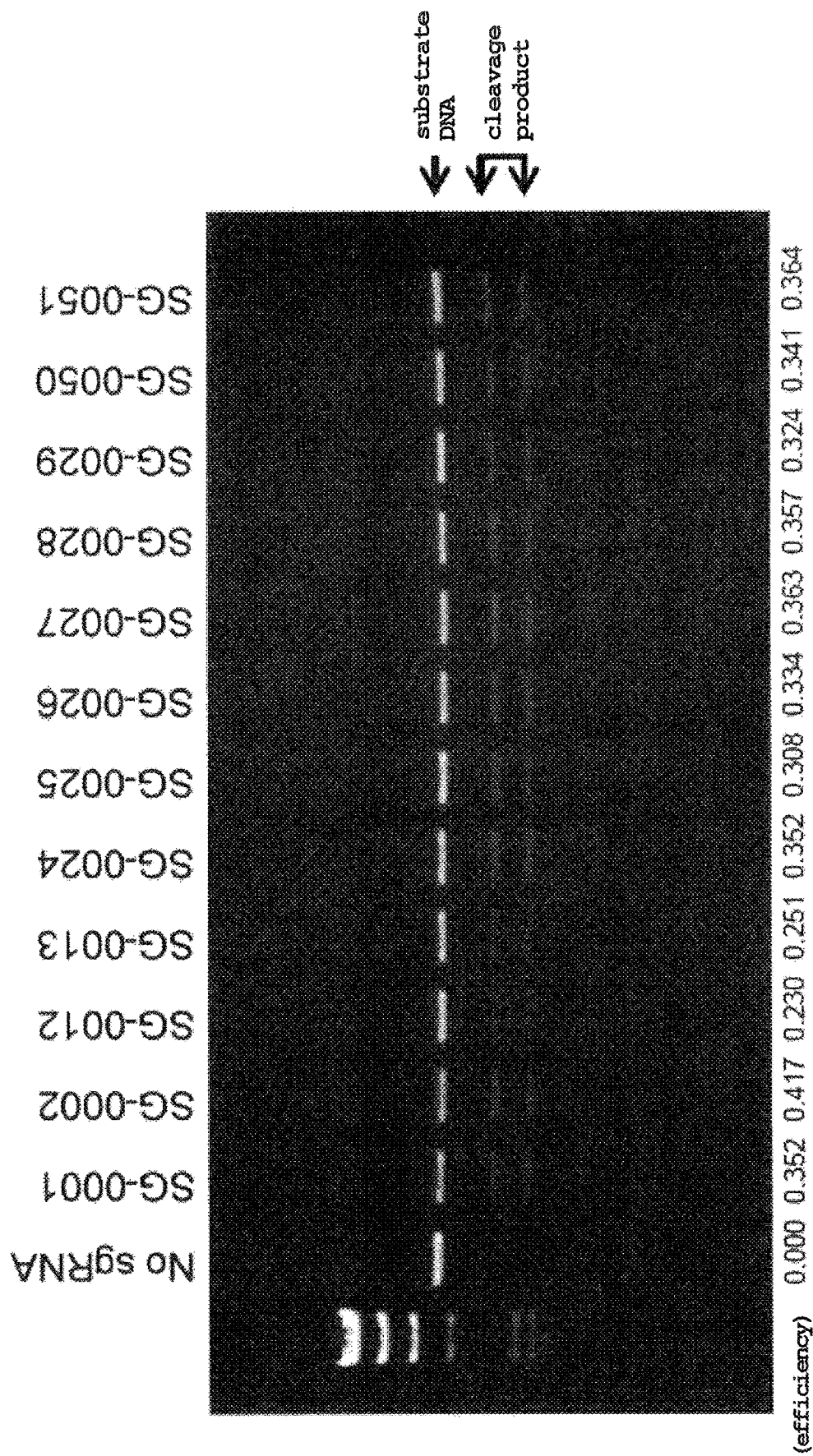
FIG. 3 shows the in vitro cleavage activity of sgRNA targeting KRAS gene.
Figure 4:
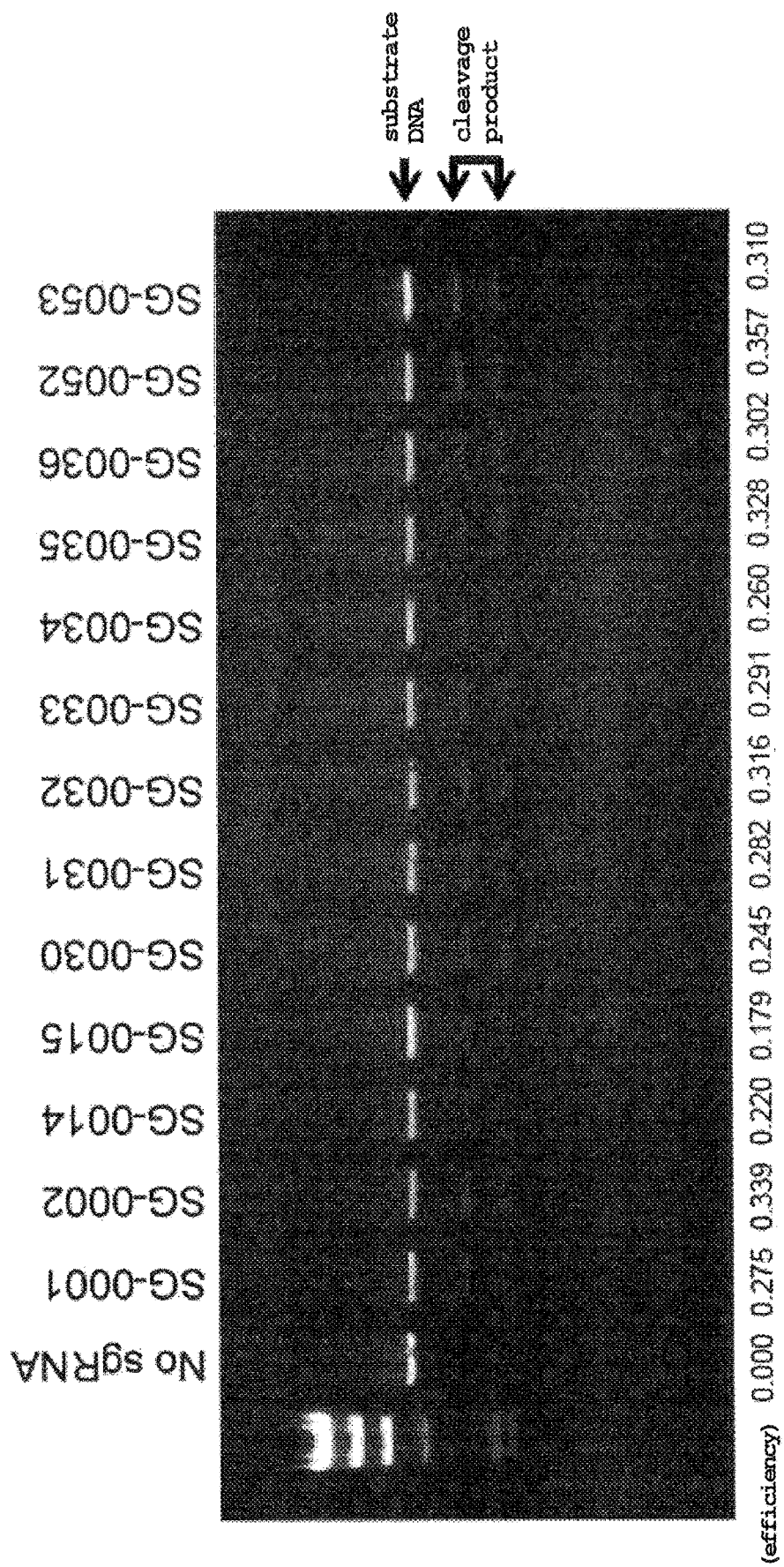
FIG. 4 shows the in vitro cleavage activity of sgRNA targeting KRAS gene.
Figure 5:
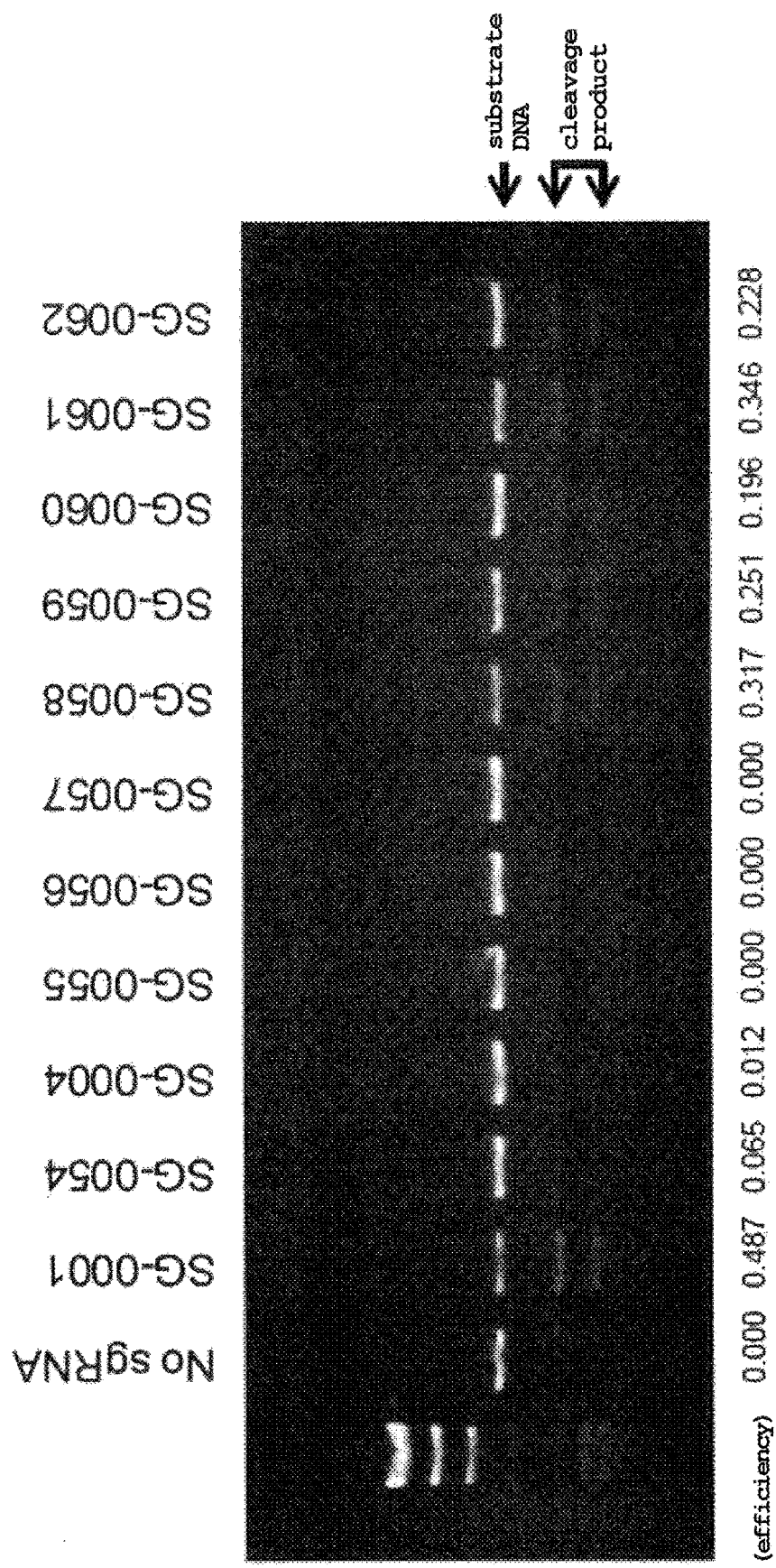
FIG. 5 shows the in vitro cleavage activity of sgRNA targeting KRAS gene.
Figure 6:
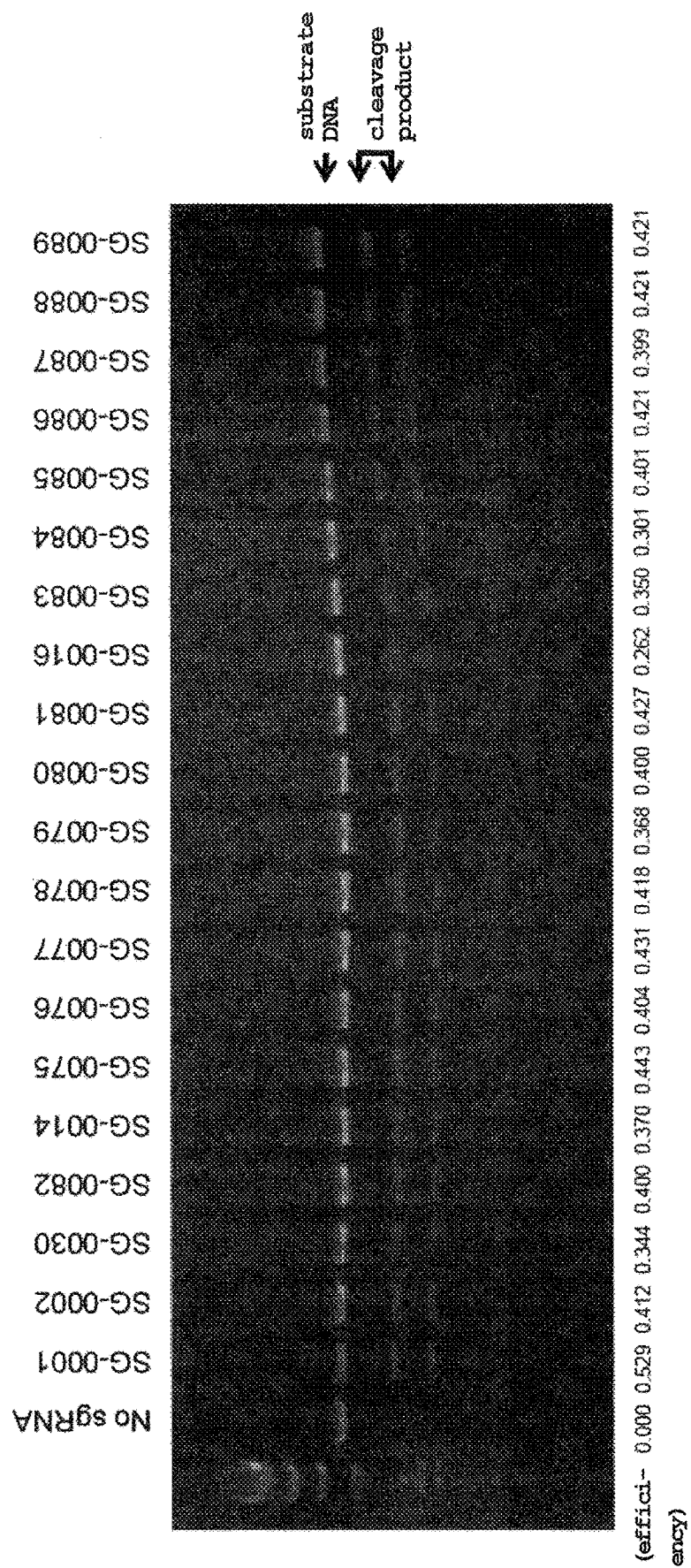
FIG. 6 shows the in vitro cleavage activity of sgRNA targeting KRAS gene.

The results are shown in FIG. 2. All artificial sgRNAs showed a cleavage efficiency equivalent to or higher than that of the natural form sgRNA (SG-0017).

(Example 2) Synthesis of Phenylalanine Amidite: Compound (5)

According to the following scheme, compound (5) was synthesized.

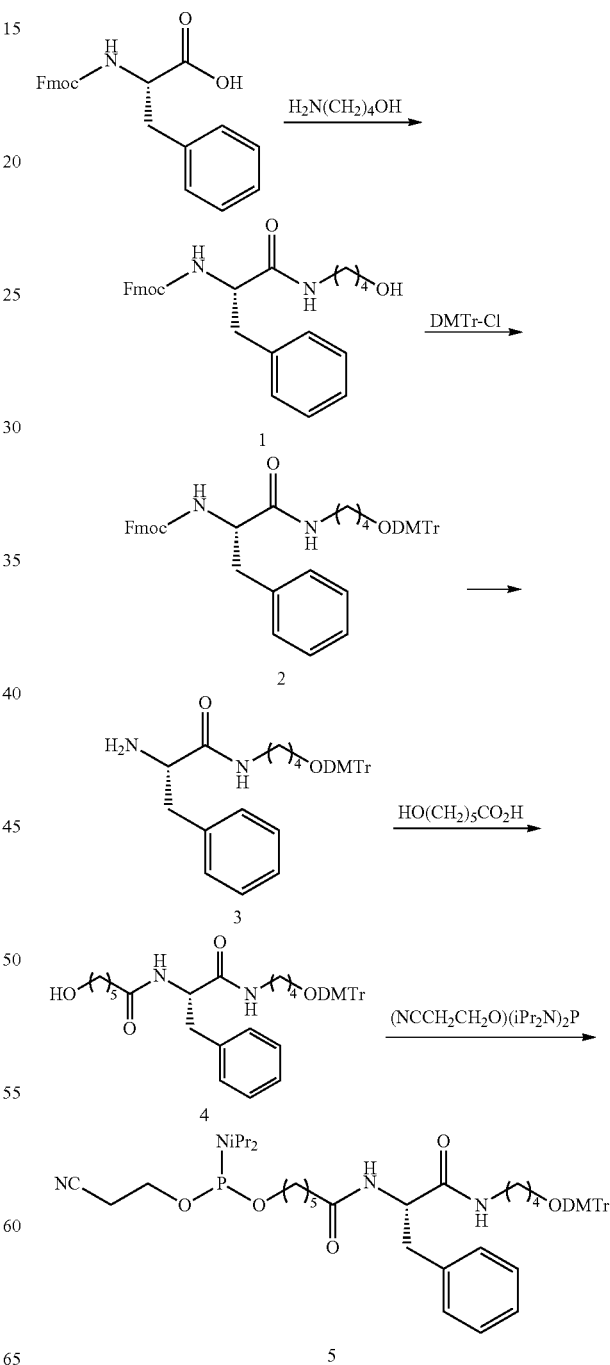

[[1] Synthesis of Compound (1)]

To a solution (100 mL) of Fmoc-phenylalanine (3.0 g, 7.7 mmol), 1-ethyl-3-(3-dimethylaminopropyl) carbodiimide hydrochloride (EDC) (1.78 g, 9.3 mmol) and 1-hydroxybenzotriazole monohydrate (HOBt) (2.51 g, 18.6 mmol) in acetonitrile was added 4-amino-1-butanol (0.83 g, 9.3 mmol) and the mixture was stirred at room temperature overnight. After completion of the reaction, the solvent was evaporated under reduced pressure. To the residue was added dichloromethane, and the mixture was washed twice with saturated aqueous sodium hydrogen carbonate solution and once with saturated aqueous sodium chloride solution. The washed organic layer was dried over anhydrous sodium sulfate and concentrated under reduced pressure to give a crude product (4.1 g) of the object compound (1).

[[2] Synthesis of Compound (2)]

Compound (1) (4.1 g, 8.9 mmol) was azeotropically distilled with pyridine and vacuum dried. The compound was dissolved in pyridine (80 mL), 4,4'-dimethoxytrityl chloride (4.54 g, 13.4 mmol) was added and the mixture was stirred at room temperature overnight. After completion of the reaction, methanol was added and the mixture was stirred for 30 min and the solvent was evaporated under reduced pressure. To the residue was added ethyl acetate, and the mixture was washed twice with saturated aqueous sodium hydrogen carbonate solution and once with saturated aqueous sodium chloride solution. The washed organic layer was dried over anhydrous sodium sulfate and concentrated under reduced pressure to give a crude product (9.8 g) of the object compound (2).

[[3] Synthesis of Compound (3)]

To compound (2) (9.8 g, 12.9 mmol) were added N,N-dimethylformamide (50 mL) and piperidine (8.9 mL) at room temperature, and the mixture was stirred at room temperature overnight. After completion of the reaction, the solvent was evaporated under reduced pressure, and the obtained residue was purified by silica gel column chromatography (dichloromethane:methanol=20:1, containing 0.05% pyridine) to give the object compound (3) (3.1 g, yield after three-steps 74%).

[[4] Synthesis of Compound (4)]

Compound (3) (3.1 g, 5.8 mmol) was azeotropically distilled with pyridine and vacuum dried. Under an argon atmosphere, 6-hydroxyhexanoic acid (0.91 g, 6.9 mmol), 1-ethyl-3-(3-dimethylaminopropyl)carbodiimide hydrochloride (EDC) (1.32 g, 6.9 mmol), 1-hydroxybenzotriazole monohydrate (HOBt) (1.87 g, 13.8 mmol) and dichloromethane (40 mL) were added at room temperature, and the mixture was stirred for 10 min. After stirring, triethylamine (2.1 g, 20.7 mmol) was added, and the mixture was stirred at room temperature overnight. To the obtained residue was added dichloromethane, and the mixture was washed twice with saturated aqueous sodium bicarbonate solution and with saturated aqueous sodium chloride solution. The washed organic layer was dried over anhydrous sodium sulfate and concentrated under reduced pressure. The obtained crude product was purified by silica gel column chromatography (hexane:ethyl acetate=1:2, containing 0.05% pyridine) to give the object compound (4) (2.0 g, yield 53%). The instrument analytical value of compound (4) is shown below.

Compound (4):

$^1$H-NMR (500 MHz, CDCl$_3$) δ: 7.41-7.39 (2H, m), 7.30-7.16 (12H, m), 6.84-6.80 (4H, m), 6.26 (1H, d, J=7.4 Hz), 5.71-5.69 (1H, m), 4.57-4.52 (1H, m), 3.79 (6H, s), 3.64-3.58 (2H, m), 3.18-3.15 (1H, m), 3.09-2.93 (5H, m), 2.19-2.16 (2H, m), 1.64-1.58 (2H, m), 1.56-1.50 (2H, m), 1.46-1.39 (4H, m), 1.36-1.30 (2H, m).

[[5] Synthesis of Compound (5)]

Compound (4) (2.0 g, 3.1 mmol) was azeotropically distilled with pyridine, and vacuum dried. Then, acetonitrile (4 mL) and diisopropylammoniumtetrazolide (0.63 g, 3.7 mmol) were added, 2-cyanoethyl-N,N,N',N'-tetraisopropylphosphordiamidite (1.1 g, 3.7 mmol) was further added, and the mixture was stirred at 40° C. for 2 hr. After completion of the reaction, the solvent was evaporated under reduced pressure, ethyl acetate was added, and the mixture was washed twice with saturated aqueous sodium hydrogen carbonate solution and once with saturated aqueous sodium chloride solution. The washed organic layer was dried over anhydrous sodium sulfate, and concentrated under reduced pressure. The obtained crude product was purified by silica gel column chromatography (hexane:ethyl acetate=1:1, containing 0.1% triethylamine) to give the object compound (5) (2.4 g, purity 97.5%, yield 92%).

The instrument analytical value of compound (5) is shown below.

Compound (5):

$^1$H-NMR (500 MHz, CDCl$_3$) δ: 7.41-7.40 (2H, m), 7.33-7.16 (12H, m), 6.86-6.80 (4H, m), 6.28 (1H, d, J=7.7 Hz), 5.77 (1H, t, J=6.0 Hz), 4.58-4.54 (1H, m), 3.87-3.80 (1H, m), 3.79-3.74 (1H, m), 3.78 (6H, s), 3.67-3.53 (4H, m), 3.21-3.15 (1H, m), 3.10-2.94 (5H, m), 2.62 (2H, t, J=6.4 Hz), 2.18-2.12 (2H, m), 1.64-1.55 (4H, m), 1.46-1.39 (4H, m), 1.36-1.31 (2H, m), 1.17 (12H, m).

$^{31}$P-NMR (202 MHz, CDCl$_3$) δ: 147.95, 147.91

ESI-Mass:871.49 [M+H$_2$O+H]$^+$ (Example 3) Synthesis of Leucine Amidite: Compound (10)

According to the following scheme, compound (10) was synthesized.

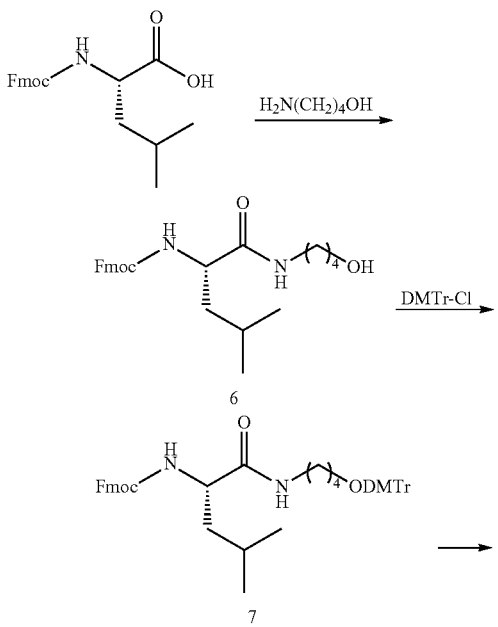

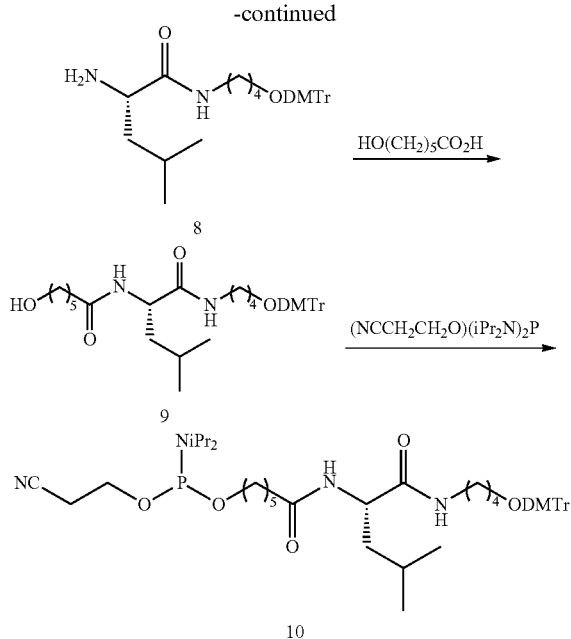

[[1] Synthesis of Compound (6)]

To a solution (90 mL) of Fmoc-leucine (3.0 g, 8.5 mmol), 1-ethyl-3-(3-dimethylaminopropyl)carbodiimide hydrochloride (EDC) (1.95 g, 10.2 mmol) and 1-hydroxybenzotriazole monohydrate (HOBt) (2.75 g, 20.4 mmol) in acetonitrile was added 4-amino-1-butanol (0.91 g, 10.2 mmol) and the mixture was stirred at room temperature overnight. After completion of the reaction, the solvent was evaporated under reduced pressure. To the residue was added dichloromethane, and the mixture was washed twice with saturated aqueous sodium hydrogen carbonate solution, and once with saturated aqueous sodium chloride solution. The washed organic layer was dried over anhydrous sodium sulfate and concentrated under reduced pressure to give a crude product (4.42 g) of the object compound (6).

[[2] Synthesis of Compound (7)]

Compound (6) (4.42 g, 10.4 mmol) was azeotropically distilled with pyridine, and vacuum dried. The compound was dissolved in pyridine (80 mL), 4,4'-dimethoxytrityl chloride (5.29 g, 15.6 mmol) was added and the mixture was stirred at room temperature overnight. After completion of the reaction, methanol was added and the mixture was stirred for 30 min, and the solvent was evaporated under reduced pressure. To the is residue was added ethyl acetate, and the mixture was washed twice with saturated aqueous sodium hydrogen carbonate solution, and once with saturated aqueous sodium chloride solution. The washed organic layer was dried over anhydrous sodium sulfate and concentrated under reduced pressure to give a crude product (9.51 g) of the object compound (7).

[[3] Synthesis of Compound (8)]

To compound (7) (9.51 g, 13.1 mmol) were added N,N-dimethylformamide (40 mL) and piperidine (9.0 mL) at room temperature, and the mixture was stirred at room temperature overnight. After completion of the reaction, the solvent was evaporated under reduced pressure, and the obtained residue was purified by silica gel column chromatography (dichloromethane:methanol=30:1, containing 0.05% pyridine and chloromethane:methanol=40:1, containing 0.05% pyridine) to give the object compound (8) (3.89 g, yield after three-steps 91%).

[[4] Synthesis of Compound (9)]

Compound (8) (3.89 g, 7.7 mmol) was azeotropically distilled with pyridine, and vacuum dried. Under an argon atmosphere, 6-hydroxyhexanoic acid (1.22 g, 9.2 mmol), 1-ethyl-3-(3-dimethylaminopropyl)carbodiimide hydrochloride (EDC) (1.77 g, 9.2 mmol), 1-hydroxybenzotriazole monohydrate (HOBt) (2.50 g, 18.5 mmol) and dichloromethane (50 mL) were added at room temperature, and the mixture was stirred for 10 min. After stirring, triethylamine (2.81 g, 27.7 mmol) was added and the mixture was stirred at room temperature overnight. To the obtained residue was added dichloromethane, and the mixture was washed twice with saturated aqueous sodium bicarbonate solution and with saturated aqueous sodium chloride solution. The washed organic layer was dried over anhydrous sodium sulfate, and concentrated under reduced pressure. The obtained crude product was purified by silica gel column chromatography (hexane:ethyl acetate=1:4, containing 0.05% pyridine) to give the object compound (9) (3.80 g, yield 80%). The instrument analytical value of compound (9) is shown below.

Compound (9):

$^1$H-NMR (500 MHz, CDCl$_3$) δ: 7.42-7.41 (2H, m), 7.31-7.27 (6H, m), 7.21-7.18 (1H, m), 6.83-6.80 (4H, m), 6.21 (1H, t, J=5.7 Hz), 6.05 (1H, d, J=8.3 Hz), 4.41-4.36 (1H, m), 3.78 (6H, s), 3.64-3.59 (2H, m), 3.31-3.15 (2H, m), 3.06 (2H, t, J=6.0 Hz), 2.20 (2H, t, J=7.4 Hz), 1.78 (1H, t, J=5.5 Hz), 1.68-1.47 (10H, m), 1.40-1.34 (2H, m), 0.93-0.91 (6H, m).

[[5] Synthesis of Compound (10)]

Compound (9) (3.80 g, 6.1 mmol) was azeotropically distilled with pyridine, and vacuum dried. Then, acetonitrile (7.6 mL) and diisopropylammoniumtetrazolide (1.26 g, 7.4 mmol) were added, 2-cyanoethyl-N,N,N',N'-tetraisopropylphosphordiamidite (2.22 g, 7.4 mmol) was further added, and the mixture was stirred at 40° C. for 2 hr. After completion of the reaction, the solvent was evaporated under reduced pressure, ethyl acetate was added and the mixture was washed twice with saturated aqueous sodium hydrogen carbonate solution and once with saturated aqueous sodium chloride solution. The washed organic layer was dried over anhydrous sodium sulfate, and concentrated under reduced pressure. The obtained crude product was purified by silica gel column chromatography (hexane:ethyl acetate=1:1, containing 0.1% triethylamine) to give the object compound (10) (4.80 g, purity 97.5%, yield 95.4%). The instrument analytical value of compound (10) is shown below.

Compound (10):

$^1$H-NMR (500 MHz, CDCl$_3$) δ: 7.42-7.40 (2H, m), 7.31-7.26 (6H, m), 7.21-7.18 (1H, m), 6.83-6.81 (4H, m), 6.29 (1H, t, J=5.6 Hz), 6.09 (1H, d, J=8.5 Hz), 4.42-4.37 (1H, m), 3.87-3.74 (2H, m), 3.78 (6H, s), 3.68-3.51 (4H, m), 3.29-3.23 (1H, m), 3.19-3.14 (1H, m), 3.06 (2H, t, J=5.7 Hz), 2.62 (2H, t, J=6.2 Hz), 2.19 (2H, t, J=8.0 Hz), 1.69-1.50 (8H, m), 1.40-1.35 (2H, m), 1.30-1.21 (2H, m), 1.17 (12H, m), 0.94-0.91 (6H, m).

$^{31}$P-NMR (202 MHz, CDCl$_3$) δ: 147.95

ESI-Mass:841.47 [M+Na]$^+$ (Example 4) Synthesis of Glutamic Acid Amidite: Compound (15)

According to the following scheme, compound (15) was synthesized.

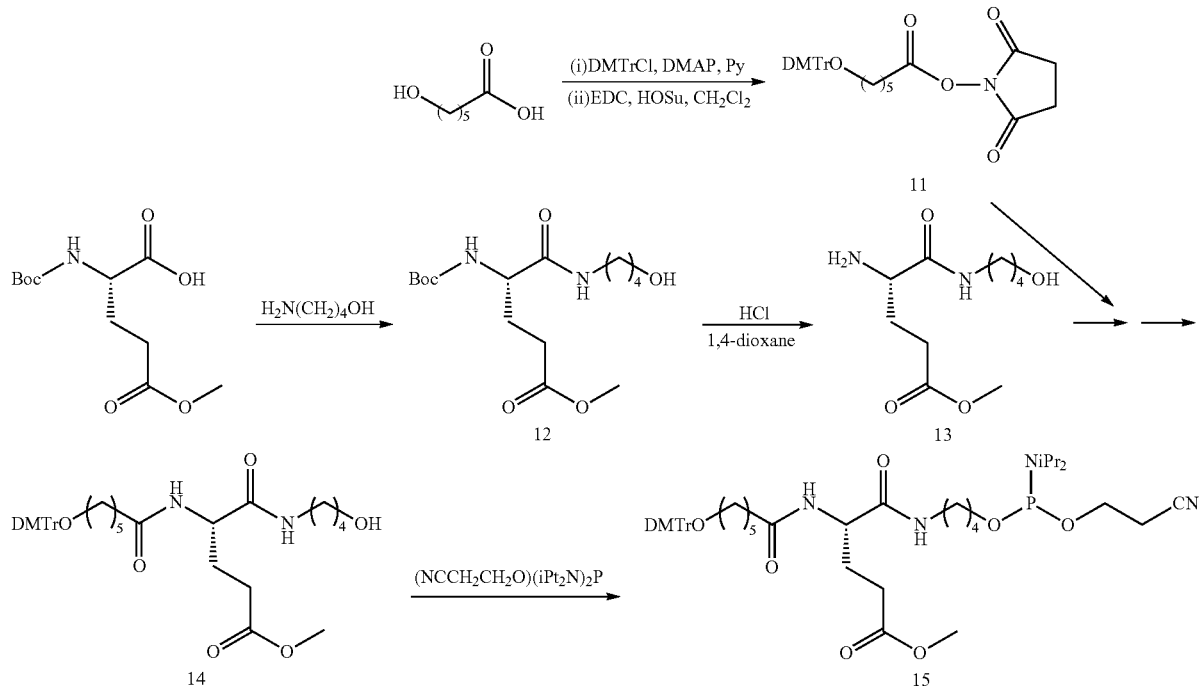

[[1] Synthesis of Compound (11)]

To a solution (25 ml) of 6-hydroxyhexanoic acid (1.00 g, 7.6 mmol) and dimethylaminopyridine (DMAP) (92 mg, 0.8 mmol) in pyridine was added 4,4'-dimethoxytrityl chloride (2.6 g, 7.6 mmol) and the mixture was stirred at room temperature for 5 hr. After confirming the disappearance of the starting materials by TLC, methanol was added and the mixture was stirred for 30 min. The solvent was evaporated under reduced pressure, dichloromethane was added and the mixture was washed three times with saturated aqueous sodium hydrogen carbonate solution and once with saturated brine. The organic layer was dried over sodium sulfate, concentrated under reduced pressure, triturated with hexane, and dried under reduced pressure to give an oily crude product. To the oily crude product was added dichloromethane (32 mL), 1-ethyl-3-(3-dimethylaminopropyl)carbodiimide hydrochloride (EDC) (2.48 g, 13.0 mmol) and N-hydroxysuccinimide (1.49 g, 13.0 mmol) were added and the mixture was stirred at room temperature overnight. After completion of the reaction, the solvent was evaporated under reduced pressure, ethyl acetate was added, and the mixture was washed three times with saturated sodium hydrogen carbonate solution and once with saturated brine. The organic layer was dried over sodium sulfate, and the solvent was evaporated under reduced pressure to give a crude product (3.40 g) of the object compound (11).

[[2] Synthesis of Compound (12)]

To a solution (40 mL) of Boc-glutamic acid (OMe) (2.0 g, 7.7 mmol), 1-ethyl-3-(3-dimethylaminopropyl)carbodiimide hydrochloride (EDC) (1.76 g, 9.2 mmol) and 1-hydroxybenzotriazole monohydrate (HOBt) (2.48 g, 18.4 mmol) in acetonitrile was added 4-amino-1-butanol (0.82 g, 9.2 mmol) and the mixture was stirred at room temperature overnight. After completion of the reaction, the solvent was evaporated under reduced pressure. To the residue was added dichloromethane, and the mixture was washed twice with saturated aqueous sodium hydrogen carbonate solution, and once with saturated aqueous sodium chloride solution. The washed organic layer was dried over anhydrous sodium sulfate and concentrated under reduced pressure to give a crude product (2.30 g) of the object compound (12).

[[3] Synthesis of Compound (13)]

Compound (12) (2.30 g, 6.9 mmol) was dissolved in 1,4-dioxane (23 ml) by adding the solvent thereto, and hydrochloric acid (2.3 ml) was added at 0° C. The mixture was warmed to room temperature and stirred for 30 min. After completion of the reaction, the solvent was evaporated under reduced pressure, the residue was triturated with isopropylether and dried under reduced pressure to give a crude product (2.06 g) of the object compound (13).

[[4] Synthesis of Compound (14)]

To a solution (9 ml) of compound (13) (0.93 g, 4.0 mmol) in DMF were added triethylamine (0.61 g, 6.0 mmol) and a solution (9 ml) of compound (11) (2.34 g, 4.4 mmol) in DMF and the mixture was stirred at room temperature overnight. After completion of the reaction, the solvent was evaporated under reduced pressure, to the residue was added dichloromethane and the mixture was washed 3 times with saturated brine. The washed organic layer was dried over anhydrous sodium sulfate, and the solvent was evaporated under reduced pressure. The obtained crude product was purified by silica gel column chromatography (ethyl acetate, containing 0.05% pyridine). This reaction was performed twice to give the object compound (14) (0.85 g). The instrument analytical value of compound (14) is shown below.

Compound (14):

$^1$H-NMR (500 MHz, CDCl$_3$) δ: 7.43-7.41 (2H, m), 7.32-7.26 (6H, m), 7.21-7.18 (1H, m), 6.87-6.85 (1H, m), 6.83-6.80 (4H, m), 6.51 (1H, d, J=7.3 Hz), 4.43-4.38 (1H, m), 3.79 (6H, s), 3.67 (3H, s), 3.63 (2H, d, J=6.1 Hz), 3.28-3.25 (2H, m), 3.02 (2H, t, J=6.6 Hz), 2.54-2.48 (1H, m), 2.38-2.32 (1H, m), 2.20-2.17 (2H, m), 2.14-2.07 (1H, m), 1.96-1.89 (1H, m), 1.64-1.53 (8H, m), 1.40-1.34 (2H, m)

[[5] Synthesis of Compound (15)]

Compound (14) (0.85 g, 1.3 mmol) was azeotropically distilled with pyridine, and vacuum dried. Then, acetonitrile (2.5 mL) and diisopropylammoniumtetrazolide (0.27 g, 1.6 mmol) were added, 2-cyanoethyl-N,N,N',N'-tetraisopropylphosphordiamidite (0.47 g, 1.6 mmol) was further added and the mixture was stirred at room temperature for 2 hr. After completion of the reaction, the solvent was evaporated under reduced pressure, ethyl acetate was added, and the mixture was washed twice with saturated aqueous sodium hydrogen carbonate solution and once with saturated aqueous sodium chloride solution. The washed organic layer was dried over anhydrous sodium sulfate, and concentrated under reduced pressure. The obtained crude product was purified by silica gel column chromatography (hexane:ethyl acetate=1:2, containing 0.1% triethylamine) to give the object compound (15) (0.95 g, purity 92%, yield 86.4%). The instrument analytical value of compound (15) is shown below.

Compound (15):

$^1$H-NMR (500 MHz, CDCl$_3$) δ: 7.43-7.41 (2H, m), 7.32-7.26 (6H, m), 7.21-7.17 (1H, m), 6.83-6.80 (4H, m), 6.63-6.60 (1H, m), 6.47 (1H, d, J=7.4 Hz), 4.44-4.40 (1H, m), 3.88-3.82 (1H, m), 3.80-3.75 (1H, m), 3.78 (6H, s), 3.71-3.67 (1H, m), 3.66 (3H, s), 3.64-3.55 (3H, m), 3.31-3.21 (2H, m), 3.03 (2H, t, J=6.4 Hz), 2.64 (2H, t, J=6.4 Hz), 2.53-2.47 (1H, m), 2.38-2.32 (1H, m), 2.18 (2H, t, J=7.5 Hz), 2.14-2.07 (1H, m), 1.96-1.89 (1H, m), 1.64-1.56 (8H, m), 1.41-1.34 (2H, m), 1.19-1.16 (12H, m).

$^{31}$P-NMR (202 MHz, CDCl$_3$) δ: 147.89

ESI-Mass:867.49 [M+H$_2$O+H]$^+$ (Example 5) Synthesis of Proline Amidites: Compounds (5a-c)

According to the following scheme, compounds (5a-c) were synthesized.

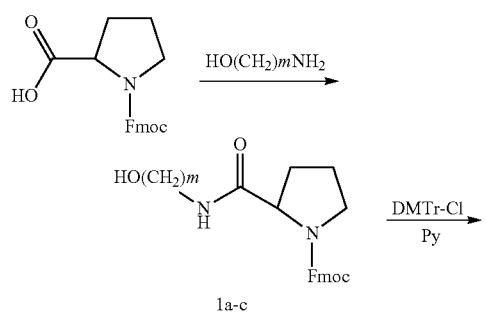

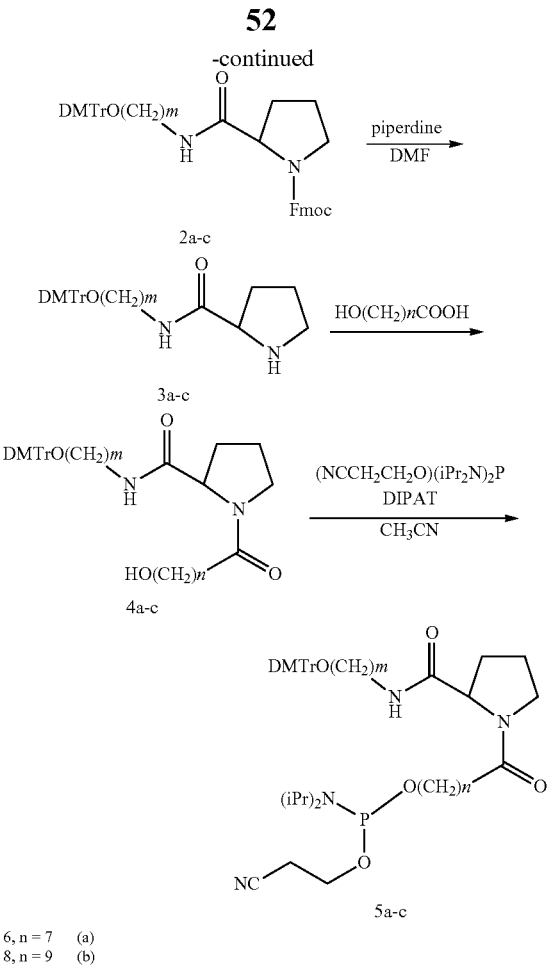

m = 6, n = 7    (a)
m = 8, n = 9    (b)
m = 10, n = 11  (c)

[[1] Synthesis of Compound (1a)]

Fmoc-L-proline (3.0 g, 8.9 mmol) was dissolved in dehydrated N,N-dimethylformamide (50 mL). 6-Amino-1-hexanol (1.3 g, 1.2 eq), 1-ethyl-3-(3-dimethylaminopropyl)carbodiimide hydrochloride (2.0 g, 1.2 eq) and 1-hydroxybenzotriazole (3.3 g, 2.4 eq) were added and the mixture was stirred under an argon atmosphere at room temperature overnight. After completion of the reaction, the solvent was evaporated under reduced pressure from the reaction mixture. To the obtained residue was added dichloromethane, and the mixture was washed with saturated aqueous sodium bicarbonate solution and with saturated brine. The organic phase was dried over sodium sulfate, and the solvent was evaporated. The obtained residue was subjected to silica is gel column chromatography (eluent: dichloromethane-methanol (20:1)) to give the object substance (2.9 g, yield 75%).

$^1$H-NMR (CDCl$_3$): δ7.76-7.83 (m, 2H), 7.50-7.63 (m, 2H), 7.38-7.43 (m, 2H), 7.27-7.34 (m, 2H), 4.54-4.35 (m, 2H), 4.13-4.35 (m, 2H), 3.54-3.63 (m, 2H), 3.35-3.54 (m, 2H), 3.17-3.28 (m, 2H), 1.82-2.07 (m, 3H), 1.21-1.59 (m, 9H)

[[2] Synthesis of Compound (2a)]

Compound 1a (2.9 g, 6.6 mmol) was azeotropically dried using dehydrated pyridine. The residue was dissolved in dehydrated pyridine (40 mL). 4,4-Dimethoxytritylchloride (DMTrCl) (2.7 g, 1.2 eq.) was added at 0° C. and the mixture was stirred at room temperature overnight. After confirming the disappearance of the starting materials by TLC, methanol was added and the mixture was stirred for 30 min. The solvent was evaporated under reduced pressure. To the obtained residue was added dichloromethane, and the mixture was washed with saturated aqueous sodium bicarbonate solution and with saturated brine. The organic phase was dried over sodium sulfate and the solvent was evaporated. The residue was dried under reduced pressure to give an oily substance (5.0 g).

[[3] Synthesis of Compound (3a)]

Compound 2a (5.0 g, 6.6 mmol) was dissolved in dehydrated N,N-dimethylformamide (40 mL). Piperidine (6.5 mL) was added, and the mixture was stirred under an argon atmosphere at room temperature overnight. After completion of the reaction, the solvent was evaporated under reduced pressure from the reaction mixture. The obtained residue was subjected to silica gel column chromatography (eluent: dichloromethane-methanol (20:1), 0.05% pyridine) to give the object substance (2.6 g, yield 76%, two-step).

$^1$H-NMR (CDCl$_3$): δ7.44-7.49 (m, 2H), 7.28-7.38 (m, 6H), 7.20-7.26 (m, 1H), 6.83-6.88 (m, 4H), 3.83 (s, 6H), 3.70 (dd, 1H, J=9.2 Hz, 5.2 Hz), 3.20 (q, 2H, J=6.9 Hz), 3.03 (t, 2H, J=6.6 Hz), 2.97-3.00 (m, 1H), 2.86-2.93 (m, 1H), 2.10-2.21 (m, 1H), 1.58-1.97 (m, 5H), 1.25-1.57 (m, 6H)

[[4] Synthesis of Compound (4a)]

Compound 3a (2.5 g, 4.8 mmol) was dissolved in N,N-dimethylformamide (15 mL). 8-Hydroxyoctanoic acid (0.93 g, 1.2 eq) and 1-ethyl-3-(3-dimethylaminopropyl)carbodiimide hydrochloride (1.1 g, 1.2 eq) and 1-hydroxybenzotriazole (1.8 g, 2.4 eq) were dissolved in N,N-dimethylformamide (15 mL). To this mixture was added the solution of compound 3a in N,N-dimethylformamide at 0° C., and the mixture was stirred under an argon atmosphere at room temperature overnight. After completion of the reaction, the solvent was evaporated under reduced pressure from the reaction mixture. To the obtained residue was added dichloromethane, and the mixture was washed with saturated aqueous sodium bicarbonate and saturated brine. The organic phase was dried over sodium sulfate and the solvent was evaporated. The obtained residue was subjected to silica gel column chromatography (eluent: dichloromethane-methanol (40:1), 0.05% pyridine) to give the object substance (2.1 g, yield 71%).

$^1$H-NMR (CDCl$_3$): δ7.42-7.46 (m, 2H), 7.26-7.36 (m, 6H), 7.16-7.24 (m, 1H), 6.81-6.86 (m, 4H), 3.79 (s, 6H), 3.58-3.66 (m, 2H), 3.49-3.56 (m, 1H), 3.37-3.44 (m, 1H), 3.10-3.27 (m, 1H), 3.01 (2H, t, J=6.6 Hz), 2.29-2.35 (m, 2H), 1.42-1.71 (m, 10H), 1.21-1.41 (m, 12H)

[[5] Synthesis of Compound (5a)]

To a solution (8 mL) of azeotropically dried compound 4a (2.0 g, 2.6 mmol) in acetonitrile was added diisopropylammoniumtetrazolide (DIPAT) (0.64 g, 1.2 eq.). A solution (2 mL) of 2-cyanoethoxy-N,N,N',N'-tetraisopropylphosphordiamidite (1.1 g, 1.2 eq.) in acetonitrile was added and the mixture was stirred at room temperature for 2 hr. Dichloromethane was added, and the mixture was washed with saturated aqueous sodium bicarbonate solution and with saturated brine. The organic phase was dried over sodium sulfate and the solvent was evaporated. The residue was subjected to column chromatography (eluent:n-hexane-ethyl acetate (1:1), 0.1% triethylamine) using amino silica to give the object substance (2.1 g, yield 81%).

$^{31}$P-NMR (CDCl$_3$): 5=147.821

ESI-Mass m/z:877.55 [M+H$_2$O+H]$^+$, 960.66 [M+TEA+H]$^+$

[[6] Synthesis of Compound (1b)]

Fmoc-L-proline (3.0 g, 8.9 mmol) was dissolved in dehydrated N,N-dimethylformamide (60 mL). 8-Amino-1-octanol (1.5 g, 1.2 eq), 1-ethyl-3-(3-dimethylaminopropyl)carbodiimide hydrochloride (2.0 g, 1.2 eq) and 1-hydroxybenzotriazole (3.3 g, 2.4 eq) were added, and the mixture was stirred under an argon atmosphere at room temperature overnight. After completion of the reaction, the solvent was evaporated under reduced pressure from the reaction mixture. To the obtained residue was added dichloromethane, and the mixture was washed with saturated aqueous sodium bicarbonate solution and with saturated brine. The organic phase was dried over sodium sulfate and the solvent was evaporated. The obtained residue was subjected to silica gel column chromatography (eluent: dichloromethane-methanol (20:1)) to give the object substance (3.0 g, yield 73%).

$^1$H-NMR (CDCl$_3$): δ7.76-7.83 (m, 2H), 7.50-7.64 (m, 2H), 7.39-7.45 (m, 2H), 7.30-7.36 (m, 2H), 4.58-4.37 (m, 2H), 4.16-4.37 (m, 2H), 3.57-3.65 (m, 2H), 3.38-3.57 (m, 2H), 3.10-3.30 (m, 2H), 1.82-2.07 (m, 3H), 1.21-1.59 (m, 13H)

[[7] Synthesis of Compound (2b)]

Using dehydrated pyridine, compound 1b (3.0 g, 6.5 mmol) was azeotropically dried. The residue was dissolved in dehydrated pyridine (40 mL). 4,4-Dimethoxytritylchloride (DMTrCl) (2.6 g, 1.2 eq.) was added at 0° C. and the mixture was stirred at room temperature overnight. After confirming the disappearance of the starting materials by TLC, methanol was added and the mixture was stirred for 30 min. The solvent was evaporated under reduced pressure. To the obtained residue was added dichloromethane, and the mixture was washed with saturated aqueous sodium bicarbonate solution and with saturated brine. The organic phase was dried over sodium sulfate and the solvent was evaporated. The residue was dried under reduced pressure to give an oily substance (5.0 g).

[[8] Synthesis of Compound (3b)]

Compound 2b (5.0 g, 6.5 mmol) was dissolved in dehydrated N,N-dimethylformamide (40 mL). Piperidine (6.4 mL) was added, and the mixture was stirred under an argon atmosphere at room temperature overnight. After completion of the reaction, the solvent was evaporated under reduced pressure from the reaction mixture. The obtained residue was subjected to silica gel column chromatography (eluent: dichloromethane-methanol (15:1), 0.05% pyridine) to give the object substance (2.9 g, yield 83%, two-step).

$^1$H-NMR (CDCl$_3$): δ7.43-7.47 (m, 2H), 7.26-7.37 (m, 6H), 7.18-7.23 (m, 1H), 6.81-6.86 (m, 4H), 3.80 (s, 6H), 3.71 (dd, 1H, J=9.2 Hz, 5.2 Hz), 3.21 (q, 2H, J=6.9 Hz), 2.97-3.06 (m, 3H), 2.85-2.91 (m, 1H), 2.09-2.18 (m, 1H), 1.87-1.96 (m, 1H), 1.66-1.74 (m, 2H), 1.57-1.65 (m, 2H), 1.44-1.52 (m, 2H), 1.22-1.38 (m, 8H)

[[9] Synthesis of Compound (4b)]

Compound 3b (2.8 g, 5.1 mmol) was dissolved in dehydrated dichloromethane (40 mL). 10-hydroxydecanoic acid (1.2 g, 1.2 eq), 1-ethyl-3-(3-dimethylaminopropyl)carbodiimide hydrochloride (1.2 g, 1.2 eq), 1-hydroxybenzotriazole (1.9 g, 2.4 eq) and triethylamine (2.6 mL) were added, and the mixture was stirred under an argon atmosphere at room temperature overnight. After completion of the reaction, the solvent was evaporated under reduced pressure from the reaction mixture. To the obtained residue was added dichloromethane, and the mixture was washed with saturated aqueous sodium bicarbonate solution and with saturated brine. The organic phase was dried over sodium sulfate and the solvent was evaporated. The obtained residue was subjected to silica gel column chromatography (eluent: dichloromethane-methanol (20:1), 0.05% pyridine) to give the object substance (2.5 g, yield 70%).

¹H-NMR (CDCl₃): δ7.41-7.45 (m, 2H), 7.25-7.35 (m, 6H), 7.16-7.21 (m, 1H), 6.79-6.85 (m, 4H), 3.79 (s, 6H), 3.58-3.65 (m, 2H), 3.48-3.54 (m, 1H), 3.36-3.43 (m, 1H), 3.11-3.22 (m, 1H), 3.01 (2H, t, J=6.6 Hz), 2.26-2.32 (m, 2H), 1.50-1.68 (m, 8H), 1.39-1.49 (m, 2H) 1.19-1.38 (m, 20H)

[[10] Synthesis of Compound (5b)]

To a solution (8 mL) of azeotropically dried compound 4b (2.4 g, 3.4 mmol) in acetonitrile was added diisopropylammoniumtetrazolide (DIPAT) (0.69 g, 1.2 eq.). A solution (2 mL) of 2-cyanoethoxy-N,N,N',N'-tetraisopropylphosphordiamidite (1.2 g, 1.2 eq.) in acetonitrile was added and the mixture was stirred at room temperature for 2 hr. Dichloromethane was added and the mixture was washed with saturated aqueous sodium bicarbonate solution and with saturated brine. The organic phase was dried over sodium sulfate and the solvent was evaporated. The residue was subjected to column chromatography (eluent: n-hexane-ethyl acetate (1:1), 0.1% triethylamine) using amino silica to give the object substance (2.4 g, yield 80%).

³¹P-NMR (CDCl₃): δ=147.810

ESI-Mass m/z: 937.56 [M+Na]⁺, 1016.70 [M+TEA+H]⁺

[[11] Synthesis of Compound (1c)]

Fmoc-L-proline (3.0 g, 8.9 mmol) was dissolved in a mixed solvent of dehydrated acetonitrile (75 mL) and dehydrated N,N-dimethylformamide (15 mL). 10-Amino-1-decanol (1.8 g, 1.2 eq), N,N'-dicyclohexylcarbodiimide (2.2 g, 1.2 eq) and 1-hydroxybenzotriazole (3.3 g, 2.4 eq) were added, and the mixture was stirred under an argon atmosphere at room temperature overnight. After completion of the reaction, the precipitate was filtered, and the solvent was evaporated under reduced pressure from the filtrate. To the obtained residue was added dichloromethane, and the mixture was washed with saturated aqueous sodium bicarbonate solution and with saturated brine. The organic phase was dried over sodium sulfate and the solvent was evaporated. The residue was triturated with diisopropylether and dried under reduced pressure to give a solid substance (4.0 g, yield 93%).

¹H-NMR (CDCl₃): δ7.72-7.78 (m, 2H), 7.50-7.62 (m, 2H), 7.35-7.42 (m, 2H), 7.26-7.33 (m, 2H), 4.54-4.33 (m, 2H), 4.12-4.33 (m, 2H), 3.57-3.62 (m, 2H), 3.34-3.54 (m, 2H), 3.06-3.26 (m, 2H), 1.80-2.04 (m, 3H), 1.13-1.47 (m, 17H)

[[12] Synthesis of Compound (2c)]

Using dehydrated pyridine, compound 1c (3.9 g, 8.0 mmol) was azeotropically dried. The residue was dissolved in dehydrated pyridine (50 mL). 4,4-Dimethoxytritylchloride (DMTrCl) (3.2 g, 1.2 eq.) was added at 0° C. and the mixture was stirred at room temperature overnight. After confirming the disappearance of the starting materials by TLC, methanol was added and the mixture was stirred for 30 min. The solvent was evaporated under reduced pressure. To the obtained residue was added dichloromethane, and the mixture was washed with saturated aqueous sodium bicarbonate solution and with saturated brine. The organic phase was dried over sodium sulfate and the solvent was evaporated. The residue was dried under reduced pressure to give an oily substance (6.2 g).

[[13] Synthesis of Compound (3c)]

Compound 2c (6.2 g, 7.8 mmol) was dissolved in dehydrated N,N-dimethylformamide (50 mL). Piperidine (7.7 mL) was added, and the mixture was stirred under an argon atmosphere at room temperature overnight. After completion of the reaction, the solvent was evaporated under reduced pressure from the reaction mixture. The obtained residue was subjected to silica gel column chromatography (eluent: dichloromethane-methanol (15:1), 0.05% pyridine) to give the object substance (3.4 g, yield 76%, two-step).

¹H-NMR (CDCl₃): δ7.38-7.42 (m, 2H), 7.21-7.31 (m, 6H), 7.13-7.18 (m, 1H), 6.75-6.80 (m, 4H), 3.79 (s, 6H), 3.72 (dd, 1H, J=9.2 Hz, 5.7 Hz), 3.21 (q, 2H, J=6.9 Hz), 2.98-3.03 (m, 3H), 2.80-2.88 (m, 1H), 2.05-2.15 (m, 1H), 1.83-1.91 (m, 1H), 1.66-1.74 (m, 2H), 1.52-1.59 (m, 2H), 1.38-1.48 (m, 2H), 1.16-1.34 (m, 12H)

[[14] Synthesis of Compound (4c)]

Compound 3c (2.4 g, 4.2 mmol) was dissolved in N,N-dimethylformamide (20 mL). 12-Hydroxydodecanoic acid (1.1 g, 1.2 eq), 1-ethyl-3-(3-dimethylaminopropyl)carbodiimide hydrochloride (0.96 g, 1.2 eq) and 1-hydroxybenzotriazole (1.5 g, 2.4 eq) were dissolved in N,N-dimethylformamide (20 mL). To this mixture was added the solution of compound 3c in N,N-dimethylformamide at 0° C., and the mixture was stirred under an argon atmosphere at room temperature overnight. After completion of the reaction, the solvent was evaporated under reduced pressure from the reaction mixture. To the obtained residue was added dichloromethane, and the mixture was washed with saturated aqueous sodium bicarbonate solution and with saturated brine. The organic phase was dried over sodium sulfate and the solvent was evaporated. The obtained residue was subjected to silica gel column chromatography (eluent: n-hexane-ethyl acetate (1:3), 0.05% pyridine) to give the object substance (2.1 g, yield 66%).

¹H-NMR (CDCl₃): δ7.41-7.45 (m, 2H), 7.25-7.34 (m, 6H), 7.17-7.22 (m, 1H), 6.79-6.83 (m, 4H), 3.79 (s, 6H), 3.58-3.67 (m, 2H), 3.47-3.56 (m, 1H), 3.35-3.44 (m, 1H), 3.09-3.29 (m, 1H), 3.02 (2H, t, J=6.6 Hz), 2.25-2.35 (m, 2H), 1.53-1.65 (m, 9H), 1.18-1.39 (m, 29H)

[[15] Synthesis of Compound (5c)]

To a solution (8 mL) of azeotropically dried compound 4c (2.0 g, 2.6 mmol) in acetonitrile was added diisopropylammoniumtetrazolide (DIPAT) (0.53 g, 1.2 eq.). A solution (2 mL) of 2-cyanoethoxy-N,N,N',N'-tetraisopropylphosphordiamidite (0.94 g, 1.2 eq.) in acetonitrile was added and the mixture was stirred at room temperature for 2 hr. Dichloromethane was added and the mixture was washed with saturated aqueous sodium bicarbonate solution and with saturated brine. The organic phase was dried over sodium sulfate and the solvent was evaporated. The residue was subjected to column chromatography (eluent: n-hexane-ethyl acetate (1:1), 0.1% triethylamine) using amino silica to give the object substance (1.9 g, yield 76%).

³¹P-NMR (CDCl3): δ=147.821

ESI-Mass m/z:989.67 [M+H₂O+H]⁺, 1072.78 [M+TEA+H]⁺

(Example 6) Synthesis of sgRNA

Using compounds 5, 10, 15, 5a, 5b and 5c synthesized in Examples 2-5, proline diamide amidite, lysine diamide amidite, glycine diamide amidite, terephthalic acid diamide amidite and glycylglycine diamide amidite known per se, sgRNAs shown in Table 2-1-Table 4 were synthesized in the same manner as in Example 1. In the following sequences, the underlined part is a guide region complementary to the target nucleotide sequence and the amino acid derivative linkers are shown by abbreviations as shown in Table 5.

TABLE 2-1

```
5'-Xc(n)20-GUUUUAGA--GCUA
            ||||    ||||    Xa
         C-GGAAUAAAAUUGAACGAU
       U |||:
       |  GUCCG--Y--AACUU
       A       ||||     Xb
          AGCCACGUGAA
        G ||||||
          UCGGUGCUXdU-3'
```

| ID | Sequence (5'-3') | number of residue | modification Xa | Xb | Y | Xc-5' | Xd-3' | note |
|---|---|---|---|---|---|---|---|---|
| SG-0001 | GUAGUUGGAGCU*GUU*GGCGUGUUUUAGAGCUAGAAAUAGCAAGUUAAAAUAAGGCUAGUCCGUUAUCAACUUGAAAAAGUGGCACCGAGUCGGUGCUUU | 99 | — | — | — | — | — | natural form |
| SG-0002 | GUAGUUGGAGCU*GUU*GGCGUGUUUUAGAGCUA-P-UAGCAAGUUAAAAUAAGGCUAGUCCGUUAUCAACUUGAAAAAGUGGCACCGAGUCGGUGCUUU | 96 | P | — | — | — | — | P: introduced into one position |
| SG-0012 | GUAGUUGGAGCU*GUU*GGCGUGUUUUAGAGCUA-K-UAGCAAGUUAAAAUAAGGCUAGUCCGUUAUCAACUUGAAAAAGUGGCACCGAGUCGGUGCUUU | 96 | K | — | — | — | — | K: introduced into one position |
| SG-0013 | GUAGUUGGAGCU*GUU*GGCGUGUUUUAGAGCUA-X-UAGCAAGUUAAAAUAAGGCUAGUCCGUUAUCAACUUGAAAAAGUGGCACCGAGUCGGUGCUUU | 96 | GlyGly | — | — | — | — | GlyGly: introduced into one position |
| SG-0014 | GUAGUUGGAGCU*GUU*GGCGUGUUUUAGAGCUA-P-UAGCAAGUUAAAAUAAGGCUAGUCCGUUAUCAACUU-P-AAGUGGCACCGAGUCGGUGCUUU | 93 | P | P | — | — | — | P: introduced into two positions |
| SG-0015 | GUAGUUGGAGCU*GUU*GGCGUGUUUUAGAGCUA-P-UAGCAAGUUAAAAUAAGGCUAGUCCG-X-AACUU-P-AAGUGGCACCGAGUCGGUGCUUU | 89 | P | P | GlyGly | — | — | P: introduced into two positions, GlyGly: introduced into one position |
| SG-0016 | P-GUAGUUGGAGCU*GUU*GGCGUGUUUUAGAGCUA-P-UAGCAAGUUAAAAUAAGGCUAGUCCGUUAUCAACUUGAAAAAGUGGCACCGAGUCGGUGCU-P-U | 97 | P | — | — | P | P | P: introduced into three position |
| SG-0024 | GUAGUUGGAGCU*GUU*GGCGUGUUUUAGAGCUA-P13-UAGCAAGUUAAAAUAAGGCUAGUCCGUUAUCAACUUGAAAAAGUGGCACCGAGUCGGUGCUUU | 96 | P13 | — | — | — | — | P13: introduced into one position |
| SG-0025 | GUAGUUGGAGCU*GUU*GGCGUGUUUUAGAGCUA-P14-UAGCAAGUUAAAAUAAGGCUAGUCCGUUAUCAACUUGAAAAAGUGGCACCGAGUCGGUGCUUU | 96 | P14 | — | — | — | — | P14: introduced into one position |
| SG-0026 | GUAGUUGGAGCU*GUU*GGCGUGUUUUAGAGCUA-P15-UAGCAAGUUAAAAUAAGGCUAGUCCGUUAUCAACUUGAAAAAGUGGCACCGAGUCGGUGCUUU | 96 | P15 | — | — | — | — | P15: introduced into one position |
| SG-0027 | GUAGUUGGAGCU*GUU*GGCGUGUUUUAGAGCUA-X10-UAGCAAGUUAAAAUAAGGCUAGUCCGUUAUCAACUUGAAAAAGUGGCACCGAGUCGGUGCUUU | 96 | F | — | — | — | — | X10(F): introduced into one position |
| SG-0028 | GUAGUUGGAGCU*GUU*GGCGUGUUUUAGAGCUA-X11-UAGCAAGUUAAAAUAAGGCUAGUCCGUUAUCAACUUGAAAAAGUGGCACCGAGUCGGUGCUUU | 96 | L | — | — | — | — | X11(L): introduced into one position |
| SG-0029 | GUAGUUGGAGCU*GUU*GGCGUGUUUUAGAGCUA-X12-UAGCAAGUUAAAAUAAGGCUAGUCCGUUAUCAACUUGAAAAAGUGGCACCGAGUCGGUGCUUU | 96 | E | — | — | — | — | X12(E): introduced into one position |

TABLE 2-1-continued

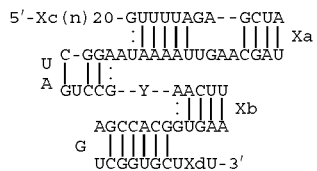

| ID | Sequence (5'-3') | number of residue | Xa | Xb | Y | Xc-5' | Xd-3' | note |
|---|---|---|---|---|---|---|---|---|
| SG-0030 | GUAGUUGGAGCUG*UU*GGCGUGUUUUAGAGCUA-P-UAGCAAGUUAAAAUAAGGCUAGUCCG-P-AACUU-P-AAGUGGCACCGAGUCGGUGCUUU | 89 | P | P | P | — | — | P: introduced into three positions |
| SG-0031 | GUAGUUGGAGCUG*UU*GGCGUGUUUUAGAGCUA-P-UAGCAAGUUAAAAUAAGGCUAGUCCG-P13-AACUU-P-AAGUGGCACCGAGUCGGUGCUUU | 89 | P | P | P13 | — | — | P: introduced into two positions, P13: introduced into one position |
| SG-0032 | GUAGUUGGAGCUG*UU*GGCGUGUUUUAGAGCUA-GP-UAGCAAGUUAAAAUAAGGCUAGUCCG-P14-AACUU-P-AAGUGGCACCGAGUCGGUGCUUU | 89 | P | P | P14 | — | — | P: introduced into two positions, P14: introduced into one position |
| SG-0033 | GUAGUUGGAGCUG*UU*GGCGUGUUUUAGAGCUA-P-UAGCAAGUUAAAAUAAGGCUAGUCCG-P15-AACUU-P-AAGUGGCACCGAGUCGGUGCUUU | 89 | P | P | P15 | — | — | P: introduced into two positions, P15: introduced into one position |
| SG-0034 | GUAGUUGGAGCUG*UU*GGCGUGUUUUAGAGCUA-P-UAGCAAGUUAAAAUAAGGCUAGUCCG-X10-AACUU-P-AAGUGGCACCGAGUCGGUGCUUU | 89 | P | P | F | — | — | P: introduced into two positions, X10(F): introduced into one position |

TABLE 2-2

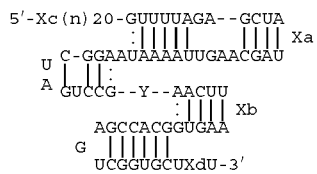

| ID | Sequence (5'-3') | number of residue | Xa | Xb | Y | Xc-5' | Xd-3' | note |
|---|---|---|---|---|---|---|---|---|
| SG-0035 | GUAGUUGGAGCUG*UU*GGCGUGUUUUAGAGCUA-P-UAGCAAGUUAAAAUAAGGCUAGUCCG-X11-AACUU-P-AAGUGGCACCGAGUCGGUGCUUU | 89 | P | P | L | — | — | P: introduced into two positions, X11(L): introduced into one position |
| SG-0036 | GUAGUUGGAGCUG*UU*GGCGUGUUUUAGAGCU A-P-UAGCAAGUUAAAAUAAGGCUAGUCCG-X12-AACUU-P-AAGUGGCACCGAGUCGGUGCUUU | 89 | P | P | E | — | — | P: introduced into two positions, X12(E): introduced into one position |

TABLE 2-2-continued

```
5'-Xc(n)20-GUUUUAGA--GCUA
         :||||    ||||  Xa
       C-GGAAUAAAAUUGAACGAU
     U |  |||                :
     |    ||| 
     A GUCCG--Y--AACUU
            :||||    Xb
          AGCCACGGUGAA
        G  ||||||
        UCGGUGCUXdU-3'
```

| ID | Sequence (5'-3') | number of residue | modification Xa | Xb | Y | Xc-5' | Xd-3' | note |
|---|---|---|---|---|---|---|---|---|
| SG-0050 | GUAGUUGGAGCU*GU*UGGCGUGUUUUAGAGCUA-X8-UAGCAAGUUAAAAUAAGGCUAGUCCGUUAUCAACUUGAAAAAGUGGCACCGAGUCGGUGCUUU | 96 | Gly | — | — | — | — | X8(Gly): introduced into one position |
| SG-0051 | GUAGUUGGAGCU*GU*UGGCGUGUUUUAGAGCUA-X7-UAGCAAGUUAAAAUAAGGCUAGUCCGUUAUCAACUUGAAAAAGUGGCACCGAGUCGGUGCUUU | 96 | TP | — | — | — | — | X7(TP): introduced into one position |
| SG-0052 | GUAGUUGGAGU*GU*UGGCGUGUUUUAGAGCUA-P-UAGCAAGUUAAAAUAAGGCUAGUCCG-X8-AACUU-P-AAGUGGCACCGAGUCGGUGCUUU | 89 | P | P | Gly | — | — | P: introduced into two positions, X8(Gly): introduced into one position |
| SG-0053 | GUAGUUGGAGCU*GU*UGGCGUGUUUUAGAGCUA-P-UAGCAAGUUAAAAUAAGGUAGUCCG-X7-AACUU-P-AAGUGGCACCGAGUCGGGUGCUUU | 89 | P | P | TP | — | — | P: introduced into two positions, X7(TP): introduced into one position |
| SG-0075 | GUAGUUGGAGCU*GU*UGGCGUGUUUUAGAGCUA-K-UAGCAAGUUAAAAUAAGGCUAGUCCGUUAUCAACUU-K-AAGUGGCACCGAGUCGGUGCUUU | 93 | K | K | — | — | — | K introduced into two positions |
| SG-0076 | GUAGUUGGAGCU*GU*UGGCGUGUUUUAGAGCUA-X-UAGCAAGUUAAAAUAAGGCUAGUCCGUUAUCAACUU-X-AAGUGGCACCGAGUCGGUGCUUU | 93 | GlyGly | GlyGly | — | — | — | X: GlyGly introduced into two positions |
| SG-0077 | GUAGUUGGAGCU*GU*UGGCGUGUUUUAGAGCUA-X-UAGCAAGUUAAAAUAAGGCUAGUCCGUUAUCAACUU-X-AAGUGGCACCGAGUCGGUGCUUU | 93 | Gly | Gly | — | — | — | X: Gly introduced into two positions |
| SG-0078 | GUAGUUGGAGCU*GU*UGGCGUGUUUUAGAGCUA-X7-UAGCAAGUUAAAAUAAGGCUAGUCCGUUAUCAACUU-X7-AAGUGGCACCGAGUCGGUGCUUU | 93 | TP | TP | — | — | — | X7: TP introduced into two positions |
| SG-0079 | GUAGUUGGAGCU*GU*UGGCGUGUUUUAGAGCUA-X10-UAGCAAGUUAAAAUAAGGCUAGUCCGUUAUCAACUU-X10-AAGUGGCACCGAGUCGGUGCUUU | 93 | F | F | — | — | — | X10: F introduced into two positions |
| SG-0080 | GUAGUUGGAGCU*GU*UGGCGUGUUUUAGAGCUA-X11-UAGCAAGUUAAAAUAAGGCUAGUCCGUUAUCAACUU-X11-AAGUGGCACCGAGUCGGUGCUUU | 93 | L | L | — | — | — | X11: L introduced into two positions |
| SG-0081 | GUAGUUGGAGCU*GU*UGGCGUGUUUUAGAGCUA-X12-UAGCAAGUUAAAAUAAGGCUAGUCCGUUAUCAACUU-X12-AAGUGGCACCGAGUCGGUGCUUU | 93 | E | E | — | — | — | X12: E introduced into two positions |
| SG-0082 | GUAGUUGGAGCU*GU*UGGCGUGUUUUAGAGCUA-P-UAGCAAGUUAAAAUAAGGCUAGUCCG-K-AACUU-P-AAGUGGCACCGAGUCGGUGCUUU | 89 | P | P | K | — | — | P: introduced into two positions, K: introduced into one position |

TABLE 2-2-continued

```
5'-Xc(n)20-GUUUUAGA--GCUA
        :||||| ||||   Xa
      U C-GGAAUAAAAUUGAACGAU
      |||  :
      A GUCCG--Y--AACUU
        :||||    Xb
        AGCCACGGUGAA
      G ||||||
        UCGGUGCUXdU-3'
```

| ID | Sequence (5'-3') | number of residue | modification Xa | Xb | Y | Xc-5' | Xd-3' | note |
|---|---|---|---|---|---|---|---|---|
| SG-0083 | K-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-K-U | 97 | P | — | — | K | K | P: Xa, K: both terminals |
| SG-0084 | X-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X-U | 97 | P | — | — | GlyGly | GlyGly | P: Xa, X = GlyGly: both terminals |
| SG-0085 | X-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X-U | 97 | P | — | — | Gly | Gly | P: Xa, X = Gly: both terminals |
| SG-0086 | X7-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X7-U | 97 | P | — | — | TP | TP | P: Xa, X7 = TP: both |

TABLE 2-3

```
5'-Xc(n)20-GUUUUAGA--GCUA
        :||||| ||||   Xa
      U C-GGAAUAAAAUUGAACGAU
      |||  :
      A GUCCG--Y--AACUU
        :||||    Xb
        AGCCACGGUGAA
      G ||||||
        UCGGUGCUXdU-3'
```

| ID | Sequence (5'-3') | number of residue | modification Xa | Xb | Y | Xc-5' | Xd-3' | note |
|---|---|---|---|---|---|---|---|---|
| SG-0087 | X10-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X10-U | 97 | P | — | — | F | F | P: Xa, X10 = F: both terminals |
| SG-0088 | X11-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X11-U | 97 | P | — | — | L | L | P: Xa, X11 = L: both terminals |
| SG-0089 | X12-<u>GUAGUUGGAGCU</u>*GU*<u>U</u>GGCGUGUUUUAGAGCUA-P-UAGCAAGUUAAAAUAAGGCUAGUCCGUUAUCAACUUGAAAAAGUGGCACCGAGUCGGUGCU-X12-U | 97 | P | — | — | E | E | P: Xa, X12 = E: both |
| SG-0004 | <u>GUAGUUGGAGCU</u>*GU*<u>U</u>GGCGUGUUUUAGAGCUAGAAAUAGCAAGUUAAAAUAAGGCUAGUCCG | 62 | — | del | del | — | del | 3' terminal shortened |
| SG-0054 | <u>GUAGUUGGAGCU</u>*GU*<u>U</u>GGCGUGUUUUAGAGCUAGAAAUAGCAAGUUAAAAUAAGGCUAGUCCGUUAUCAACUUGAAAAAGU | 80 | — | — | — | — | del | 3' terminal shortened |
| SG-0055 | <u>GUAGUUGGAGCU</u>*GU*<u>U</u>GGCGUGUUUUAGAGCUAGAAAUAGCAAGUUAAAAUAAGGC | 55 | — | del | del | — | del | 3' terminal shortened |
| SG-0056 | <u>GUAGUUGGAGCU</u>*GU*<u>U</u>GGCGUGUUUUAGAGCUAGAAAUAGCAAGUUAAAAU | 50 | — | del | del | — | del | 3' terminal shortened |
| SG-0057 | <u>GUAGUUGGAGCU</u>*GU*<u>U</u>GGCGUGUUUUAGAGCUAGAAAUAGCAAGUU | 45 | — | del | del | — | del | 3' terminal shortened |

TABLE 2-3-continued

```
5'-Xc(n)20-GUUUUAGA--GCUA
           :|||||    ||||  Xa
         C-GGAAUAAAAUUGAACGAU
       U   |||   :
       A GUCCG--Y--AACUU
           :||||       ||||  Xb
              AGCCACGGUGAA
            G |||||||
              UCGGUGCUXdU-3'
```

| ID | Sequence (5'-3') | number of residue | Xa | Xb | Y | Xc-5' | Xd-3' | note |
|---|---|---|---|---|---|---|---|---|
| SG-0058 | GUAGUUGGAGCU*GUU*GGCGUGUUUUAGAGCUAGAAAUAGC AAGUUAAAAUAAGGC-P-GUCCGUUAUCAACUUGAAAAAG UGGCACCGAGUCGGUGCUUU | 98 | — | — | — | — | — | loop 1: P |
| SG-0059 | GUAGUUGGAGCU*GUU*GGCGUGUUUUAGAGCUAGAAAUAGC AAGUUAAAAUAAGGCUAGUCCGUUAUCAACUUGAAAAAGU GGCACCG-P-CGGUGCUUU | 97 | — | — | — | — | — | loop 3: P |
| SG-0060 | GUAGUUGGAGCU*GU*UGGCGUGUUUUAGAG-P-CAAGUUAA AAUAAGGCUAGUCCGUUAUCAACUUGAAAAAGUGGCACCG AGUCGGUGCUUU | 90 | P | — | — | — | — | Xa + stem: P |
| SG-0061 | GUAGUUGGAGCU*GUU*GGCGUGUUUUAGAGCUAGAAAUAGC AAGUUAAAAUAAGGCUAGUCCGUUAUCA-P-GGCACCGAG UCGGUGCUUU | 88 | — | P | — | — | — | Xb + stem: P |
| SG-0062 | GUAGUUGGAGCU*GUU*GGCGUGUUUUAGAG-P-CAAGUUAA AAUAAGGCUAGUCCG-P-A-P-GGCACCGAGUCGGUGCUUU | 75 | P | P | P | — | — | Xa + stem: P, Xb + stem: P, Y: P |

In Tables, del means that the sequence is deleted

TABLE 3-1

```
5'-Xc(n)20-GUUUUAGA--GCUA
           :|||||    ||||  Xa
         C-GGAAUAAAAUUGAACGAU
       U   |||   :
       A GUCCG--Y--AACUU
           :||||       ||||  Xb
              AGCCACGGUGAA
            G |||||||
              UCGGUGCUXdU-3'
```

| ID | Sequence (5'-3') | number of residue | Xa | Xb | Y | Xc-5' | Xd-3' | note |
|---|---|---|---|---|---|---|---|---|
| SG-0017 | AAGCGUCCCCGCGCGGUGAAGUUUUAGAGCUAGAAAU AGCAAGUUAAAAUAAGGCUAGUCCGUUAUCAACUUGA AAAGUGGCACCGAGUCGGUGCUUU | 99 | — | — | — | — | — | natural form |
| SG-0018 | AAGCGUCCCCGCGCGGUGAAGUUUUAGAGCUA-P-UA GCAAGUUAAAAUAAGGCUAGUCCGUUAUCAACUUGAA AAAGUGGCACCGAGUCGGUGCUUU | 96 | P | — | — | — | — | P: introduced into one position |
| SG-0019 | AAGCGUCCCCGCGCGGUGAAGUUUUAGAGCUA-K-UA GCAAGUUAAAAUAAGGCUAGUCCGUUAUCAACUUGAA AAAGUGGCACCGAGUCGGUGCUUU | 96 | K | — | — | — | — | K: introduced into one position |
| SG-0020 | AAGCGUCCCCGCGCGGUGAAGUUUUAGAGCUA-X- UAGCAAGUUAAAAUAAGGCUAGUCCGUUAUCAACU UGAAAAAGUGGCACCGAGUCGGUGCUUU | 96 | GlyGly | — | — | — | — | GlyGly: introduced into one position |
| SG-0021 | AAGCGUCCCCGCGCGGUGAAGUUUUAGAGCUA-P- UAGCAAGUUAAAAUAAGGCUAGUCCGUUAUCAACU U-P-AAGUGGCACCGAGUCGGUGCUUU | 93 | P | P | — | — | — | P: introduced into two positions |
| SG-0022 | AAGCGUCCCCGCGCGGUGAAGUUUUAGAGCUA-P- UAGCAAGUUAAAAUAAGGCUAGUCCG-X-AACUU- P-AAGUGGCACCGAGUCGGUGCUUU | 89 | P | P | GlyGly | — | — | P: introduced into two positions, GlyGly: introduced into one position |

TABLE 3-1-continued

```
5'-Xc(n)20-GUUUUAGA--GCUA
          :|||||  ||||    Xa
        C-GGAAUAAAAUUGAACGAU
      U |||
      A GUCCG--Y--AACUU
        :||||           Xb
        AGCCACGGUGAA
      G |||||
        UCGGUGCUXdU-3'
```

| ID | Sequence (5'-3') | number of residue | modification Xa | Xb | Y | Xc-5' | Xd-3' | note |
|---|---|---|---|---|---|---|---|---|
| SG-0023 | P-<u>AAGCGUCCCCGCGCGGUGAA</u>GUUUUAGAGCUA-P-UAGCAAGUUAAAAUAAGGCUAGUCCGUUAUCAACUUGAAAAAGUGGCACCGAGUCGGUGGCU-P-U | 97 | P | — | — | P | P | P: introduced into three positiions |
| SG-0037 | <u>AAGCGUCCCCGCGCGGUGAA</u>GUUUUAGAGCUA-P13-UAGCAAGUUAAAAUAAGGCUAGUCCGUUAUCAACUUGAAAAAGUGGCACCGAGUCGGUGCUUU | 96 | P13 | — | — | — | — | P13: introduced into one position |
| SG-0038 | <u>AAGCGUCCCCGCGCGGUGAA</u>GUUUUAGAGCUA-P14-UAGCAAGUUAAAAUAAGGCUAGUCCGUUAUCAACUUGAAAAAGUGGCACCGAGUCGGUGCUUU | 96 | P14 | — | — | — | — | P14: introduced into one position |
| SG-0039 | <u>AAGCGUCCCCGCGCGGUGAA</u>GUUUUAGAGCUA-P15-UAGCAAGUUAAAAUAAGGCUAGUCCGUUAUCAACUUGAAAAAGUGGCACCGAGUCGGUGCUUU | 96 | P15 | — | — | — | — | P15: introduced into one position |
| SG-0040 | <u>AAGCGUCCCCGCGCGGUGAA</u>GUUUUAGAGCUA-X10-UAGCAAGUUAAAAUAAGGCUAGUCCGUUAUCAACUUGAAAAAGUGGCACCGAGUCGGUGCUUU | 96 | F | — | — | — | — | X10(F): introduced into one position |
| SG-0041 | <u>AAGCGUCCCCGCGCGGUGAA</u>GUUUUAGAGCUA-X11-UAGCAAGUUAAAAUAAGGCUAGUCCGUUAUCAACUUGAAAAAGUGGCACCGAGUCGGUGCUUU | 96 | L | — | — | — | — | X11(L): introduced into one position |
| SG-0042 | <u>AAGCGUCCCCGCGCGGUGAA</u>GUUUUAGAGCUA-X12-UAGCAAGUUAAAAUAAGGCUAGUCCGUUAUCAACUUGAAAAAGUGGCACCGAGUCGGUGCUUU | 96 | E | — | — | — | — | X12(E): introduced into one position |
| SG-0043 | <u>AAGCGUCCCCGCGCGGUGAA</u>GUUUUAGAGCUA-P-UAGCAAGUUAAAAUAAGGCUAGUCCG-P-AACUU-P-AAGUGGACCGAGUCGGUGCUUU | 89 | P | P | P | — | — | P: introduced into three positions |
| SG-0044 | <u>AAGCGUCCCCGCGCGGUGAA</u>GUUUUAGAGCUA-P-UAGCAAGUUAAAAUAAGGCUAGUCCG-P13-AACUU-P-AAGUGGCACCGAGUCGGUGCUUU | 89 | P | P | P13 | — | — | P: introduced into two positions, P13: introduced into one position |
| SG-0045 | <u>AAGCGUCCCCGCGCGGUGAA</u>GUUUUAGAGCUA-P-UAGCAAGUUAAAAUAAGGCUAGUCCG-P14-AACUU-P-AAGUGGCACCGAGUCGGUGCUUU | 89 | P | P | P14 | — | — | P: introduced into two positions, P14: introduced into one position |
| SG-0046 | <u>AAGCGUCCCCGCGCGGUGAA</u>GUUUUAGAGCUA-P-UAGCAAGUUAAAAUAAGGCUAGUCCG-P15-AACUU-P-AAGUGGCACCGAGUCGGUGCUUU | 89 | P | P | P15 | — | — | P: introduced into two positions, P15: introduced into one position |
| SG-0047 | <u>AAGCGUCCCCGCGCGGUGAA</u>GUUUUAGAGCUA-P-UAGCAAGUUAAAAUAAGGCUAGUCG-X10-AACUU-P-AAGUGGCACCGAGUCGGUGCUUU | 89 | P | P | F | — | — | P: introduced into two positions, X10(F): introduced into one position |

TABLE 3-2

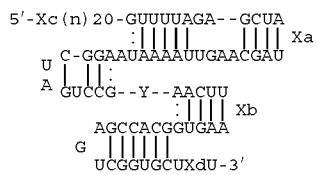

| ID | Sequence (5'-3') | number of residue | modification Xa | Xb | Y | Xc-5' | Xd-3' | note |
|---|---|---|---|---|---|---|---|---|
| SG-0048 | AAGCGUCCCCGCGCGGUGAAGUUUUAGAGCUA-P-UAGCAAGUUAAAAUAAGGCUAGUCCG-X11-AACUU-P-AAGUGGCACCGAGUCGGUGCUUU | 89 | P | P | L | — | — | P: introduced into two positions, X11(L): introduced into one position |
| SG-0049 | AAGCGUCCCCGCGCGGUGAAGUUUUAGAGCUA-P-UAGCAAGUUAAAAUAAGGCUAGUCCG-X12-AACUU-P-AAGUGGCACCGAGUCGGUGCUUU | 89 | P | P | E | — | — | P: introduced into two positions, X12(E): introduced into one position |
| SG-0063 | AAGCGUCCCCGCGCGGUGAAGUUUUAGAGCUA-K-UAGCAAGUUAAAAUAAGGCUAGUCCGUAUCAACUU-K-AAGUGGCACCGAGUCGGUGCUUU | 93 | K | K | — | — | — | K: introduced into two positions |
| SG-0064 | K-AAGCGUCCCCGCGCGGUGAAGUUUUAGAGCUA-P-UAGCAAGUUAAAAUAAGGCUAGUCCGUUAUCAACUUGAAAAAGUGGCACCGAGUCGGUGCU-K-U | 97 | P | — | — | K | K | P: Xa, K: both terminals |

TABLE 4

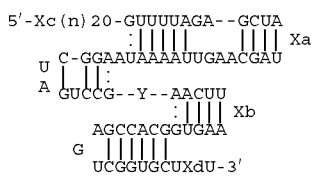

| ID | Sequence (5'-3') | number of residue | modification Xa | Xb | Y | Xc-5' | Xd-3' | note |
|---|---|---|---|---|---|---|---|---|
| SG-0090 | UAGCUACAGAGAAAUCUCGAGUUUUAGAGCUAGAAAUAGCAAGUUAAAAUAAGGCUAGUCCGUUAUCAACUUGAAAAAGUGGCACCGAGUCGGUGCUU | 99 | — | — | — | — | — | natural form |
| SG-0093 | UAGCUACAGAGAAAUCUCGAGUUUUAGAGCUA-P-UAGCAAGUUAAAAUAAGGCUAGUCCGUUAUCAACUU-P-AAGUGGCACCGAGUCGGUGCUUU | 93 | P | P | — | — | — | P: introduced into two positions |
| SG-0096 | UAGCUACAGAGAAAUCUCGAGUUUUAGAGCUA-P-UAGCAAGUUAAAAUAAGGCUAGUCCGUUAUCAACUUGAAAAAGUGGCACCGAGUCGGUGCUUU | 96 | P | — | — | — | — | P: introduced into one position |
| SG-0097 | UAGCUACAGAGAAAUCUCGAGUUUUAGAGCUA-K-UAGCAAGUUAAAAUAAGGCUAGUCCGUUAUCAACUUGAAAAAGUGGCACCGAGUCGGUGCUUU | 96 | K | — | — | — | — | K: introduced into one position |
| SG-0098 | UAGCUACAGAGAAAUCUCGAGUUUUAGAGCUA-P-UAGCAAGUUAAAAUAAGGCUAGUCCG-P-AACUU-P-AAGUGGCACCGAGUCGGUGCUUU | 89 | P | P | P | — | — | P: introduced into three positions |

TABLE 4-continued

```
5'-Xc(n)20-GUUUUAGA--GCUA
            :|||||    ||||  Xa
         C-GGAAUAAAAUUGAACGAU
        U |  |||
        A GUCCG--Y--AACUU
                :||||  Xb
             AGCCACGGUGAA
           G ||||||
             UCGGUGCUXdU-3'
```

| ID | Sequence (5'-3') | number of residue | Xa | Xb | Y | Xc-5' | Xd-3' | note |
|---|---|---|---|---|---|---|---|---|
| SG-0099 | UAGCUACAGAGAAAUCUCGAGUUUUAGAGCUA-P-UA GCAAGUUAAAAUAAGGCUAGUCCG-X-AACUU-P-AA GUGGCACCGAGUCGGUGCUUU | 89 | P | P | GlyGly | — | — | P: introduced into two positions, X = GlyGly: introduced into one position |
| SG-0100 | UAGCUACAGAGAAAUCUCGAGUUUUAGAGCUA-K-UA GCAAGUUAAAAUAAGGCUAGUCCGUUAUCAACUU-K- AAGUGGCACCGAGUCGGUGCUUU | 93 | K | K | — | — | — | K: introduced into two positions |
| SG-0101 | P-UAGCUACAGAGAAAUCUCGAGUUUUAGAGCUA-P- UAGCAAGUUAAAAUAAGGCUAGUCCGUUAUCAACUUG AAAAAGUGGCACCGAGUCGGUGCU-P-U | 97 | P | — | — | P | P | P: Xa, both terminals |
| SG-0102 | K-UAGCUACAGAGAAAUCUCGAGUUUUAGAGCUA-P- UAGCAAGUUAAAAUAAGGCUAGUCCGUUAUCAACUUG AAAAAGUGGCACCGAGUCGGUGCU-K-U | 97 | P | — | — | K | K | P: Xa, K: both terminals |

TABLE 5

| | amino acid amidite | | | |
|---|---|---|---|---|
| abbr. | amino acid | general formula | n | m | Example compound |
| X | glycylglycine (GlyGly) | I-4 | 5 | 4 | |
| X7 | terephthalic acid (TP) | I-6 | 4 | 4 | |
| X8 | glycine (Gly) | I-1 | 5 | 4 | |
| X10 | phenylalanine (P) | IV-1 | 5 | 4 | compound 5 |
| X11 | leucine (L) | IV-2 | 5 | 4 | compound 10 |
| X12 | glutamic acid ('E) | IV-3 | 5 | 4 | compound 15 |
| P | proline (P) | II-8 | 5 | 4 | |
| P13 | proline (P) | II-8 | 7 | 6 | compound 5a |
| P14 | proline (P) | II-8 | 9 | 8 | compound 5b |
| P15 | proline (P) | II-8 | 11 | 10 | compound 5c |
| K | lysin (K) | I-7 | 5 | 4 | |

(Experimental Example 3) Evaluation of In Vitro Cleavage Activity of sgRNA Targeting KRAS Gene-2

Plasmid DNA (pCMV6-Entry-KRAS (G12V), OriGene Technologies) incorporating a sequence (NCBI Refference Sequence NP_0049762) having a G12V mutation in human KRAS gene (GenBank accession No. NM_004985.3) was reacted with restriction enzyme Tth111I (TaKaRa) according to the attached protocol. After completion of the reaction, the DNA of interest was purified according to a conventional method and dissolved in TE buffer (10 mM Tris-HCl, pH 8, 1 mM EDTA) to a final concentration of 100 ng/μL to give a substrate DNA.

The above-mentioned substrate DNA was mixed with sgRNA and Cas9 as follows using the reagent attached to Cas9 Nuclease, S. pyogenes (New England Biolabs);
100 ng substrate DNA+0.5 ng sgRNA+0.3 pmol Cas9 (total amount 10 μL)

This was incubated at 37° C. for 15 min, and further incubated at 70° C. for 10 min to inactivate Cas9. Thereafter, electrophoresis was performed and, after ethidium bromide staining, the band intensity was measured using gel imaging system PXi4 (SYNGENE).

Based on the measurement results, the cleavage efficiency was calculated by the following equation.

Cleavage Efficiency=sum of cleaved band intensities/ (sum of the cleaved and uncleaved band intensities)

Figure 7:
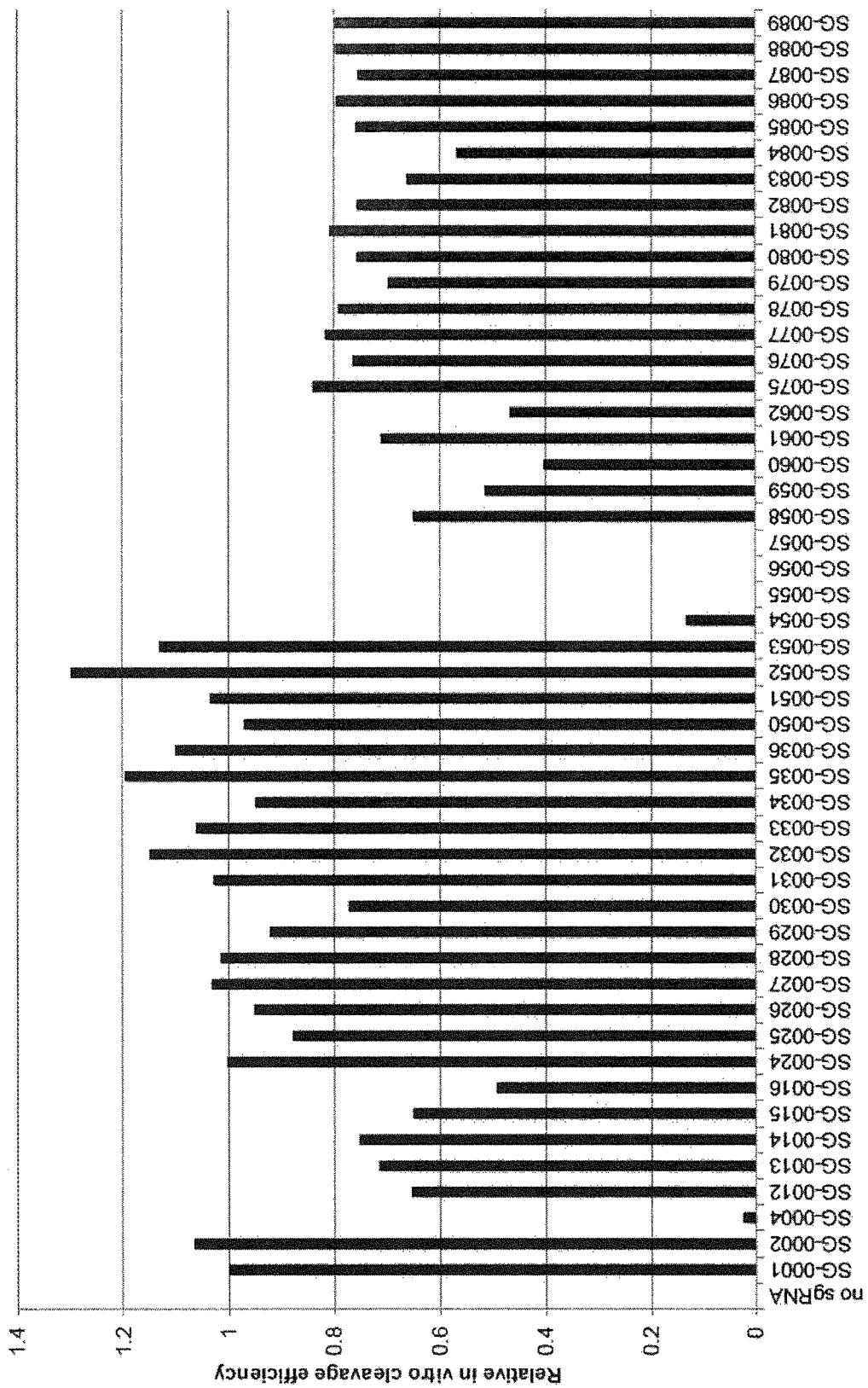
FIG. 7 shows comparison of the in vitro cleavage activity between artificial sgRNA targeting KRAS gene and natural form sgRNA.

The results are shown in FIGS. 3-6. The numerical value under the gel shows cleavage efficiency determined by the above-mentioned calculation formula. Furthermore, the relative cleavage efficiency of the artificial sgRNA of this Example relative to the cleavage efficiency of natural form sgRNA (SG-0001) in Reference Example as 1 is shown in FIG. 7.

Many of the artificial sgRNAs of this Example showed cleavage efficiency equal to or higher than that of the natural form sgRNA in Reference Example, and it was clarified that substitution of each site with an amino acid derivative is effective.

(Experimental Example 4)) Evaluation of In Vitro Cleavage Activity of sgRNA Targeting BCL-2 Gene-2

Plasmid DNA (pCAGGSHB2) incorporating human BCL-2 gene (GenBank accession No. NM_000633) was reacted with restriction enzyme HindIII (TaKaRa) according to the attached protocol. After completion of the reaction, the DNA of interest was purified according to a conventional method and dissolved in TE buffer (10 mM Tris-HCl, pH 8, 1 mM EDTA) to a final concentration of 100 ng/μL to give a substrate DNA.

The above-mentioned substrate DNA was mixed with sgRNA and Cas9 as follows using the reagent attached to Cas9 Nuclease, *S. pyogenes* (New England Biolabs);

100 ng substrate DNA+10 ng sgRNA+0.3 pmol Cas9 (total amount 10 μL)

This was incubated at 37° C. for 30 min, and further incubated at 70° C. for 10 min to inactivate Cas9. Thereafter, electrophoresis was performed and, after ethidium bromide staining, the band intensity was measured using gel imaging system PXi4 (SYNGENE).

Based on the measurement results, the cleavage efficiency was calculated by the following equation.

Cleavage Efficiency=sum of cleaved band intensities/
(sum of the cleaved and uncleaved band intensities)

Figure 8:
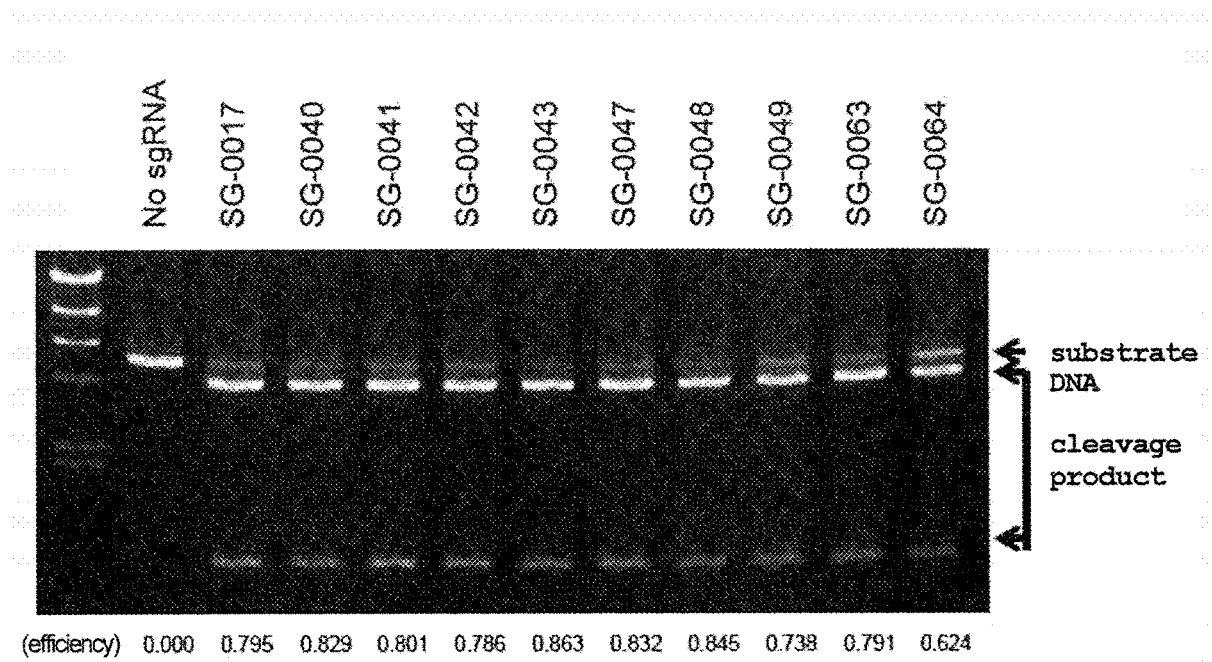
FIG. 8 shows the in vitro cleavage activity of sgRNA targeting BCL-2 gene.
Figure 8:
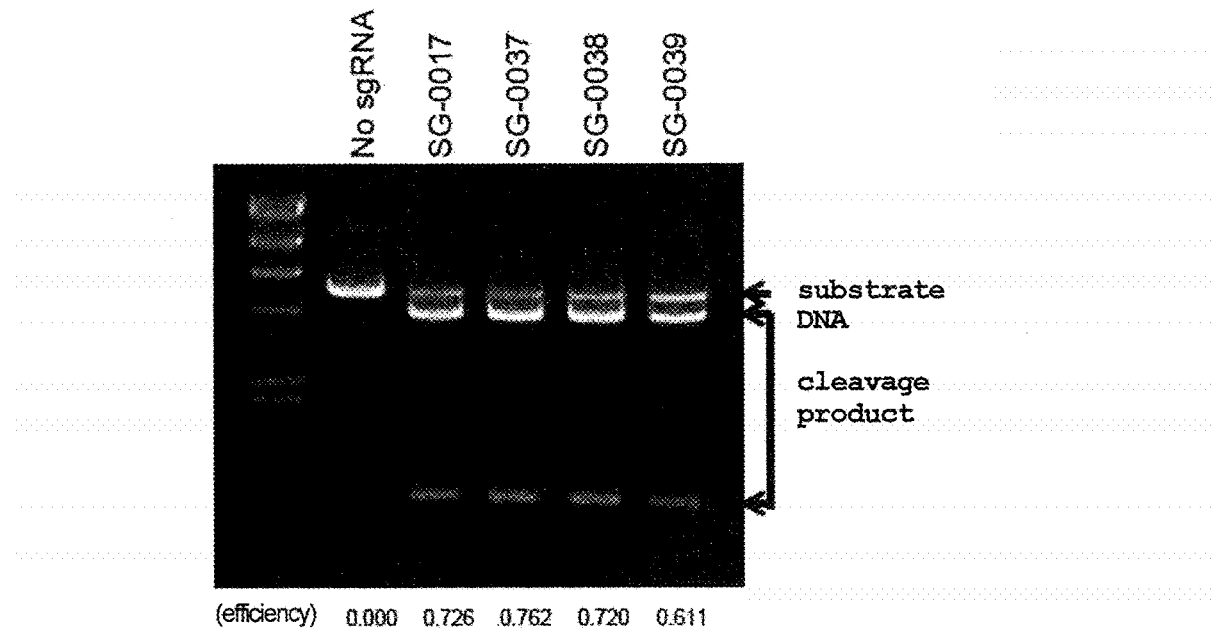
Figure 9:
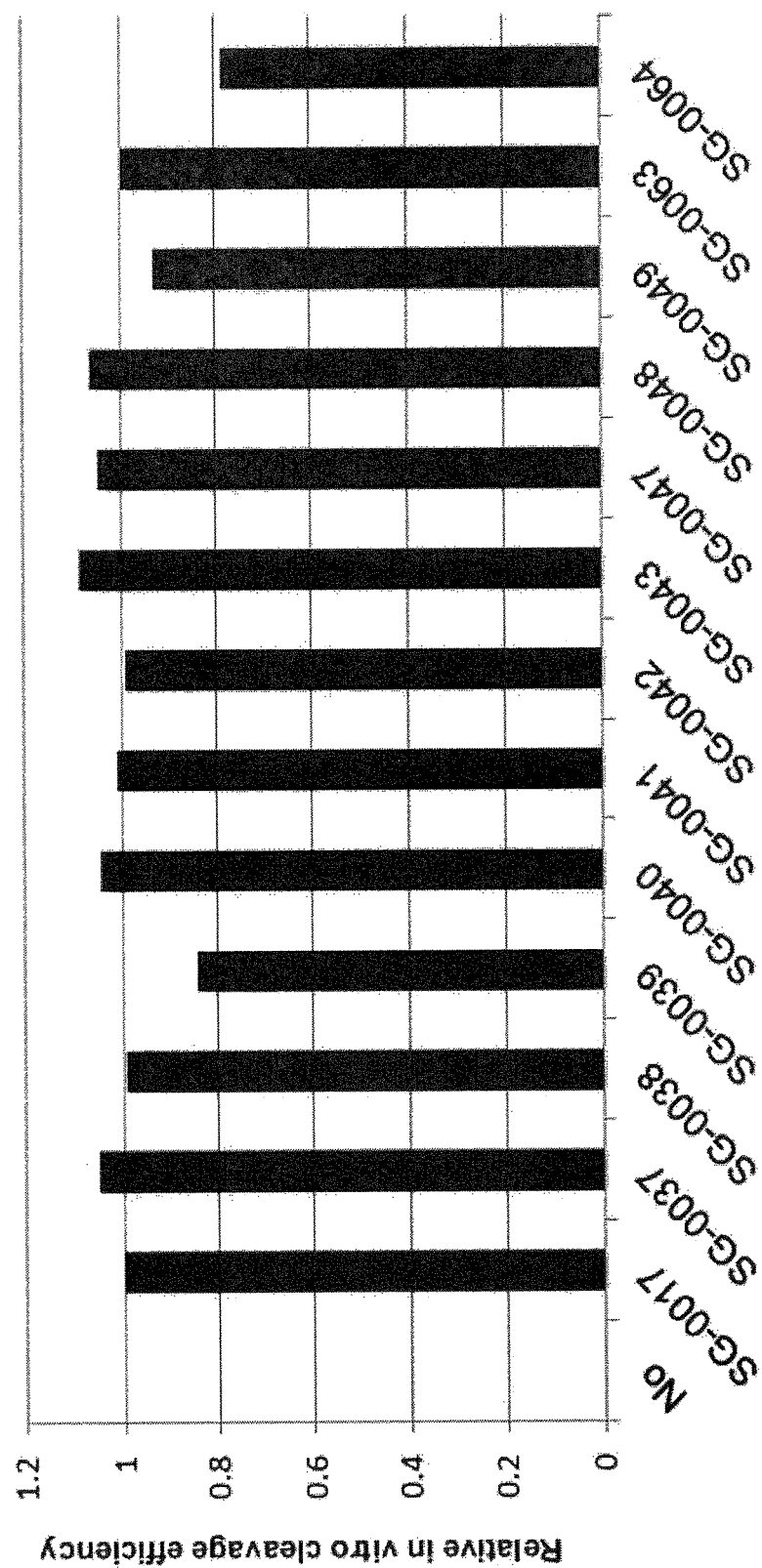
FIG. 9 shows the in vitro cleavage activity of sgRNA targeting BCL-2 gene.

The results are shown in FIG. 8. The numerical value under the gel shows cleavage efficiency determined by the above-mentioned calculation formula. Furthermore, the relative cleavage efficiency of the artificial sgRNA of this Example relative to the cleavage efficiency of natural form sgRNA (SG-0017) in Reference Example as 1 is shown in FIG. 9.

The artificial sgRNAs of this Example showed cleavage efficiency equal to or higher than that of the natural form sgRNA in Reference Example, and it was clarified that substitution of each site with an amino acid derivative is effective.

(Experimental Example 5) Evaluation of In Vitro Cleavage Activity of sgRNA Targeting BRAF Gene Plasmid DNA (pCMV6-Entry-BRAF (V600E), OriGene Technologies) incorporating a sequence having a V600E mutation in human BRAF gene (GenBank accession No. NM_004333) was reacted with restriction enzyme Tth111I (TaKaRa) according to the attached protocol. After completion of the reaction, the DNA of interest was purified according to a conventional method and dissolved in TE buffer (10 mM Tris-HCl, pH 8, 1 mM EDTA) to a final concentration of 100 ng/μL to give a substrate DNA.

The above-mentioned substrate DNA was mixed with sgRNA and Cas9 as follows using the reagent attached to Cas9 Nuclease, *S. pyogenes* (New England Biolabs);

100 ng substrate DNA+0.5 ng sgRNA+0.3 pmol Cas9 (total amount 10 μL)

This was incubated at 37° C. for 15 min, and further incubated at 70° C. for 10 min to inactivate Cas9. Thereafter, electrophoresis was performed and, after ethidium bromide staining, the band intensity was measured using gel imagint system PXi4 (SYNGENE).

Based on the measurement results, the cleavage efficiency was calculated by the following equation.

Cleavage Efficiency=sum of cleaved band intensities/
(sum of the cleaved and uncleaved band intensities)

Figure 10:
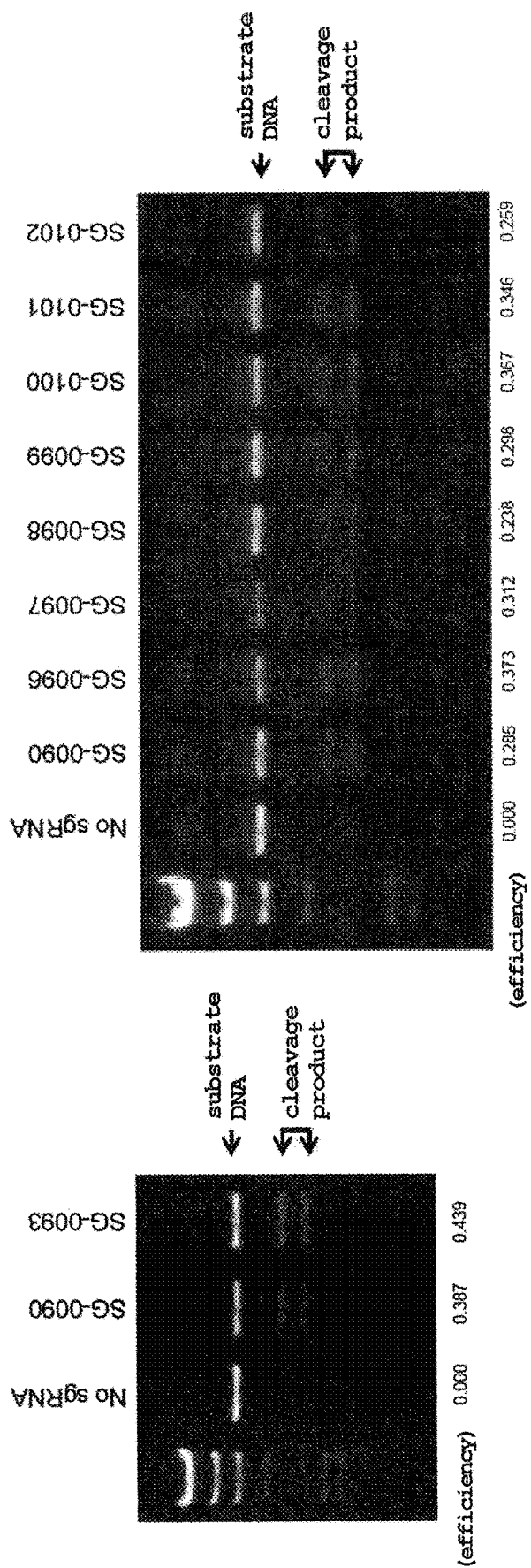
FIG. 10 shows the in vitro cleavage activity of sgRNA targeting BRAF gene.
Figure 11:
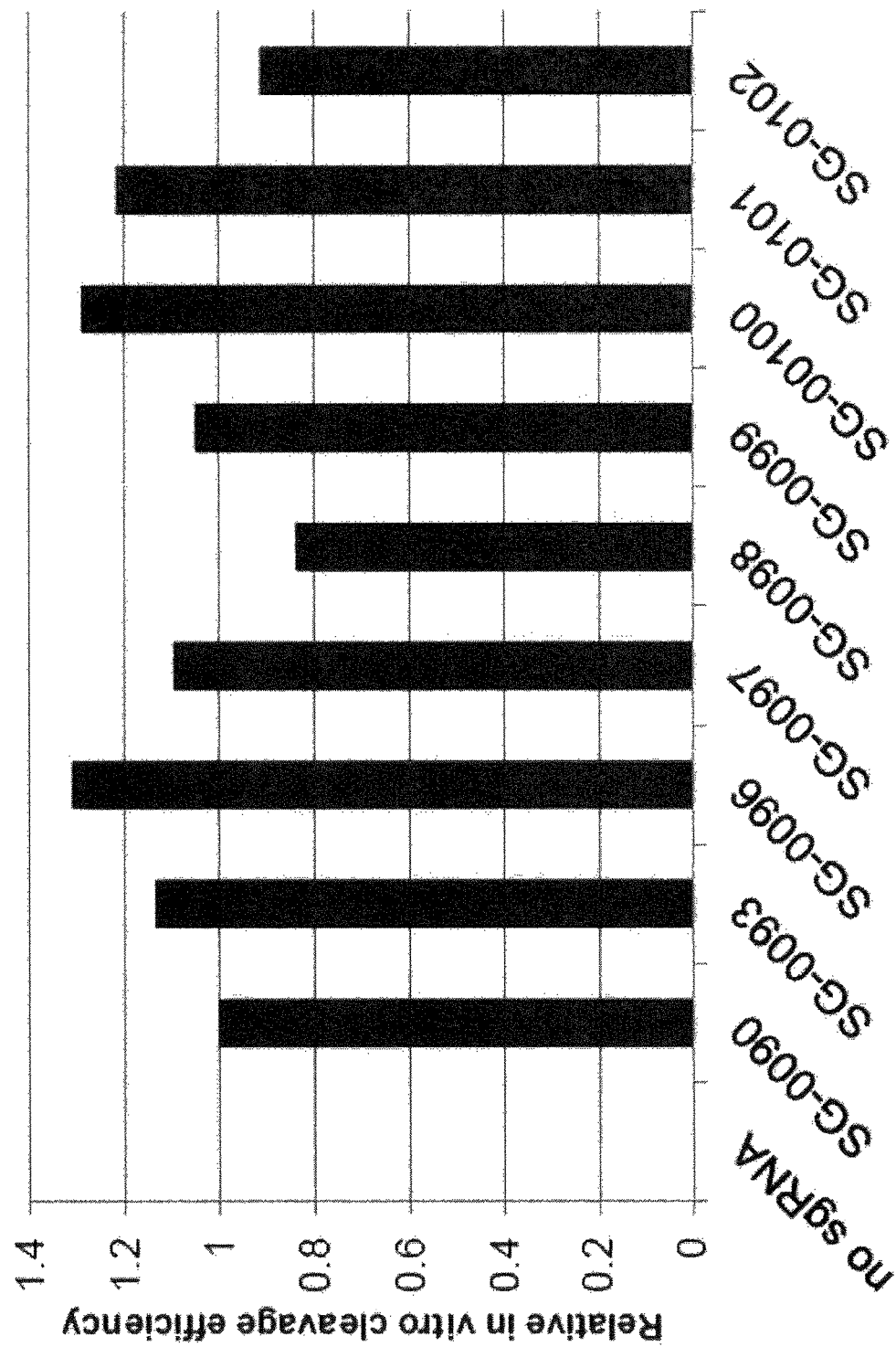
FIG. 11 shows the in vitro cleavage activity of sgRNA targeting BRAF gene.

The results are shown in FIG. 10. The numerical value under the gel shows cleavage efficiency determined by the above-mentioned calculation formula. Furthermore, the relative cleavage efficiency of the artificial sgRNA of this Example relative to the cleavage efficiency of natural form sgRNA (SG-0090) in Reference Example as 1 is shown in FIG. 11.

The artificial sgRNAs of this Example showed cleavage efficiency equal to or higher than that of the natural form sgRNA in Reference Example, and it was clarified that substitution of each site with an amino acid derivative is effective.

(Experimental Example 6) Evaluation of Intracellular Cleavage Activity of sgRNA Targeting BCL-2 Gene Jurkat cells ($2\times10^5$ cells) were collected in a microtube, washed with PBS, and suspended in a test substance solution (10 μL) obtained by adding 6 μg GeneArt Platinum Cas9 Nuclease (Thermo Fisher Scientific) and 1.2 μg sgRNA to ReSuspension buffer R attached to Neon 10 μL tip (Thermo Fisher Scientific). The cell suspension was sucked into Neon 10 μL tip and transfected using electroporator Neon (Thermo Fisher Scientific) under the conditions of Pulse Voltage 1700V, Pulse Width 20 ms, Pulse Number once. The obtained cells were seeded in RPMI1640 Medium (Thermo Fisher Scientific) (500 μL) containing 10% Fetal Bovine Serum (MP Biomedicals) in a 24-well Dish (Thermo Fisher Scientific). After culturing at 37° C. under 5% $CO_2$ for 48 hr, the cells were recovered, washed with PBS and genomic DNA was purified using GeneArt (registered trade mark) Genomic Cleavage Detection Kit (Thermo Fisher Scientific). Using a part of the obtained genomic DNA as a template and primer sets for human BCL-2 gene amplification: 5'-ATCAAGTGTTCCGCGTGATTGAAGA-3' (SEQ ID NO:84)/5'-CTCACATCACCAAGTGCACCTACCC-3' (SEQ ID NO:85), PCR was performed according to the protocol attached to GeneArt (registered trade mark) Genomic Cleavage Detection Kit. Using the obtained PCR product and according to the protocol attached to GeneArt (registered trade mark) Genomic Cleavage Detection Kit, chromosome in-del detection reaction was performed. Thereafter, agarose gel electrophoresis was performed, the gel was stained with ethidium bromide, and the band intensity on the gel was measured using gel imagint system PXi4 (SYNGENE).

Based on the measurement results, the cleavage efficiency was calculated by the following equation.

Cleavage Efficiency=1−[(1−fraction cleaved)$^{1/2}$]

Fraction Cleaved=sum of cleaved band intensities/
(sum of the cleaved and parental band intensities)

Figure 12:
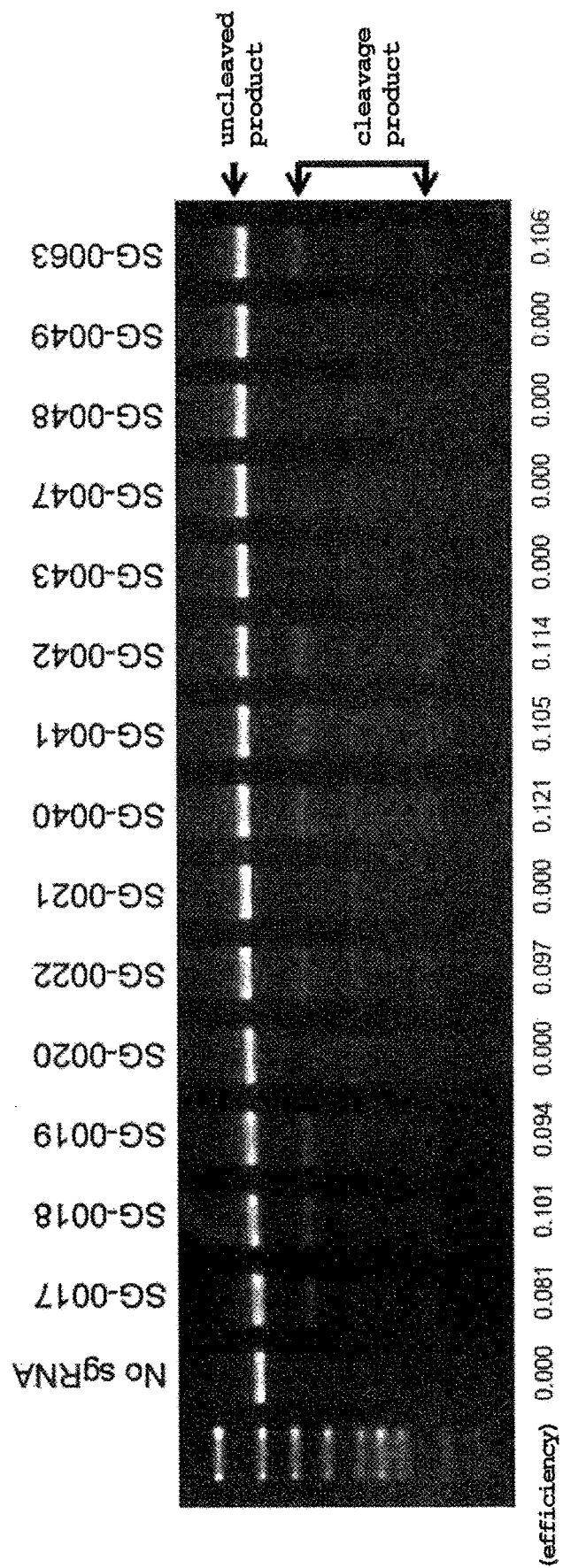
FIG. 12 shows the intracellular cleavage activity of sgRNA targeting BCL-2 gene.
Figure 13:
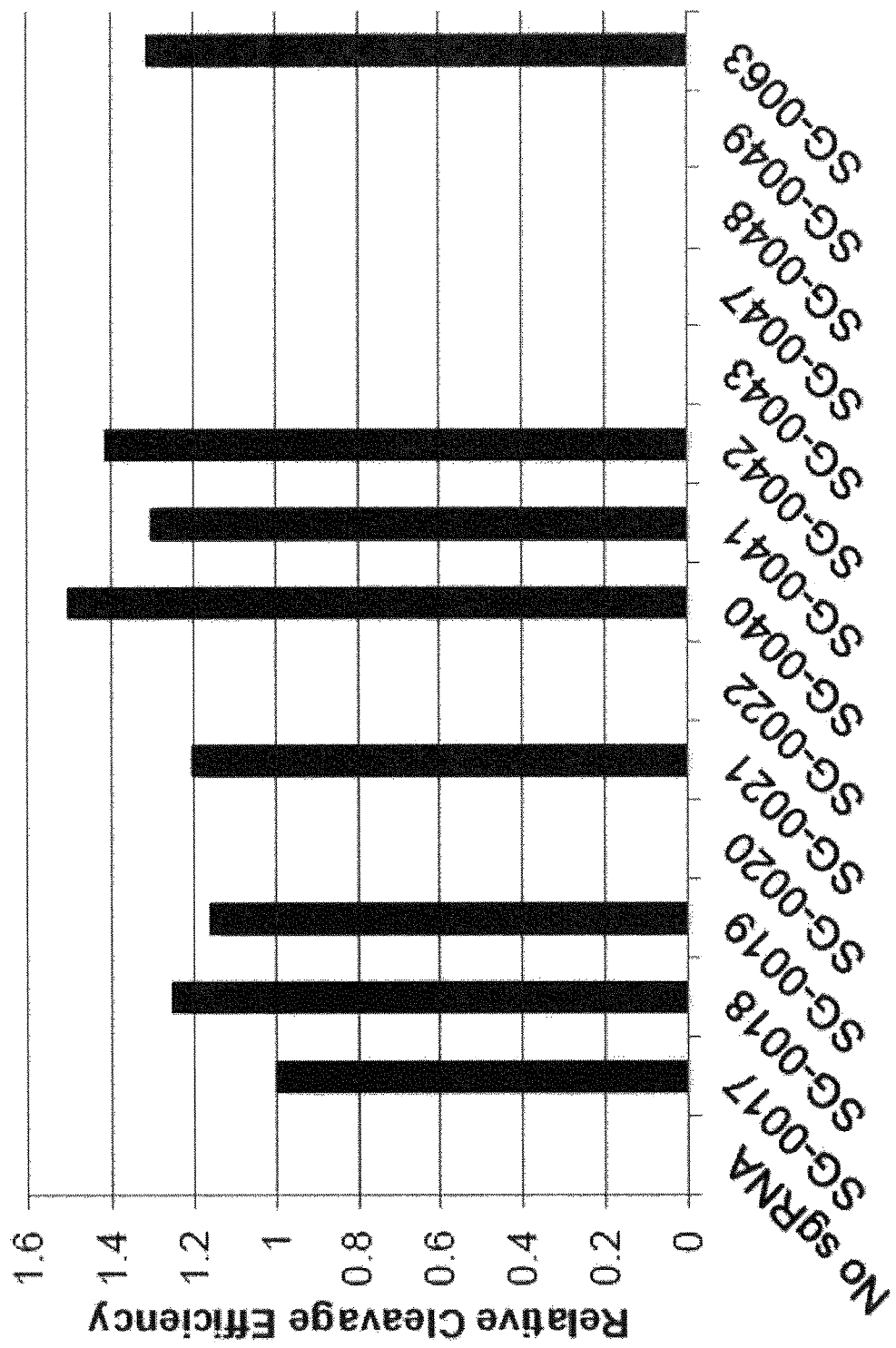
FIG. 13 shows comparison of the intracellular cleavage activity between artificial sgRNA targeting BCL-2 gene and natural form sgRNA.

The results thereof are shown in FIG. 12. The numerical value under the gel shows cleavage efficiency determined by the above-mentioned calculation formula. Furthermore, the relative cleavage efficiency of the artificial sgRNA of this Example relative to the cleavage efficiency of natural form sgRNA (SG-0017) in Reference Example as 1 is shown in FIG. 13.

Some of the artificial sgRNAs of this Example showed cleavage efficiency equal to or higher than that of the natural form sgRNA in Reference Example also in the cells.

(Experimental Example 7) Evaluation of Intracellular Cleavage Activity of sgRNA Targeting BRAF Gene A-375 cells ($5.6\times10^4$ cells) were collected in a microtube, washed with PBS, and suspended in a test substance solution (10 μL) obtained by adding 6 μg GeneArt Platinum Cas9 Nuclease (Thermo Fisher Scientific) and 1.2 μg sgRNA to ReSuspension buffer R attached to Neon 10 μL tip (Thermo Fisher Scientific). The cell suspension was sucked into Neon 10 μL tip and transfected using electroporator Neon (Thermo Fisher Scientific) under the conditions of Pulse Voltage 1400V, Pulse Width 20 ms, Pulse Number twice. The obtained cells were seeded in Dulbecco's Modified Eagle's Medium (High Glucose) (Sigma Aldrich) (500 μL) containing 10% Fetal Bovine Serum (MP Biomedicals) in a 24-well Dish (Thermo Fisher Scientific). After culturing at 37° C. under 5% $CO_2$ for 48 hr, the cells were washed with PBS and genomic DNA was purified using GeneArt (registered trade mark) Genomic Cleavage Detection Kit (Thermo Fisher Scientific). Using a part of the obtained genomic DNA as a template and primer sets for human BRAF gene amplification: 5'-CGCCCAGGAGTGCCAAGAGAATATC-3' (SEQ ID NO:86)/5'-CAGCAGCATCTCAGGGCCAAAAAT-3' (SEQ ID NO:87), PCR was performed according to the protocol attached to GeneArt (registered trade mark) Genomic Cleavage Detection Kit. Using the obtained PCR product and according to the protocol attached to GeneArt (registered trade mark) Genomic Cleavage Detection Kit, chromosome in-del detection reaction was performed. Thereafter, agarose gel electrophoresis was performed, the gel was stained with ethidium bromide, and the band intensity on the gel was measured using gel imagint system PXi4 (SYNGENE).

Based on the measurement results, the cleavage efficiency was calculated by the following equation.

Cleavage Efficiency=1−[(1−fraction cleaved)$^{1/2}$]

Fraction Cleaved=sum of cleaved band intensities/(sum of the cleaved and parental band intensities)

Figure 14:
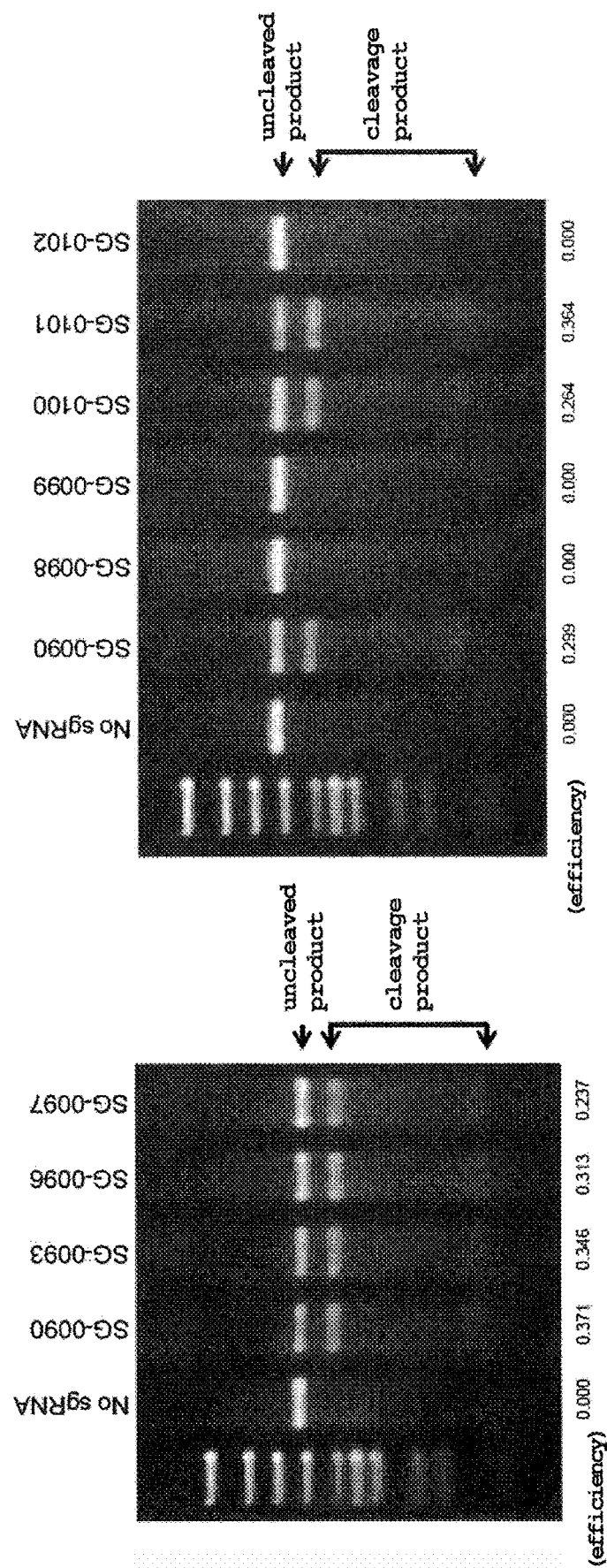
FIG. 14 shows the intracellular cleavage activity of sgRNA targeting BRAF gene.
Figure 15:
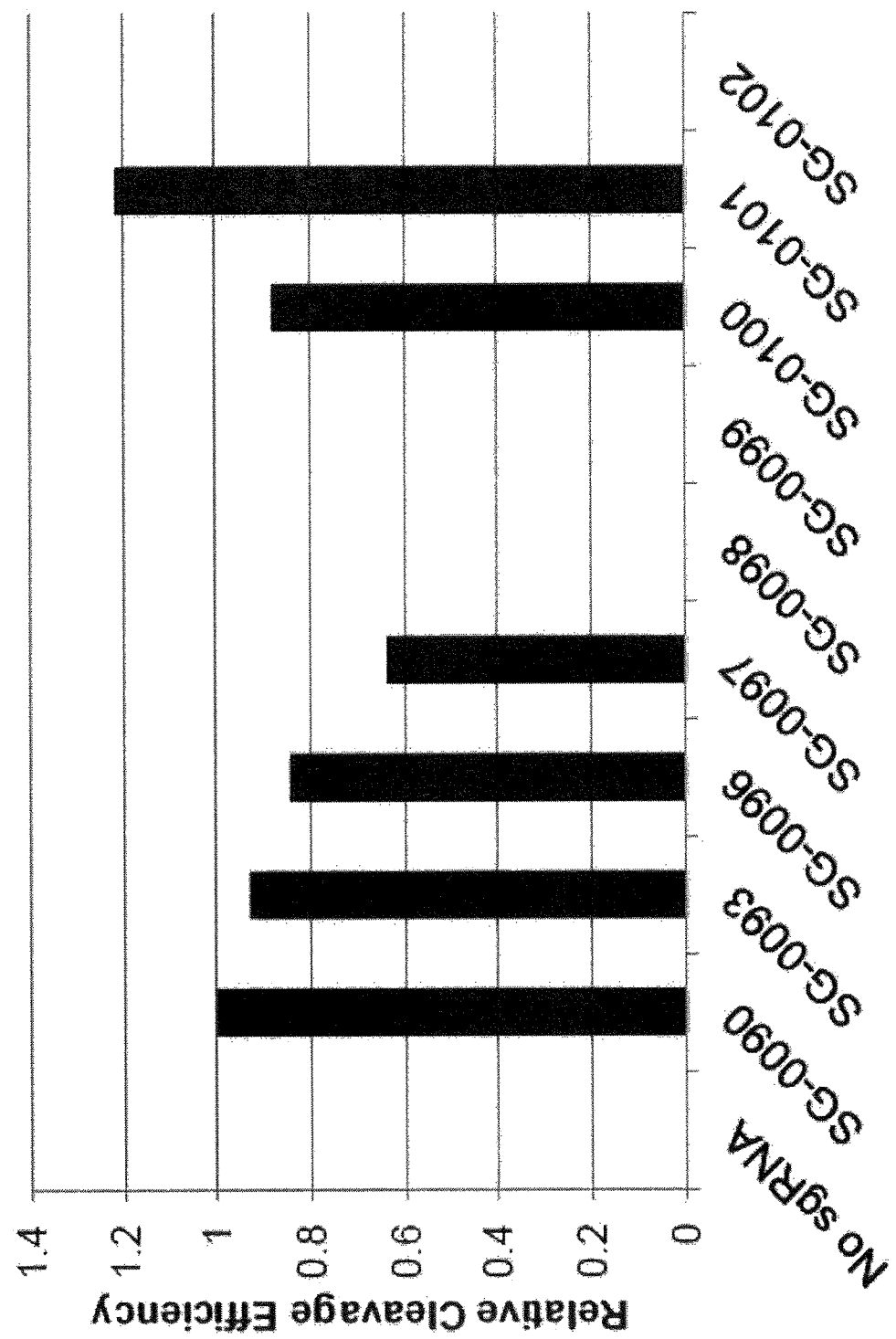
FIG. 15 shows comparison of the intracellular cleavage activity between artificial sgRNA targeting BCL-2 gene and natural form sgRNA.

The results thereof are shown in FIG. 14. The numerical value under the gel shows cleavage efficiency determined by the above-mentioned calculation formula. Furthermore, the relative cleavage efficiency of the artificial sgRNA of this Example relative to the cleavage efficiency of natural form sgRNA (SG-0090) in Reference Example as 1 is shown in FIG. 15.

Some of the artificial sgRNAs of this Example showed cleavage efficiency equal to or higher than that of the natural form sgRNA in Reference Example also in the cells.

While the present invention has been explained above by referring to embodiments, the present invention is not limited by the above-mentioned embodiments. The constitution and detail of the present invention can be modified variously as long as those skilled in the art can understand within the scope of the present invention.

The contents disclosed in any publication cited herein, including patents and patent applications, are hereby incorporated in their entireties by reference, to the extent that they have been disclosed herein.

This application is based on a patent application No. 2016-016743 filed in Japan (filing date: Jan. 30, 2016), the contents of which are incorporated in full herein.

INDUSTRIAL APPLICABILITY

The artificial sgRNA of the present invention can be synthesized easily at a low cost and can improve the in vivo stability when combined with Cas9 while maintaining DSB activity equal to or higher than that of natural form sgRNA. Therefore, it is useful for improving genome editing efficiency, particularly genome editing efficiency in vivo.

The invention claimed is:

1. A single guide RNA
(1) represented by formula (A):

(A)

```
5'- X^c(n)_20-
              GUUUUAGA--GCUA
              :|||||   ||||  X^a
            U C-GGAAUAAAAUUGAACGAU
            A    | ||  :
             GUCCG---Y---AACUU
                     :||||   X^b
                 AGCCACGGUGAA
              G  ||||||
               UCGGUGCUX^d U -3'
```

[in the formula (A), $X^a$ is an amino acid derivative linker represented by any of:

(a) formulas (II-1) to (II-9):

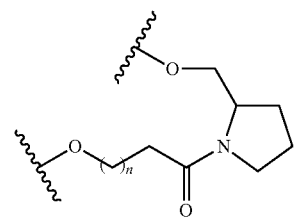

(II-1)

129
-continued (II-2)
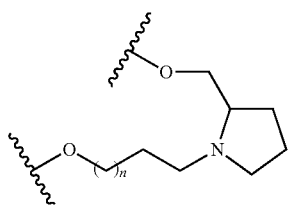

(II-3)
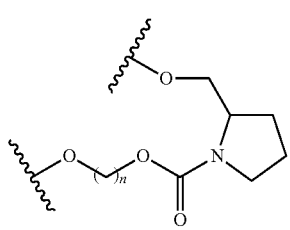

(II-4)
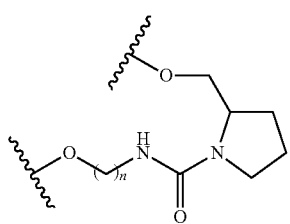

(II-5)
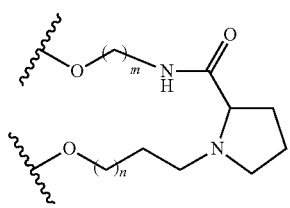

(II-6)
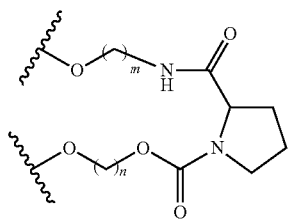

(II-7)
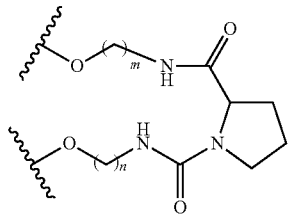

(II-8)
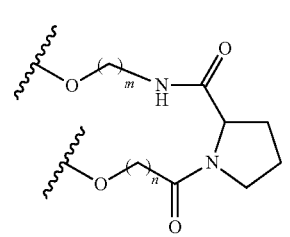

130
-continued (II-9)
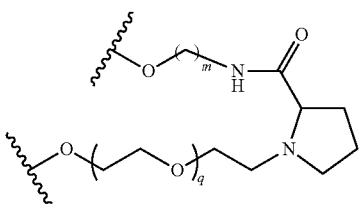

wherein n and m are each independently an integer of 0-15, and q is an integer of 0-10, and (b) formulas (III-1) to (III-3):

(III-1)
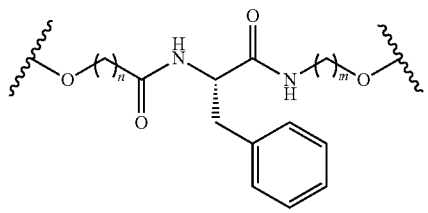

(III-2)
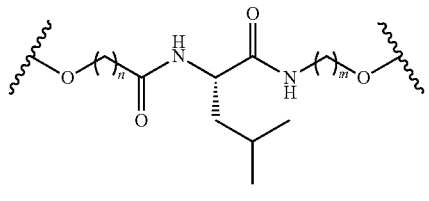

(III-3)
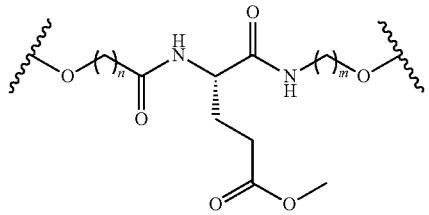

wherein n and m are each independently an integer of 0-15, in the formula (A), $X^b$ and Y are each independently a 1 to 5 optional nucleotide linker, in the formula (A), $X^c$ and $X^d$ may or may not be present, and when they are present, they are each independently an amino acid derivative linker represented by any of the formulas (II-1) to (II-9) wherein n and m are each independently an integer of 0-15 and q is an integer of 0-10, and in the formula (A), $(n)_{20}$ is a nucleotide sequence consisting of 20±5 nucleotide residues each of which is independently A, G, C or U], or (2) represented by the formula (A), wherein 1 to several nucleotide residues are substituted, deleted, inserted or added in a region excluding $(n)_{20}$, which RNA forming a complex with Cas9 protein and having an activity of recognizing a double-stranded DNA containing a target nucleotide sequence complementary to the $(n)_{20}$.

2. The single guide RNA according to claim 1, wherein $X^a$ is represented by the formula (II-8) wherein n=5 and m=4, n=7 and m=6, n=9 and m=8, or n=11 and m=10.

3. The single guide RNA according to claim 1, wherein $X^a$ is represented by the following formula (III-1)-(III-3):

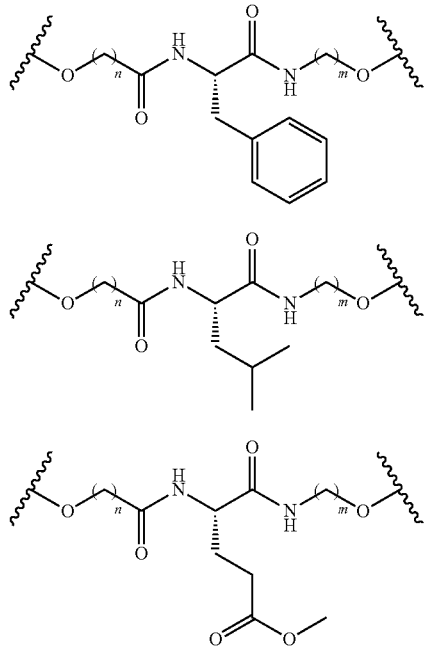

wherein n=5 and m=4, and
wherein Xc and Xd are absent.

4. The single guide RNA according to claim 1, wherein $X^b$ and Y comprise GAAA and UUAUC, respectively.

5. The single guide RNA according to claim 4, wherein $X^c$ and $X^d$ are absent.

6. The single guide RNA according to claim 4, wherein $X^c$ and $X^d$ are represented by the formula (II-8) wherein n=5 and m=4.

7. The single guide RNA according to claim 4, wherein $X^c$ and $X^d$ are represented by any of the formulas (III-1)-(III-3), wherein n=5 and m=4.

8. A CRISPR/Cas9 system comprising the single guide RNA according to claim 1 and Cas9 in combination.

9. The CRISPR/Cas9 system according to claim 8, wherein said Cas9 is derived from *Streptococcus pyogenes*.

10. The CRISPR/Cas9 system according to claim 8, wherein said Cas9 is in the form of a protein, an mRNA encoding same or an expression vector comprising a DNA encoding same.

11. A method for recognizing a double-stranded DNA, comprising contacting the CRISPR/Cas9 system according to claim 8 with a target double-stranded DNA.

12. The method according to claim 11, wherein the Cas9 protein has a double-stranded DNA cleavage activity.

13. The method according to claim 12, wherein said double-stranded DNA is cleaved in a cell.

14. The method according to claim 13, for knocking out a target gene.

15. The method according to claim 13, for modifying a base in the target gene, or inserting an exogenous gene in the gene.

16. The single guide RNA according to claim 2, wherein n=5 and m=4 in the formula (II-8).

17. The single guide RNA according to claim 16, wherein $X^c$ and $X^d$ are absent.

18. The single guide RNA according to claim 17, wherein $X^b$ and Y comprise GAAA and UUAUC, respectively.

19. The single guide RNA according to claim 16, wherein $X^c$ and $X^d$ are an amino acid derivative linker represented by the formula (II-8) wherein n=5 and m=4, n=7 and m=6, n=9 and m=8, or n=11 and m=10.

20. The single guide RNA according to claim 19, wherein n=5 and m=4 in the formula (II-8).

21. The single guide RNA according to claim 20, wherein $X^b$ and Y comprise GAAA and UUAUC, respectively.

* * * * *